United States Patent
Feldman et al.

(10) Patent No.: US 9,633,277 B2
(45) Date of Patent: Apr. 25, 2017

(54) APPARATUS AND METHODS FOR IDENTIFYING AND EVALUATING BRIGHT SPOT INDICATIONS OBSERVED THROUGH OPTICAL COHERENCE TOMOGRAPHY

(71) Applicant: Research Development Foundation, Carson City, NV (US)

(72) Inventors: Marc D. Feldman, San Antonio, TX (US); Thomas E. Milner, Austin, TX (US); Jennifer E. Whedbee, San Antonio, TX (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 14/852,479

(22) Filed: Sep. 11, 2015

(65) Prior Publication Data
US 2016/0078309 A1    Mar. 17, 2016

Related U.S. Application Data

(60) Provisional application No. 62/049,914, filed on Sep. 12, 2014.

(51) Int. Cl.
*G06K 9/00* (2006.01)
*G06K 9/46* (2006.01)
(Continued)

(52) U.S. Cl.
CPC .......... *G06K 9/4661* (2013.01); *A61B 5/0066* (2013.01); *A61B 5/0084* (2013.01);
(Continued)

(58) Field of Classification Search
CPC .............. G01B 9/0203; G01B 9/02091; G06T 7/0012; G06T 7/0051; G06T 7/0081;
(Continued)

(56) References Cited

U.S. PATENT DOCUMENTS

| 6,249,630 B1 | 6/2001 | Stock et al. |
| 2002/0101593 A1 | 8/2002 | Yang et al. |

(Continued)

FOREIGN PATENT DOCUMENTS

| IT | WO 2014002067 A3 * | 1/2014 | ............... G06T 7/00 |
| WO | WO 2006/004743 | 1/2006 | |
| WO | WO 2014/002067 | 1/2014 | |

OTHER PUBLICATIONS

Popescu et al., "Optical coherence tomography: fundamental principles, instrumental designs and biomedical applications", Aug. 6, 2011, Canada, Retrieved from Internet on Nov. 17, 2016 from: <http://nparc.cisti-icist.nrc-cnrc.gc.ca/eng/view/accepted/?id=70f8baef-21c8-459f-b465-d0e07e28e713>.*

(Continued)

*Primary Examiner* — Gregory F Cunningham
(74) *Attorney, Agent, or Firm* — Parker Highlander PLLC

(57) ABSTRACT

Exemplary embodiments of the present disclosure include apparatus and methods for identifying bright spot indications observed through optical coherence tomography. The indications can be evaluated, for example, to link risk factors or other conditions to clinically relevant outcomes.

41 Claims, 24 Drawing Sheets
(11 of 24 Drawing Sheet(s) Filed in Color)

(51) Int. Cl.
    A61B 5/00      (2006.01)
    G06K 9/52      (2006.01)
    G06T 7/00      (2017.01)
    G06T 7/60      (2017.01)
    A61B 5/02      (2006.01)
    G01B 9/02      (2006.01)
    A61B 1/04      (2006.01)

(52) U.S. Cl.
    CPC ........ *A61B 5/02007* (2013.01); *A61B 5/7246* (2013.01); *G01B 9/0203* (2013.01); *G01B 9/02091* (2013.01); *G06K 9/52* (2013.01); *G06T 7/0012* (2013.01); *G06T 7/0051* (2013.01); *G06T 7/0081* (2013.01); *G06T 7/60* (2013.01); *A61B 1/043* (2013.01); *G06K 2009/4666* (2013.01); *G06T 2207/10072* (2013.01); *G06T 2207/10101* (2013.01); *G06T 2207/20148* (2013.01); *G06T 2207/30021* (2013.01); *G06T 2207/30048* (2013.01); *G06T 2207/30101* (2013.01); *G06T 2207/30242* (2013.01)

(58) Field of Classification Search
    CPC . G06T 2207/10101; G06T 2207/20148; G06T 2207/30021; G06T 2207/30048; G06T 2207/30101; G06T 2207/10072; G06T 7/60; G06K 2009/4666; G06K 9/52; G06K 9/4661; A61B 5/0066
    USPC ........................................................ 382/131
    See application file for complete search history.

(56) References Cited

U.S. PATENT DOCUMENTS

| | | | |
|---|---|---|---|
| 2005/0002028 | A1 | 1/2005 | Kasapi et al. |
| 2005/0119552 | A1 | 6/2005 | Hochman |
| 2005/0171433 | A1 | 8/2005 | Boppart et al. |
| 2005/0265405 | A1 | 12/2005 | Mannstadt et al. |
| 2007/0081166 | A1 | 4/2007 | Brown |
| 2008/0117424 | A1 | 5/2008 | Teramura et al. |
| 2009/0021724 | A1 | 1/2009 | Mahadevan-Jansen et al. |
| 2009/0021746 | A1 | 1/2009 | Toida et al. |
| 2009/0185191 | A1 | 7/2009 | Boppart et al. |
| 2010/0094127 | A1* | 4/2010 | Xu ................... A61B 5/0066 600/425 |
| 2010/0286674 | A1 | 11/2010 | Ben-Yakar et al. |
| 2011/0032479 | A1 | 2/2011 | Utsunomiya |
| 2011/0300490 | A1 | 12/2011 | Rachet et al. |
| 2012/0075638 | A1 | 3/2012 | Rollins et al. |
| 2012/0140301 | A1 | 6/2012 | Xu |
| 2012/0203114 | A1 | 8/2012 | Bechtel et al. |
| 2014/0268168 | A1* | 9/2014 | Feldman ............ G01B 9/02091 356/479 |

OTHER PUBLICATIONS

Phipps et al., "Macrophages and Intravascular OCT Bright Spots", 2015 by the American College of Cardiology Foundation, published by Elsevier Inc., Retrieved from Internet on Nov. 17, 2016 from <imaging.onlinejacc.org/mobile/article.aspx?articleid=2041466>.*
Albota et al., "Two-photon fluorescence excitation cross sections of biomolecular probes from 690 to 960 nm", *Appl. Opt.*, 37(31): 7352-7356, 1998.
Arnida et al., "Geometry and surface characteristics of gold nanoparticles influence their biodistribution and uptake by macrophages", *Eur. J. Pharm. Biopharm.*, 77(3): 417-423 2011.
Bouhelier et al., "Surface plasmon characteristics of tunable photoluminescence in single gold nanorods", *Phys. Rev. Lett.*, 95(26): 2674051-2674054, 2005.
Boulesteix et al., "Micrometer scale ex vivo multiphoton imaging of unstained arterial wall structure", *Cytometry Part A*, 69A: 20-26, 2006.
Boyd et al., "Photoinduced luminescence from the noble metals and its enhancement on roughened surfaces", *Phys. Rev. B*, 33(12): 7923-7936, 1986.
Castellana et al., "Longitudinal surface plasmon resonance based gold nanorod biosensors for mass spectrometry", *Langmuir*, 26(8): 6066-6070, 2010.
Chen et al., "In situ real-time investigation of cancer cell photothermolysis mediated by excited gold nanorod surface plasmon", *Biomaterials*, 31(14): 4104-4112, 2010.
El-Sayed, "Some interesting properties of metals confined in time and nanometer space of different shapes", *Acc. Chem. Res.*, 34(4): 257-264, 2001.
Eustis and El-Sayed, "Aspect ratio dependence of the enhanced fluorescence intensity of gold nanorods: experimental and simulation study," *J. Phys. Chem. B*, 109(34): 16350-16356, 2005.
Fang et al., "Plasmon emission quantum yield of single gold nanorods as a function of aspect mtio", *ACS Nano*, 6(8): 7177-7184, 2012.
Fu and Gu, "Double-clad photonic crystal fiber coupler for compact nonlinear optical microscopy imaging", *Opt Lett.* 31: 1471-1473, 2006.
Fu et al., "Nonlinear optical endoscopy based on a double-clad photonic crystal fiber and a MEMS mirror", *Opt Exp.*, 14: 1027-1032, 2006.
Gans, "Form of ultramicroscopic particles of silver", *Ann. Phys.* 47(10): 270-284, 1915. (German).
Hauck et al., "Assessing the effect of surface chemistry on gold nanorod uptake, toxicity, and gene expression in mammalian cells", *Small*, 4(1): 153-159, 2008.
Huang et al., "Gold nanorods: from synthesis and properties to biological and biomedical applications," *Adv. Mater.*, 21(48): 4880-4910, 2009.
Hummel, *Electronic Properties of Materials*, 37-61, 4th ed. (Springer, New York, 2011).
Imura et al., "Near-field two-photon-induced photoluminescence from single gold nanorods and imaging of plasmon modes", *J. Phys. Chem. B*, 109(27): 13214-13220, 2005.
Jain et al., "Noble metals on the nanoscale: optical and photothermal properties and some applications in imaging, sensing, biology, and medicine", *Acc. Chem. Res.*, 41(12): 1578-1586, 2008.
Jain et al., "Review of some interesting surface plasmon resonance-enhanced properties of noble metal nanoparticles and their applications to biosystems", *Plasmonics*, 2(3): 107-118, 2007.
Ji et al., "Bifunctional Gold Nanoshells with a Superparamagnetic Iron Oxide-Silica Core Suitable for Both MR Imaging and Photothermal Therapy", *J. Phys. Chem. C*, 111(17): 6245-6251, 2007.
Kim et al., "Fiber-optic spectral polarimeter using a broadband swept laser source," *Optics Communications*, 249: 351-356, 2005.
Lal et al., "Nanoshell-enabled photothermal cancer therapy: impending clinical impact", *Acc. Chem. Res.*, 41(12): 1842-1851, 2008.
Le et al., "Label-free molecular imaging of atherosclerotic lesions using multimodal nonlinear optical microscopy", *J Biomed Opt.*, 12(5): 0540071-05400710, 2007.
Lee and El-Sayed, "Dependence of the enhanced optical scattering efficiency relative to that of absorption for gold metal nanorods on aspect ratio, size, end-cap shape and medium refractive index," *J. Phys. Chem. B*, 109(43): 20331-20338, 2005.
Lilledahl et al., "Characterization of vulnerable plaques by multiphoton microscopy", *J Biomed Opt.*, 12(4): 0440051-04400512, 2007.
Link et al., "Laser-induced shape changes of colloidal gold nanorods using femtosecond and nanosecond laser pulses", *J. Phys. Chem. B*, 104(26): 6152-6163, 2000.
Link et al., "Simulation of the optical absorption spectra of gold nanorods as a function of their aspect ratio and the effect of the medium dielectric constant", *J. Phys. Chem. B*, 106(16): 3073-3077, 1999.

(56) References Cited

OTHER PUBLICATIONS

Liu et al., "Multiphoton microscopy system with a compact fiber-based femtosecond-pulse laser and handheld probe", *J Biophoton.*, 4: 34-39, 2011.
Longmire et al., "Clearance properties of nano-sized particles and molecules as imaging agents: considerations and caveats", *Nanomedicine (Lond)*, 3(5): 703-717, 2008.
Ma et al., "Small multifunctional nanoclusters (nanoroses) for targeted cellular imaging and thempy", *ACS Nano*, 3(9): 2686-2696, 2009.
Mohamed et al., "The 'lightning' gold nanorods: fluorescence enhancement of over a million compared to the gold metal", *Chem. Phys. Lett.*, 317(6): 517-523, 2000.
Mooradian, "Photoluminescence of metals", *Phys. Rev. Lett.*, 22(5): 185-187, 1969.
Nagesha et al., "In vitro imaging of embryonic stem cells using multiphoton luminescence of gold nanoparticles", *Int. J. Nanomedicine*, 2(4): 813-819, 2007.
Ni et al., "Tailoring longitudinal surface plasmon wavelengths, scattering and absorption cross sections of gold nanorods," *ACS Nano*, 2(4): 677-686, 2008.
Niidome et al., "PEG-modified gold nanorods with a stealth character for in vivo applications", *J. Control Release*, 114(3): 343-347, 2006.
Ohulchanskyy et al., "High-resolution light microscopy using luminescent nanoparticles", *WIREs Nanomed. Nanobiotechnol.*, 2(2): 162-175, 2010.
Okamoto and Imura, "Near-field imaging of optical field and plasmon wavefunctions in metal nanoparticles," *J. Mater. Chem.*, 16(40): 3920-3928, 2006.
Park et al., "Two-photon-induced photoluminescence imaging of tumors using near-infrared excited gold nanoshells", *Opt Exp.* 16(3): 1590-1599, 2008.
PCT International Search Report and Written Opinion issued in International Application No. PCT/US2015/049637, mailed Mar. 4, 2016.
PCT International Search Report and Written Opinion issued in International Application No. PCT/US2014/028403, mailed Sep. 10, 2014.
PCT Invitation to Pay Additional Fees issued in International Application No. PCT/US2015/049637, mailed Jan. 8, 2016.
Ryu et al., "Optical coherence tomography implemented by photonic crystal fiber", *Opt Quant Electron.*, 37(13-15): 1191-1198, 2005.
Shukla et al., "Biocompatibility of gold nanoparticles and their endocytotic fate inside the cellular compartment: a microscopic overview", *Langmuir*, 21(23): 10644-10654, 2005.
Skrabalak et al., "Gold nanocages for cancer detection and treatment", *Nanomedicine (Lond)*, 2(5): 657-668, 2007.
Sönnichsen and Alivisatos, "Gold nanorods as novel nonbleaching plasmon-based orientation sensors for polarized single-particle microscopy", *Nano Lett.*, 5(2): 301-304, 2005.
Sönnichsen et al., "Drastic reduction of plasmon damping in gold nanorods", *Phys. Rev. Lett.*, 88: 077402-077405, 2002.
Tong et al., "Gold nanorods as contrast agents for biological imaging: optical properties, surface conjugation and photothermal effects," *Photochem. Photobiol.*, 85(1): 21-32, 2009.
van Zandvoort et al., "Two-photon microscopy for imaging of the (atherosclerotic) vascular wall: a proof of concept study", *J Vasc Res.*, 41: 54-63, 2004.
Verma and Sekhon, "Influence of aspect ratio and surrounding medium on localized surface plasmon resonance (LSPR) of gold nanorod", *J. Optics.*, 41(2): 89-93, 2012.
Wang et al., "Combined two-photon luminescence microscopy and OCT for macrophage detection in the hypercholesterolemic rabbit aorta using plasmonic gold nanorose", *Lasers Surg. Med.*, 44(1): 49-59, 2012.
Wang et al., "Dual-wavelength multi-frequency photothermal wave imaging combined with OCT for macrophage and lipid detection in atherosclerotic plaques", *J Biomed Opt.*, 17(3): 0360091-03600910, 2012.
Wang et al., "In vitro and in vivo two-photon luminescence imaging of single gold nanorods", *Proc. Natl. Acad. Sci. USA*, 102(44): 15752-15756, 2005.
Wang et al., "Near-IR luminescence of monolayer-protected metal clusters", *J. Am. Chem. Soc.*, 127(3): 812-813, 2005.
Wilcoxon et al., "Photoluminescence from nanosize gold clusters", *J. Chem. Phys.*, 108(21): 9137-9143, 1998.
Winsemius et al., "Splitting of the intethand absorption edge in Au", *Phys. Rev. B*, 12(10): 4570-4572, 1975.
Wu et al., "Scanning fiber-optic nonlinear endomicroscopy with miniature aspherical compound lens and multimode fiber collector", *Opt Lett.*, 34: 953-955, 2009.
Xu and Webb, "Measurement of two-photon excitation cross sections of molecular fluorophores with data from 690 to 1050 nm", *JOSA B*, 13(3): 481-491, 1996.
Xue and Fujimoto, "Ultrahigh resolution optical coherence tomography with femtosecond Ti:sapphire laser and photonic crystal fiber", *Chinese Science Bulletin*, 53(13): 1963-1966, 2008.
Zhang et al., "Gold nanorods for fluorescence lifetime imaging in biology", *J. Biomed. Opt.*, 15(2): 0205041-0205043, 2010.
Zheng et al., "Highly fluorescent, water-soluble, size-tunable gold quantum dots", *Phys. Rev. Lett.*, 93(7): 077402-077405, 2004.
Zoumi et al., "Imaging coronary artery microstructure using secondharmonic and two-photon fluorescence microscopy", *Biophys J.*, 87: 2778-2786, 2004.

\* cited by examiner

APPARATUS AND METHODS FOR IDENTIFYING AND EVALUATING BRIGHT SPOT INDICATIONS OBSERVED THROUGH OPTICAL COHERENCE TOMOGRAPHY

CROSS-REFERENCE TO RELATED APPLICATIONS

This application claims priority to U.S. Provisional Patent Application Ser. No. 62/049,914 filed Sep. 12, 2014, the contents of which are incorporated by reference herein.

The invention was made with government support under Grant No. HL074464 awarded by the National Institutes of Health. The government has certain rights in the invention.

BACKGROUND INFORMATION

Atherosclerosis and plaque rupture leading to myocardial infarction remain the leading cause of death worldwide [1]. Inflammation and underlying cellular and molecular mechanisms [2-4] contribute to atherogenesis from initiation through progression, plaque rupture and ultimately, thrombosis. The vulnerable plaque, recently defined by Virmani [5] as "thin-cap fibroatheroma", results from inflammation and is characterized as having a thin fibrous cap typically less than 65 µm thick, increased infiltration of macrophages with decreased smooth muscle cells, and an increased lipid core size compared to stable plaques [6-8].

Several cellular and molecular events that lead to rupture of thin-cap fibroatheromas are now understood and being utilized to develop novel imaging approaches. Accumulations of macrophages in thin-cap fibroatheromas over-express matrix metalloproteinases (MMPs) [9-12] which are believed to contribute to vulnerability of thin-cap fibroatheromas and increased thrombogenicity [13-15]. Macrophages are an important early cellular marker that indicates the risk of plaque rupture in the coronary, cerebral, and peripheral circulations. Since plaque vulnerability is related to cellular composition as well as anatomical structure, developing a diagnostic method that can simultaneously reveal both composition and structure is desirable to identify vulnerable plaques and would allow in vivo monitoring of macrophage density in longitudinal studies in response to cardiovascular interventions.

Intravascular OCT (IVOCT) is a recently developed catheter-based method for high-resolution intravascular imaging. Of the cardiovascular imaging modalities, IVOCT is the only approach that provides sufficient spatial resolution to image thin-cap fibroatheromas.

However, risk of plaque rupture cannot be easily assessed by only IVOCT images. Two-photon luminescence (TPL) microscopy uses nonlinear optical properties of tissue and has been utilized to image plaque components such as endothelial cells, smooth muscle cells [16], elastin fibers [17,18], oxidized LDL [19] and lipid droplets [20] based on their endogenous autofluorescence. More recently, it has been reported that macrophages loaded with nanoparticles can be detected by TPL microscopy [21,22]. Fiber-based OCT [23,24] and TPL microscopy [25-28] has been reported respectively using photonic crystal fibers to transmit broadband light for achieving higher spatial resolution or to transmit ultrashort pulses for system size minimization. However, a combined fiber-based OCT-TPL system has not been previously realized.

SUMMARY

Exemplary embodiments of the present disclosure include apparatus comprising: an imaging device comprising an optical coherence tomography light source, where the imaging device is configured to obtain an image of a lumen via a catheter inserted into the lumen; and a non-transitory computer readable medium configured to perform the steps used in the evaluation of the image of the lumen. In certain embodiments, the steps can include: (1) identify the catheter; (2) identify the lumen; (3) obtain a plurality of A-scans and B-scans of the lumen; (4) calculate distances between the catheter and the lumen for each A-scan and the overall mean distance to the catheter ($Mean_{overall}$); (5) calculate the average of A-scans closer to the catheter than $Mean_{overall}$ ($A_{closer}$) and the average of A-scans further to the catheter than $Mean_{overall}$ ($A_{further}$); (6) normalize $A_{closer}$ and $A_{further}$ by the range of values in a B-scan (maximum value−minimum value), $A_{closerN}$ and $A_{furtherN}$; and (7) identify bright spots as those pixels in each A-scan that are greater than the corresponding pixels in $A_{closerN}$ or $A_{furtherN}$, depending on whether the A-scan lumen is closer or further to the catheter compared to $Mean_{overall}$.

In particular embodiments, the apparatus can be configured to analyze a spatial pattern of the bright spots. In some embodiments, the apparatus can be configured to document a clinically relevant outcome based on the spatial pattern of bright spots. In specific embodiments, the apparatus can be configured to analyze location depths of a plurality of bright spots, where the location depth of each bright spot is measured from a surface of the lumen to a location of the bright spot. In certain embodiments, the apparatus can be configured to document a clinically relevant outcome based on the location depths of the plurality of bright spots. In particular embodiments, the lumen can be a vascular wall of a blood vessel. In some embodiments, the apparatus can be configured to perform texture analysis of the lumen. In specific embodiments, the apparatus can be configured to document a clinically relevant outcome based on the texture analysis and a presence of bright spots. In certain embodiments, the optical coherence tomography light source can be configured as a swept source optical coherence tomography light source. In particular embodiments, the optical coherence tomography light source can be configured as a broadband optical coherence tomography light source.

In certain embodiments, the imaging device can further comprise: a splitter configured to direct a first wavelength emitted from the coherence tomography light source to a reference path and to a sample path, where the sample path is directed to the lumen through an optical fiber inserted into the catheter; a short-pulsed light source configured to emit a second wavelength; a first dichroic element and a second dichroic element; and a visual display configured to display an image of the lumen. In particular embodiments, the optical fiber can be a photonic crystal fiber. In some embodiments, the imaging device can further comprise a balanced detector. In specific embodiments, the balanced detector can be configured to minimize a non-interfering OCT component. In certain embodiments, the imaging device can further comprise a photon counting detector. In particular embodiments, the photon counting detector can be a photomultiplier tube. In some embodiments, the photon counting detector can be an avalanche photo diode. In specific embodiments, the photon counting detector can be configured to detect two-photon luminescence. In certain embodiments, the second dichroic element can be configured to direct two photon luminescence toward a photon counting detector. In particular embodiments, the first dichroic element can be configured to direct the first and second wavelengths to the sample path. In some embodiments, the sample path is directed to a sample site that comprises nanoparticles.

Certain embodiments can further comprise a visual display configured to display an image of the sample site. In particular embodiments, the nanoparticles can be configured as nanorods. In some embodiments, the nanorods can comprise gold and have a surface plasmon resonance of approximately 756 nm. Certain embodiments can further comprise a dispersion compensating element. In particular embodiments, the dispersion compensating element can be configured to compensate dispersion differences between the reference path and the sample path. In some embodiments, the dispersion compensating element can be configured to pre-compensate two-photon luminescence excitation light.

Certain embodiments can also include an apparatus comprising: an optical coherence tomography light source configured to emit a first wavelength; a splitter configured to direct the first wavelength emitted from the coherence tomography light source to a reference path and to a sample path, where the sample path is directed to a sample site through an optical fiber; a short-pulsed light source configured to emit a second wavelength; a first dichroic element and a second dichroic element; and a visual display configured to display an image of the sample site, wherein the apparatus is configured to enhance a portion of the image of the sample site based on the distance between the optical fiber and the sample site.

In particular embodiments, in order to enhance the portion of the image of the sample site, the apparatus can be configured to: obtain a plurality of A-scans and B-scans of the sample site; calculate distances between the optical fiber and the sample site for each A-scan and the overall mean distance to the optical fiber ($Mean_{overall}$); calculate the average of A-scans closer to the optical fiber than $Mean_{overall}$ ($A_{closer}$) and the average of A-scans further to the optical fiber than $Mean_{overall}$ ($A_{further}$); normalize $A_{closer}$ and $A_{further}$ by the range of values in a B-scan (maximum value−minimum value), $A_{closerN}$ and $A_{furtherN}$; and identify bright spots as those pixels in each A-scan that are greater than the corresponding pixels in $A_{closerN}$ or $A_{furtherN}$, depending on whether the A-scan sample site is closer or further to the optical fiber compared to $Mean_{overall}$. In some embodiments, the apparatus can be configured to analyze a spatial pattern of the bright spots. In specific embodiments, the apparatus can be configured to document a clinically relevant outcome based on the spatial pattern of bright spots. In certain embodiments, the apparatus can be configured to analyze location depths of a plurality of bright spots, wherein the location depth of each bright spot is measured from a surface of the sample site to a location of the bright spot. In particular embodiments, the apparatus can be configured to document a clinically relevant outcome based on the location depths of the plurality of bright spots. In some embodiments, the sample site can be a vascular wall of a blood vessel. In specific embodiments, the apparatus can be configured to perform texture analysis of the sample site. In certain embodiments, the apparatus can be configured to document a clinically relevant outcome based on the texture analysis and a presence of bright spots.

Certain embodiments can include a method of diagnosing a medical condition, where the method comprises: obtaining an image of a sample site using an optical coherence tomography light source emitting light from an optical fiber; obtaining a plurality of A-scans and B-scans of the sample site; calculating distances between the optical fiber and the sample site for each A-scan and the overall mean distance to the optical fiber ($Mean_{overall}$); calculating the average of A-scans closer to the optical fiber than $Mean_{overall}$ ($A_{closer}$) and the average of A-scans further to the optical fiber than $Mean_{overall}$ ($A_{further}$); normalizing $A_{closer}$ and $A_{further}$ by the range of values in a B-scan (maximum value−minimum value), $A_{closerN}$ and $A_{furtherN}$; and identifying bright spots as those pixels in each A-scan that are greater than the corresponding pixels in $A_{closerN}$ or $A_{furtherN}$, depending on whether the A-scan sample site is closer or further to the optical fiber compared to $Mean_{overall}$. In particular embodiments, the method can further comprise analyzing a spatial pattern of the bright spots. In some embodiments, the method can further comprise diagnosing a medical condition based on the spatial pattern of the bright spots. In specific embodiments, the method may further comprise analyzing location depths of a plurality of bright spots, where the location depth of each bright spot is measured from a surface of the sample site to a location of the bright spot. In certain embodiments, the method can comprise diagnosing a medical condition based on the location depths of the plurality of bright spots.

Exemplary embodiments of the present disclosure include a combined catheter-based optical coherence tomography-two-photon luminescence (OCT-TPL) imaging system to detect, and further characterize the distribution of cellular components (e.g., macrophage, collagen/elastin fiber, lipid droplet) in thin-cap fibroatheromas with high spatial resolution in vivo. Components of the catheter-based OCT-TPL system can include light sources for OCT (e.g., 1310 nm) and TPL (e.g., 800 nm), detectors for OCT (e.g., balanced detectors) and TPL (e.g., photon multiplier tubes), the transmission-grating compressor compensating the group delay dispersion of TPL excitation pulses, the fiber (e.g., photonic crystal fiber) delivering light from both OCT and TPL light sources and transmitting TPL emission signals, and the imaging catheter. Embodiments of the present disclosure describe methods and apparatus for imaging and related diagnostic and therapeutic catheter-based modalities that require the simultaneous delivery of short pulsed laser light and broadband OCT light.

Certain embodiments include an apparatus comprising: an optical coherence tomography light source configured to emit a first wavelength; a splitter configured to direct the first wavelength emitted from the coherence tomography light source to a reference path and to a sample path; a short-pulsed light source configured to emit a second wavelength; a first dichroic element; and a second dichroic element. In particular embodiments, the optical coherence tomography light source may be configured as a swept source optical coherence tomography light source. In certain embodiments, the optical coherence tomography light source may be configured as a broadband optical coherence tomography light source. In some embodiments, the short-pulsed light source may be a short-pulsed laser having a pulse energy between 10 pJ-1 mJ and a pulse duration between 5 fs-100 ps. In specific embodiments, the sample path may be directed through a photonic crystal fiber. Certain embodiments may include a balanced detector, and in particular embodiments, the balanced detector may be configured to minimize a non-interfering OCT component.

Particular embodiments may include a photon counting detector, and in certain embodiments, the photon counting detector may be a photomultiplier tube. In specific embodiments, the photon counting detector may be an avalanche photo diode. In some embodiments, the photon counting detector may be configured to detect two-photon luminescence. In certain embodiments, the second dichroic element may be configured to direct two photon luminescence toward a photon counting detector. In particular embodiments the first dichroic element may be configured to direct the first and second wavelengths to the sample path. In certain embodiments, the sample path may be directed to a sample site that comprises nanoparticles.

Particular embodiments may further comprise a visual display configured to display an image of the sample site. In certain embodiments, the visual display may be configured to enhance a portion of the display of the sample site based on the distance between the apparatus and the sample site. In some embodiments, the visual display may be configured to increase the brightness of a location of the sample site where a detected value exceeds a normalized value. In specific embodiments, the nanoparticles may be configured as nanorods. In certain embodiments, the nanorods comprise gold and have a surface plasmon resonance of approximately 756 nm. Particular embodiments may further comprise a dispersion compensating element, and in some embodiments, the dispersion compensating element is configured to compensate dispersion differences between the reference path and the sample path. In certain embodiments, the dispersion compensating element is configured to pre-compensate two-photon luminescence excitation light.

Particular embodiments may also include a method of imaging a sample site, where the method comprises: emitting a first wavelength from an optical coherence tomography light source toward a sample site; emitting a second wavelength from a short-pulsed light source toward the sample site; detecting an optical coherence tomography signal from the sample site, wherein the optical coherence tomography signal is generated from the first wavelength; and detecting a two-photon luminescence emission signal from the sample site, wherein the two-photon luminescence emission signal is induced by the second wavelength. In certain embodiments, the short-pulsed light source may be a short-pulsed laser having a pulse energy between 10 pJ-1 mJ and a pulse duration between 5 fs-100 ps.

In some embodiments, the optical coherence tomography signal and the two-photon luminescence signal may be detected from a plurality sample sites. In particular embodiments, the sample comprises a tissue, and in specific embodiments, the tissue may be epithelial tissue or arterial tissue. In certain embodiments, the arterial tissue may be located in a coronary artery. In specific embodiments, the tissue may be a vascular luminal surface. In particular embodiments, the tissue may be oral mucosa. In some embodiments, the optical coherence tomography signal may be used to generate an optical coherence tomography tomogram. In particular embodiments, the two-photon luminescence signal may be co-registered with an optical coherence tomography tomogram. Certain embodiments may further comprise displaying two-dimensional two-photon luminescence data on a three-dimensional optical coherence tomography tomogram. In some embodiments, a first processing element may use the optical coherence tomography signal and construct an optical coherence tomography tomogram.

In some embodiments, the first processing element may be a central processing unit or a graphics processing unit. In particular embodiments, a second processing element renders for viewing a co-registered two-photon luminescence image on an optical coherence tomography tomogram. In certain embodiments, the sample site may comprise a nanoparticle. In particular embodiments, the two-photon luminescence signal may be emitted from the nanoparticle. In specific embodiments, the two-photon luminescence emission signal may be emitted from tissue of the sample site.

Certain embodiments include a method for displaying imaging data, where the method comprises: obtaining optical coherence tomography data with an imaging system; obtaining two-photon luminescence data from a plurality of luminescing particles with the imaging system; and simultaneously displaying the optical coherence tomography data and the two-photon luminescence data in a combined image. In some embodiments, the luminescing particle may be a nanoparticle. In particular embodiments, the imaging system may be a catheter-based imaging system.

In certain embodiments, the optical coherence tomography data may comprise radial and azimuthal dimensional data, and the two-photon luminescence data may comprise an azimuthal signal. Particular embodiments may further comprise adding a radial dimension to the two-photon luminescence data. In certain embodiments, adding the radial dimension to the two-photon luminescence data may comprise using a radial probability distribution function that is normalized by the two-photon luminescence azimuthal signal. In specific embodiments, the radial probability distribution function may be determined using: optical properties of the imaging system; the distance between the catheter-based imaging system and a lumenal wall into which the catheter-based imaging system is inserted; and the optical properties of tissue of the lumenal wall.

In particular embodiments, the radial probability distribution function may be determined using assuming a uniform distribution of nanoparticles. Certain embodiments may further comprise generating three-dimensional images based on data obtained from the catheter-based imaging system as the catheter-based imaging system is moved axially along a lumen.

In the following, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The invention may be better understood by reference to one of these drawings in combination with the detailed description of specific embodiments presented herein.

DETAILED DESCRIPTION OF ILLUSTRATIVE EMBODIMENTS

Figure 1:
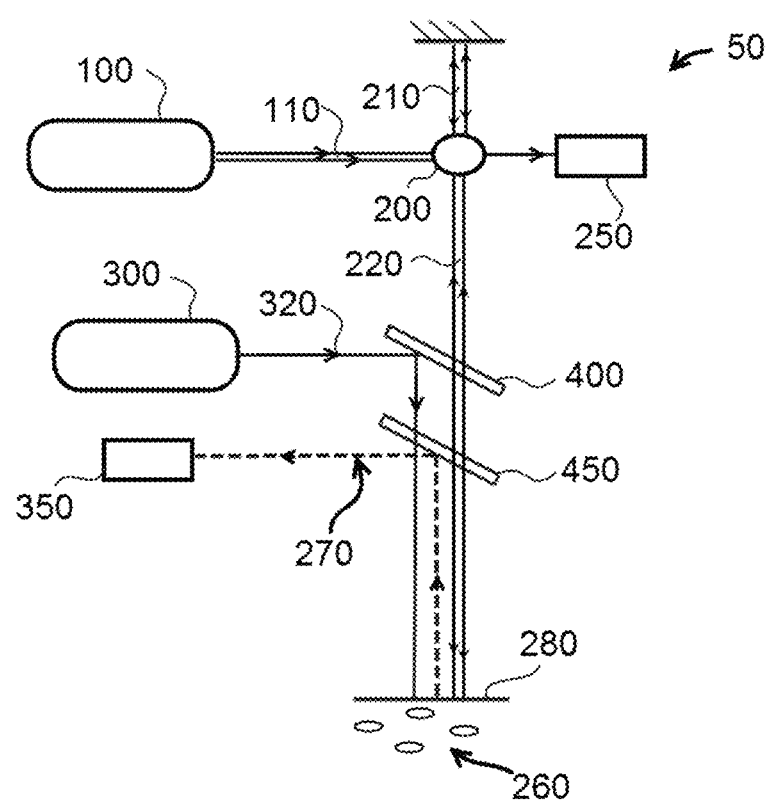
FIG. 1 shows a schematic of an apparatus according to an exemplary embodiment.

Referring now to FIG. 1, one exemplary embodiment of an apparatus 50 comprises an optical coherence tomography light source 100, a splitter 200, a two-photon luminescence excitation light source 300, a first dichroic element 400 and a second dichroic element 450. In this embodiment, optical coherence tomography light source 100 is configured to emit a first wavelength 110 and splitter 200 is configured to direct first wavelength 110 to a reference path 210 and a sample path 220. In certain embodiments, optical coherence tomography light source 100 can be configured as a swept source optical coherence tomography light source or a broadband optical coherence tomography light source. In particular embodiments, sample path 220 can be directed through a photonic crystal fiber. In the embodiment shown, two-photon luminescence excitation light source 300 is configured to emit a second wavelength 320.

During operation, apparatus 50 can be positioned such that sample path 220 and second wavelength 320 are directed to a sample site 280 (e.g. via first dichroic element 400 as well as other components in FIG. 1).

In certain exemplary embodiments, sample site 280 may comprise nanoparticles 260 and in specific embodiments, nanoparticles 260 may be configured as nanorods. In particular embodiments, nanoparticles 260 may be configured as nanorods comprising gold with a surface plasmon resonance of approximately 756 nm. In certain embodiments, the configuration of the nanorods can be selected according to the procedures established in the Example Section 4 provided below.

Apparatus 50 further comprises a photon counting detector 350 configured to detect two-photon luminescence (TPL) and a balanced detector 250 configured to minimize a non-interfering OCT component. In specific embodiments, photon counting detector 350 can be configured as one or more photomultiplier tubes (PMTs). In other embodiments, photon counting detector 350 can be configured as an avalanche photo diode.

In a particular embodiments, components of the system illustrated in FIG. 1 can be incorporated into a catheter-based system that utilizes a photonic crystal fiber (PCF) to enable the propagation of light in sample path 220 and second wavelength 320 from TPL excitation light source 300 to sample site 280. The PCF allows single-mode transmission of both OCT and TPL excitation light. Single-mode transmission is required in OCT imaging to insure the modal interference does not occur. Single mode transmission is required for TPL imaging to insure the pulse duration of TPL excitation light is not broadened due to modal dispersion. In specific embodiments the catheter can be inserted into a blood vessel to obtain intravascular images utilizing system 50.

During operation, system 50 provides the benefits of both OCT and TPL imaging technologies in a single system. In exemplary embodiments, the components of system 50 function according to established principles in OCT and TPL fields. Accordingly, while an overview of the individual OCT and TPL will be provided, it is understood that exemplary embodiments may utilize various combinations of parameters according to environmental conditions or other factors. For example, OCT light source 100 can produce near-infrared light, and the use of relatively long wavelength light allows deeper penetration into the scattering medium such as an arterial wall. In a particular embodiment OCT light source 100 can be configured to provide light at a wavelength of approximately 1310 nm.

As light in sample path 220 is directed at sample site 280, a small portion of this light that reflects from sub-surface features of sample site 280 is collected. During operation, a significant portion of light in sample path 220 is not reflected but, rather, backscatters from the sample. Although backscattered light contributes background that obscures an image in conventional imaging, this light can be used beneficially in OCT systems via interferometry. For example, balanced detector 250 can be used to record the optical path length of received photons, allowing rejection of most photons that multiply scatter in the tissue before detection. This can allow recording three-dimensional images of thick samples to be constructed by rejecting background signal while collecting light directly reflected from regions of interest in sample site 280. In exemplary embodiments, OCT imaging is generally limited to one to two millimeters below the surface in biological tissue in sample site 280. At greater depths, the proportion of light that escapes without scattering is typically too small for detection.

During operation of system 50, TPL light source 300 and photon counting detector 350 are also utilized consistent with established principles in two-photon luminescence microscopy. In certain embodiments, TPL light source 300 can be configured as a tunable femtosecond laser producing excitation energy of second wavelength 320 at 760-1040 nm with a maximum pulse energy of 6 nJ-5 μJ, a pulse width of 100 fs-1 ps, and a repetition rate of 500 kHz-80 MHz. In particular embodiments, TPL light source 300 may also be configured to produce a spot size of 10-30 μm with a spot area of approximately 78-706.8 μm$^2$ and a pixel dwell time of 20 μs. In addition, TPL light source 300 may also be configured to produce 10-1600 pulses per pixel, with an average power on sample of 500-2500 mW, an instantaneous power of 0.0625-5 MW and an instantaneous power density of 2E-4-16E-3 MW/μm$^2$.

In the embodiment shown in FIG. 1, first dichroic element 400 can be positioned to direct second wavelength 320 to sample site 280 via a photonic crystal fiber (PCF). In particular embodiments, the PCF can have a large sized mode field diameter (20 μm) (LMA-20) available from NKT Photonics. In certain embodiments, the PCF may be configured as a double-clad fiber, and in specific embodiments, may be a double-clad high NA fiber such as a model number DC-165-16-Passive Fiber available from Crystal Fibre. Exemplary double-clad photonic crystal fibers may comprise a large-mode area, single-mode core embedded in a high-NA multimode fiber structure. Such fibers can allow a single-mode beam to be propagated forward in the fiber and at the same time scattered light or two-photon luminescence may be collected and propagated backwards for detection. The use of a double-clad fiber instead of a single-clad photonic crystal fiber can increase the two-photon luminescence detection efficiency with a high-NA inner cladding (compared to the low-NA core). It is understood that the particular specifications of components are presented for purposes of example only, and that other embodiments may comprise components with different specifications than those described herein.

During operation of system 50, second wavelength 320 can provide excitation energy to nanoparticles 260, which can emit luminescence 270 that is directed to photon counting detector 350 via second dichroic element 450. In exemplary embodiments, the outputs from the photon counting detector 350 and balanced detector 250 can be configured to be combined in a single display that allows a user to visualize the results of both OCT and TPL imaging overlayed.

The display of the intravascular OCT and TPL images presents certain challenges to presenting the information to a user in a manner that can be quickly interpreted in a way that provides useful data. For example, intravascular OCT is two-dimensional (radial and azimuthal) while the TPL information in some embodiments is one-dimensional (azimuthal). A one-dimensional display of the TPL azimuthal information as a ring or band either inside or outside of the two-dimensional IV-OCT image was also evaluated as a way to present the combined IV-OCT and TPL image information.

Exemplary embodiments for displaying the combined IV-OCT and TPL comprise incorporating a radial dimension to the TPL data that uses a radial probability distribution function [p(r)] that will be normalized by the TPL azimuthal signal at that position. The radial probability distribution function [p(r)] can be determined from (in part): (1) the optics of the catheter; (2) distance between the catheter and lumenal wall; (3) tissue optical properties. This information can be combined to predict the radial dependence [p(r)] of the TPL signal that assumes a uniform distribution of nanoparticles 260.

With TPL information that includes both azimuthal and radial dependencies, the TPL and IV-OCT images can be fused to show both sets of information in one image data set. In addition, the same procedure can be followed for the entire pullback so that the three-dimensional IV-OCT and TPL datasets can be fused into a single image dataset.

Figure 2:
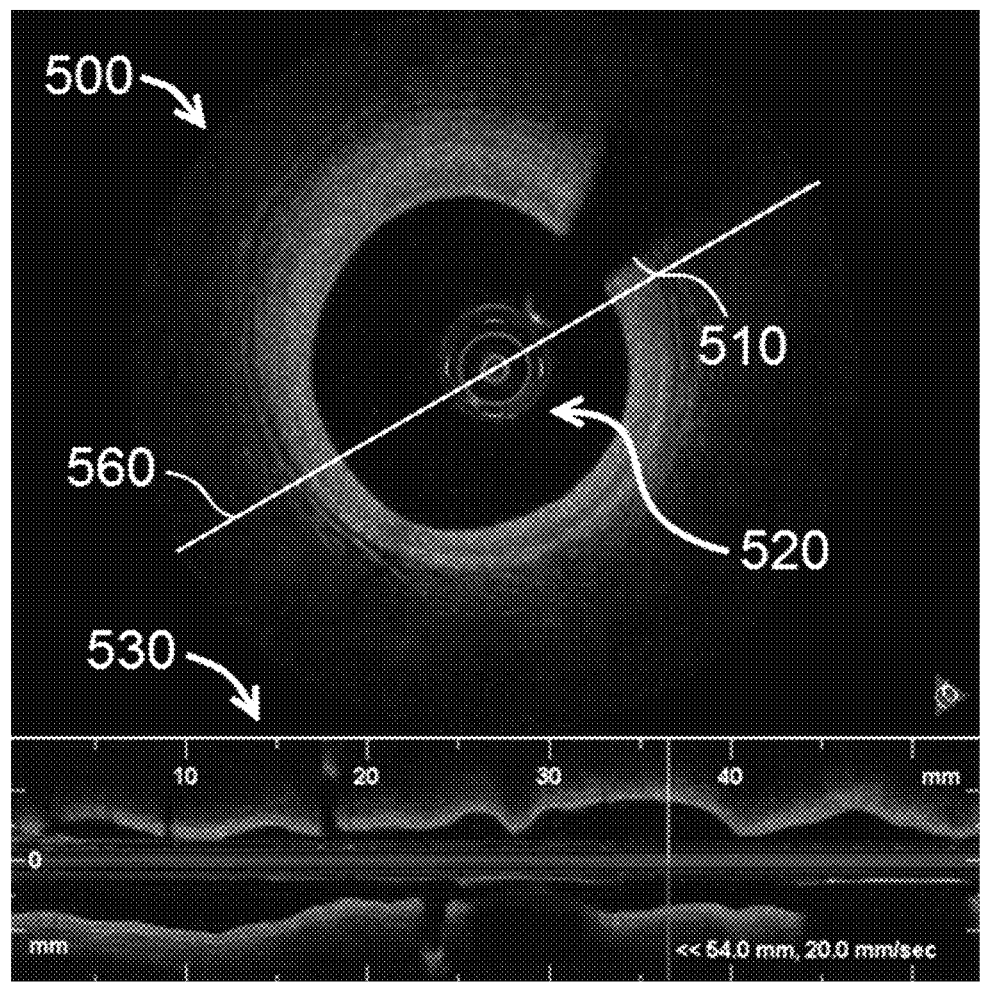
FIG. 2 shows an image obtained from an IV-OCT system.

Referring now to FIG. 2, an IV-OCT image 500 is produced using a catheter 510 configured to produce a typical IV-OCT image without combined TPL data. As shown in FIG. 2, image 500 shows a healthy coronary artery 520 with a substantially uniform wall. A side section view 530 of artery 520 is shown in the lower portion of FIG. 2. Side section view 530 is a reconstructed view of artery 520 taken along line 560 during pullback of catheter 510.

Figure 3:
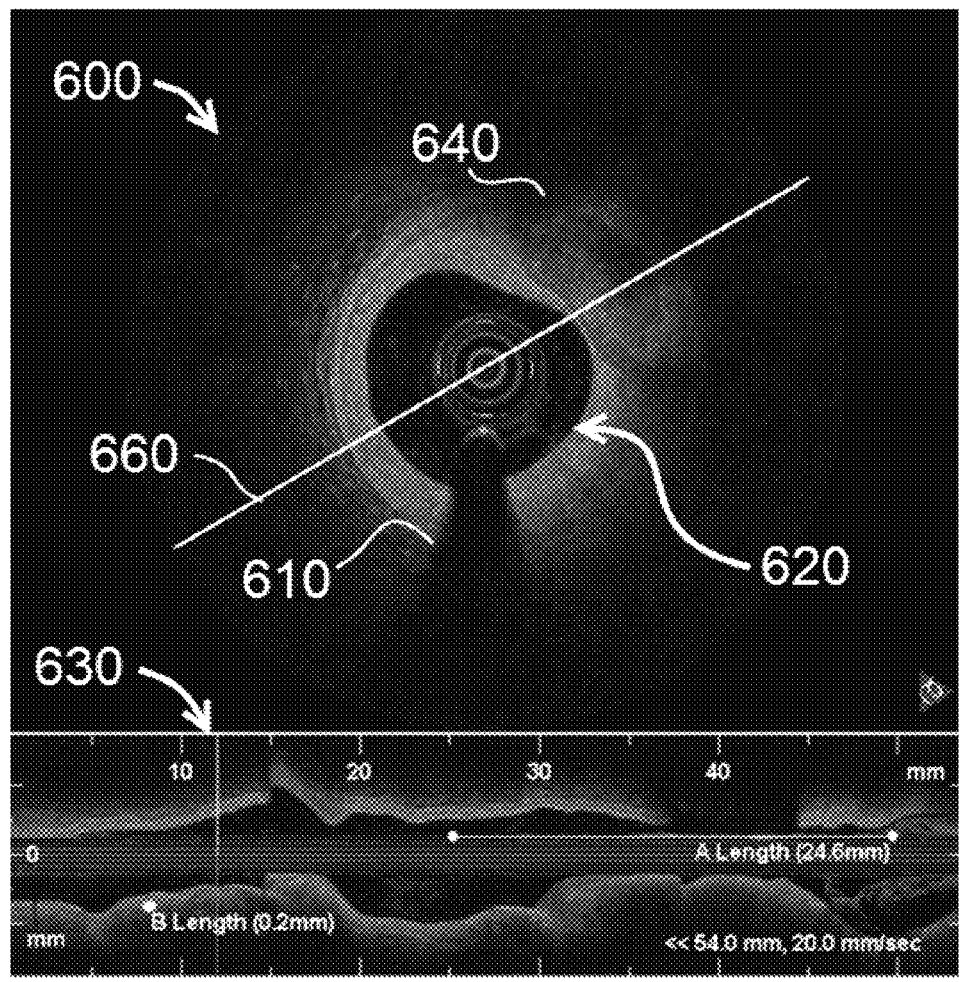
FIG. 3 shows an image obtained from an IV-OCT system.

Referring now to FIG. 3, an IV-OCT image 600 is produced using a catheter 610 configured to produce a typical IV-OCT image, also without combined TPL data. As shown in FIG. 3, image 600 shows a coronary artery 620 with a thin-cap fibroatheroma 640 overlying a large lipid core at approximately the 1:00-3:00 position. A side section view 630 of artery 620 is shown in the lower portion of FIG. 3. Side section view 630 is a reconstructed view of artery 620 taken along line 660 during pullback of catheter 610.

While image 600 shows thin-cap fibroatheroma 640, the risk of plaque rupture cannot be easily assessed from the image provided. Image 600 provides a view of the anatomical structure, but does not allow a user to evaluate the cellular composition. For example, image 600 does not directly provide an indication of the presence of macrophages, lipid deposits and collagen/elastin fibers, early cellular markers that can indicate the risk of plaque rupture.

Figure 4:
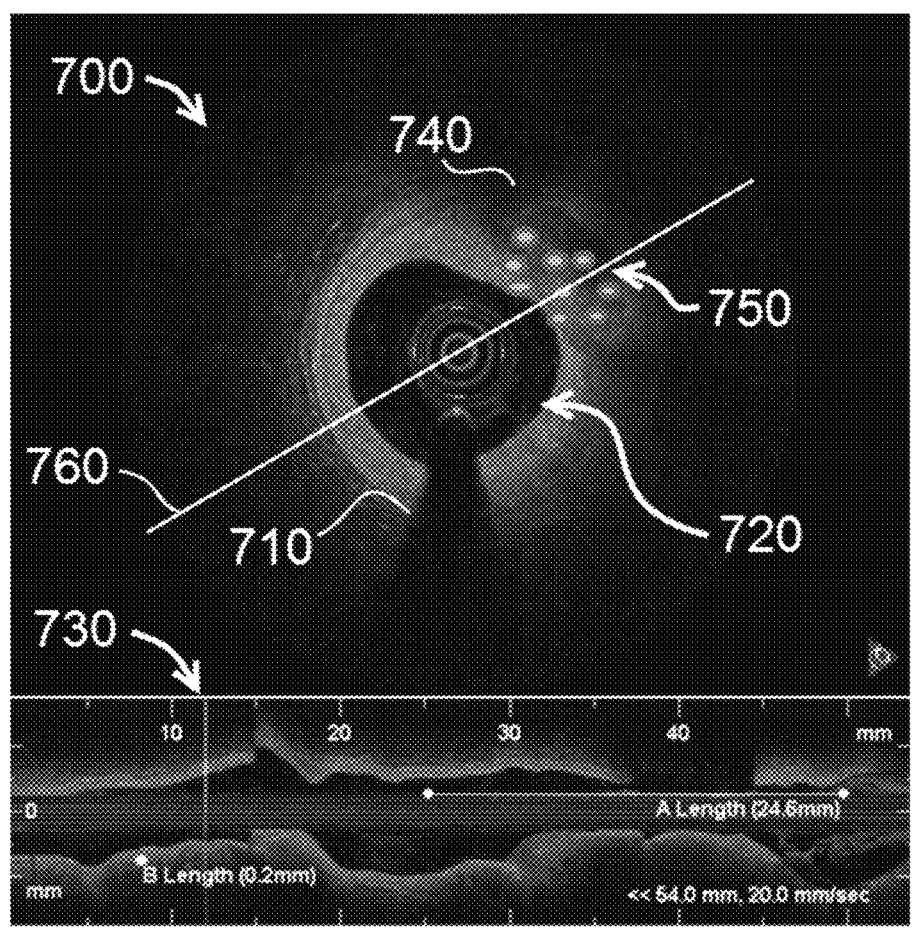
FIG. 4 shows an image obtained from an apparatus according to an exemplary embodiment.

Embodiments of the present invention (including, for example, system 50 shown in FIG. 1 or the specific example systems shown in FIG. 5A, 5B, 6 or 7) are configured to provide a combined OCT-TPL image, similar to that of image 700 as illustrated in FIG. 4. Image 700 can be produced by a combined OCT-TPL system examining a section of coronary artery. For example, coronary artery 720 comprises a thin-cap fibroatheroma 740 overlying a large lipid core at approximately the 1:00-3:00 o'clock position.

Unlike the image in FIG. 3, the image shown in FIG. 4 (an enhanced OCT-TPL image) does provide a user both a view of the anatomical structure and the ability to analyze the cellular composition of the structure. For example, a photon counting detector in exemplary OCT-TPL systems can detect two-photon luminescence (TPL) 750 from nanoparticles that may be concentrated in the thin-cap fibroatheroma 740 cellular components, including for example, macrophages, elastin fibers, and/or lipid droplets. The combined image of the anatomical structure, as well as indication of the cellular composition of the structure, can allow a user to perform a more thorough analysis of the plaque rupture risks associated with specific structures.

Exemplary embodiments of the present disclosure may also comprise computer readable media (e.g. software) to quantitatively analyze images obtained by the apparatus and enhance the visual display of certain aspects. For example, if a delivery device (e.g. a catheter or optical fiber) is not centered within a vascular lumen, light that is emitted from a site of interest that is farther away from the catheter may not appear as bright to the naked eye (as compared to light emitted from a site that is closer to the catheter or fiber).

Certain embodiments may also comprise apparatus and methods for enhancing an image of a sample site to compensate for the different distances between the site of interest and catheter/fiber to assist a user in analysis. For example, certain embodiments may calculate the distances between a delivery device (e.g. a catheter or optical fiber) for emitting light from an OCT light source and a sample site of a lumen. Based on distances between the sample site and the catheter/fiber, exemplary embodiments may identify bright spots in the image of the sample site.

For example, certain embodiments may include an apparatus comprising: an imaging device with an optical coherence tomography light source, where the imaging device is configured to obtain an image of a lumen via a catheter inserted into the lumen; and a non-transitory computer readable medium configured to perform the following steps used in the evaluation of the image of the lumen. In particular embodiments, the lumen may be the vascular wall of a blood vessel.

Figure 15:
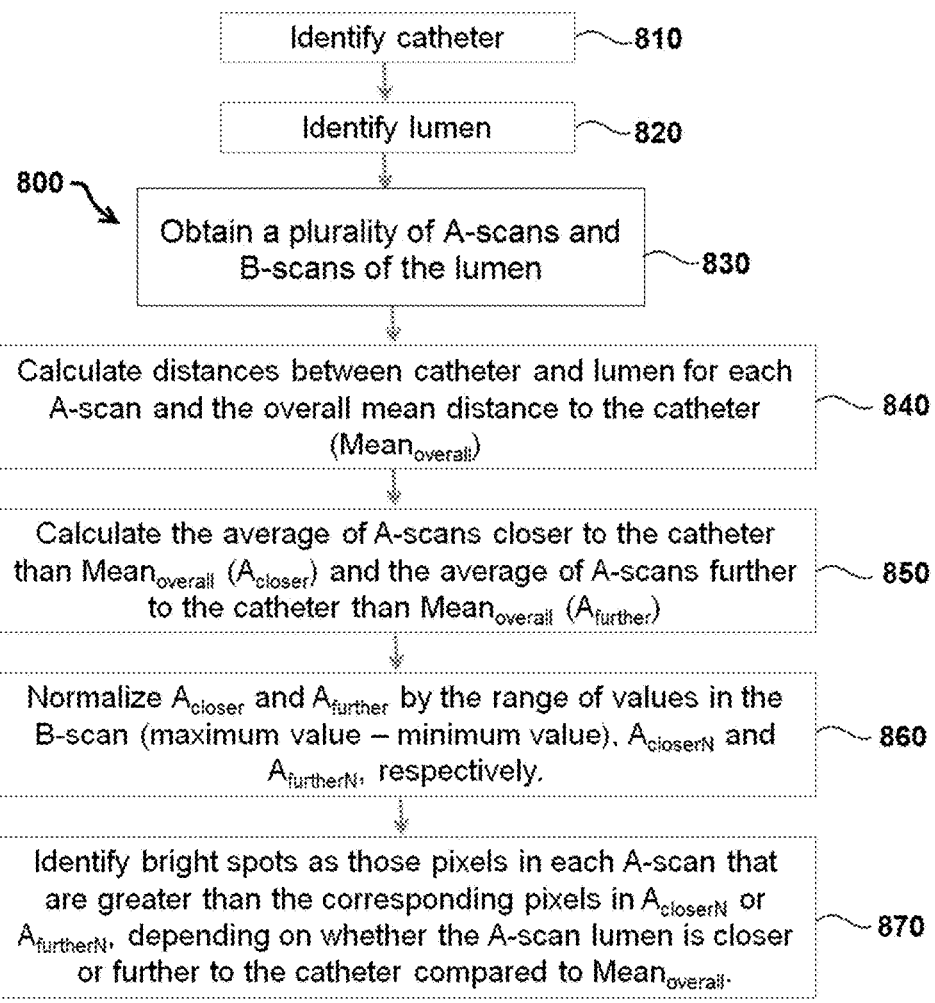
FIG. 15 shows a flowchart of steps performed by a computer readable medium to modify the display of data results according to an exemplary embodiment.
Figure 16:
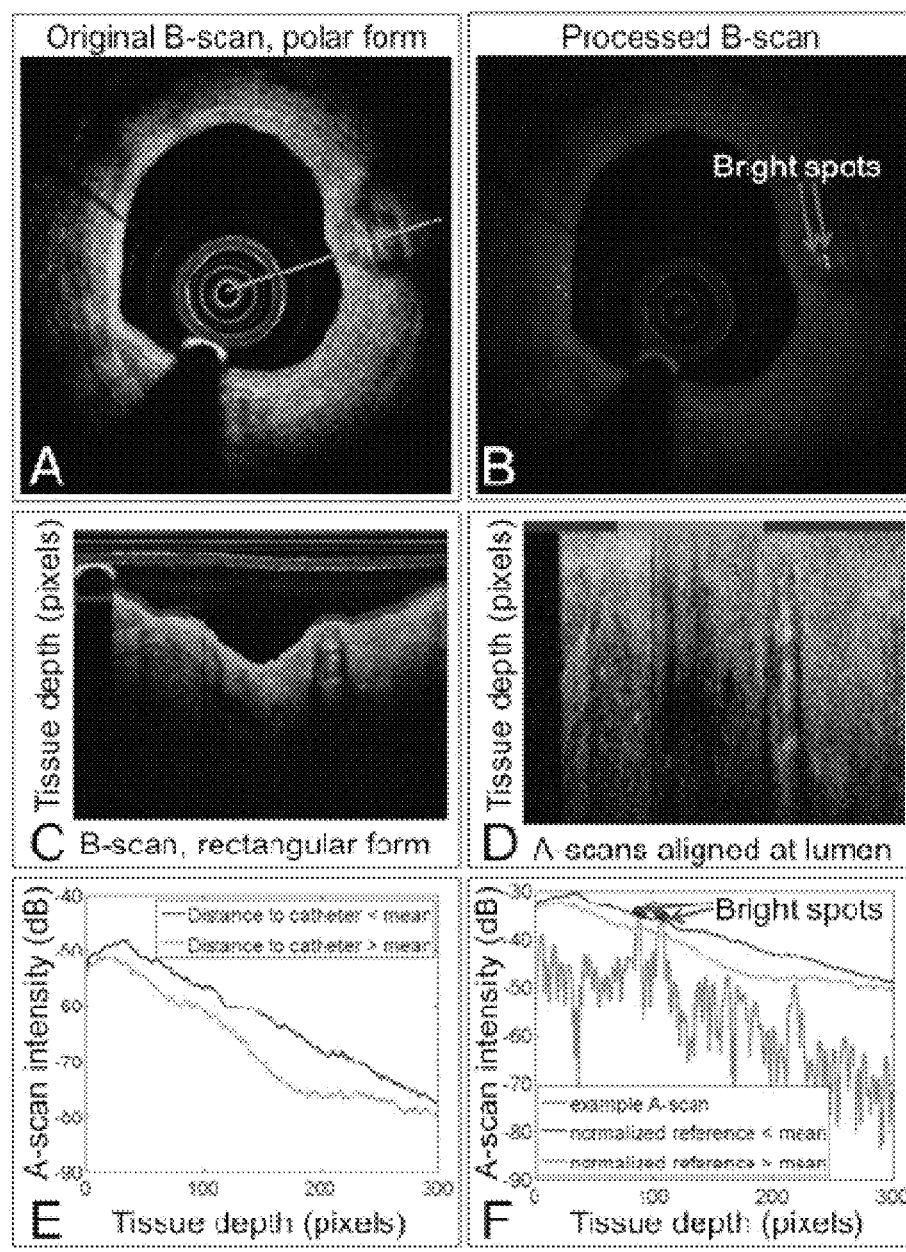
FIG. 16 shows an image and data obtained from an apparatus according to an exemplary embodiment.

Referring now to FIGS. 15-16, in one embodiment a computer readable medium can be configured to perform the following steps of a process 800: (1) identify the catheter in step 810; (2) identify the lumen (e.g. the vascular wall of the tissue being analyzed) in step 820; (3) obtain a plurality of A-scans and B-scans of the lumen in step 830; (4) calculate distances between the catheter and the lumen for each A-scan and the overall mean distance to the catheter ($Mean_{overall}$) in step 840; (5) calculate the average of A-scans closer to the catheter than $Mean_{overall}$ ($A_{closer}$) and the average of A-scans further to the catheter than $Mean_{overall}$ ($A_{further}$) in step 850; (6) normalize $A_{closer}$ and $A_{further}$ by the range of values in a B-scan (maximum value–minimum value), $A_{closerN}$ and $A_{furtherN}$ respectively in step 860; and (7) identify bright spots as those pixels in each A-scan that are greater than the corresponding pixels in $A_{closerN}$ or $A_{furtherN}$, depending on whether the A-scan lumen is closer or further to the catheter compared to $Mean_{overall}$. Additionally, performing the averaging of A-scans to identify bright spots can be replaced by scaling each A-scan by the Gaussian shape of the catheter beam to correct for intensity vs. depth.

Referring specifically now to FIG. 16A, an unprocessed image is shown in comparison to a processed image in FIG. 16B. In FIG. 16C, a B-scan image is shown in rectangular form. It can be noted that the portion of the B-scan highlighted with a blue indication line are taken from locations with a distance between the catheter and lumen wall that is less than the mean distance. Likewise, the portion of the B-scan highlighted with a green indication line is taken from locations with a distance between the catheter and lumen wall that is greater than the mean distance. FIG. 16D shows the A-scans aligned at the lumen. FIG. 16F shows an example A-scan (in magenta) as well as normalized reference values for those locations where the distance between the catheter and lumen wall that is less than the mean distance (in blue) and greater than the mean distance (in green).

The locations where the example scan in FIG. 16F exceed the normalized values can be identified as "bright spots" and the image enhanced as shown in FIG. 16B. This can allow a user to more objectively identify sites of interest of the lumen that can be further investigated. For example, certain exemplary embodiments can be configured to analyze a spatial pattern of the bright spots. Particular embodiments can be configured to analyze location depths of a plurality of bright spots, where the location depth of each bright spot is measured from a surface of the lumen to a location of the bright spot.

Specific embodiments can also be configured to document a clinically relevant outcome based on the spatial pattern of bright spots and/or the location depths of the plurality of bright spots. Non-limiting examples of clinically relevant outcomes, include for example, differences in atherosclerosis or likelihood of myocardial infarction based on gender or lifestyle factors (e.g. diet, exercise, etc.). Other non-limiting examples of clinically relevant outcomes can include the effects of changes in bright spot patterns or depths over time, and/or the presence or absence of bright spots to link different heart rhythms to different types of atherosclerosis or likelihood of myocardial infarction.

Exemplary embodiments are also capable of performing texture analysis. The dataset can be analyzed during three-dimensional rendering or processing to provide additional information to the doctor such as plaque locations, tissue type, and other physiological information. This information may be computed from the three-dimensional dataset using texture analysis, ray tracing, or other advanced processing techniques.

Exemplary embodiments of angle-resolved OCT systems may produce multiple three-dimensional datasets, in which case analysis would be done on all datasets and may or may not be combined to provide additional information to the doctor.

In summary, the combined OCT-TPL imaging system described herein can provide two optical contrast mechanisms: backscattering strength and two-photon luminescence. Embodiments of the catheter-based apparatus described herein may be utilized for light-based modalities that require the simultaneous single-mode delivery of both high peak power short-pulsed laser light and broadband light such as that utilized for OCT. Exemplary embodiments of the present disclosure combine IVOCT with TPL imaging in a catheter-based OCT-TPL imaging system to simultaneously image thin-cap fibroatheromas and their cellular components (e.g., macrophage, collagen/elastin fiber, lipid droplet) in vivo, which will have decided advantages over IVOCT alone and will provide cardiologists important information about the vulnerability of thin-cap fibroatheromas overtime during cardiovascular interventions. Specific configurations, features and methods of particular embodiments are set forth in the examples provided below.

Example 1

IVOCT Bright Spot Quantification and Analysis

It is hypothesized that bright spots in intravascular optical coherence tomography (IVOCT) images may originate by co-localization of plaque materials of differing indices of refraction (IR). To quantitatively identify bright spots, an algorithm according to the present disclosure was developed that accounts for factors including tissue depth, distance from light source, and signal-to-noise ratio. This algorithm was used to perform a bright spot analysis of IVOCT images, and to compare these results with histologic examination of matching tissue sections Although bright spots are thought to represent macrophages in IVOCT images, studies of alternative etiologies have not been reported.

Fresh human coronary arteries (n=14 from 10 hearts) were imaged with IVOCT in a mock catheterization laboratory then processed for histologic analysis. The quantitative bright spot algorithm was applied to all images.

Results are reported for 1599 IVOCT images co-registered with histology. Macrophages alone were responsible for only 23% of the bright-spot positive regions, though they were present in 57% of bright-spot positive regions. Additional etiologies for bright spots included: cellular fibrous tissue (8%), interfaces between calcium and fibrous tissue (10%), calcium and lipid (5%), and fibrous cap and lipid pool (3%). Additionally, it was shown that large pools of macrophages in CD68 histology sections correspond to dark regions in comparative IVOCT images; this is due to the fact that a pool of lipid-rich macrophages will have the same index of refraction as a pool of lipid and thus will not cause bright spots.

It is concluded that bright spots in IVOCT images are correlated to a variety of plaque components that cause sharp changes in the index of refraction. Algorithms that incorporate these correlations may be developed to improve the identification of some types of vulnerable plaque and allow standardization of IVOCT image interpretation.

IVOCT is the highest resolution technique available to image vulnerable plaque in coronary arteries [82]. In 2003, Tearney and colleagues published a quantitative study that demonstrated bright spots in IVOCT images could represent macrophages [83]. They showed that regions with an increased normalized standard deviation (NSD) correlated with areas in human aortic plaque that stained positively for macrophages in immunohistochemical studies. These findings were used to interpret subsequent clinical and animal IVOCT studies [84-88]. However, the finding that macrophages cause increased NSD has not been validated histologically by other research groups [89].

Concerns have been raised about the specificity of bright spots in identifying macrophages, despite the use of shadowing behind the bright spots as a secondary confirmation of macrophage identification [82]. For example, other plaque components appear to cause bright spots, including fibrin accumulations [90], neoatherosclerosis in previously placed stents [90], elastic lamina, cholesterol crystals, and microcalcifications [82, 91]. Furthermore, the NSD method was designed to be accurate only in fibrous caps and does not apply to the detection of macrophages in deeper arterial structures [83].

Tearney proposed that regions of high NSD represent areas in which the optical index of refraction (IR) has a higher heterogeneity; macrophages appear as bright spots because of the difference in IR between them and the surrounding fibrous tissue [83]. Using this hypothesis, it is proposed that bright spots can arise from constituents other than macrophages in which a sharp change in IR occurs at interfaces between plaque components. This sharp change in IR occurs in multiple scenarios: lipid [IR 1.33] mixed with calcified cores [IR 1.65], lipid mixed with fibrous tissue [IR 1.47], and cellular fibrous tissue rich in proteoglycans [IR 1.33]—each of which may generate bright spots in IVOCT images based on this hypothesis.

An algorithm according to the present disclosure was developed that can be applied to the entire depth of the artery to enable quantitative identification of bright spots in IVOCT images of human atherosclerotic plaque. In the present study, this algorithm was used to analyze bright spots in images of human atherosclerotic plaque and compared these results to corresponding histologic sections. In addition, the hypothesis that abrupt changes in plaque components of differing IR result in the generation of bright spots in IVOCT images was further examined.

Methods

Specimens.

10 human hearts (from 3 women and 7 men) at autopsy within 24 hours of death were examined. The average age at death was 65±11 years. The cause of death was cardiac in 6 cases. 14 coronary arteries were imaged (n=10, left anterior descending artery [LAD]; n=4 right coronary artery [RCA]). The IRB at the University of Texas approved this study.

Imaging Procedure.

The human heart catheterization laboratory was recreated with a custom IVOCT system (Volcano Corporation, San Diego, Calif.) to access the raw signal data. The IVOCT system has a 1310 nm swept source laser (HSL-1000, Santec, Hackensack, N.J.) and a bandwidth of 80 nm scanning at a repetition rate of 34 kHz. The measured free-space axial resolution was 20 µm with a 2.8 mm scan depth. The IVOCT signal was sampled with a linear k-space clock to allow real-time OCT image acquisition and display. A fluoroscopy system (GE Medical Systems) and a chamber designed to maintain the tissue at 37° C. were used. Left and right coronary 6F guide catheters were sewn into the coronary ostia, 0.014 inch guide-wire access to the coronary arteries was gained under fluoroscopic guidance, and a stent was deployed 80 mm from the guide catheter tip as a fiduciary marker. IVOCT pullbacks were acquired from the stent to the guide catheter (80 mm total pullback length). The LAD and RCA were imaged. Following imaging, the RCA and LAD were perfusion-fixed with formalin at 100 mm Hg. The left circumflex artery was not imaged due to its tortuosity in the ex vivo heart.

Histology.

The LADs and RCAs were perfusion-fixed with 10% neutral-buffered formalin, excised from each heart, individually radiographed on a Faxitron MX-20 (Faxitron Bioptics LLC, Tucson Ariz.), and decalcified overnight with Cal-Rite (Richard Allen Scientific) if necessary. The arterial segments were sliced into 2-3 mm—thick rings and further processed on a Tissue-Tek Vacuum Infiltration Processor (Sakura Finetek USA, Torrance, Calif.) for standard paraffin-embedded sections. An average of 25 rings was generated from each artery. Serial tissue sections (5 µm thick) were cut at 150-µm intervals and stained with hematoxylin and eosin (H&E), modified Movat's pentachrome, and Von Kossa. Anti-CD68 (Dako North America, Inc, Carpinteria, Calif.) and anti-a-smooth muscle cell-actin (Sigma-Aldrich, St. Louis, Mo.) antibodies were used in immunohistochemical studies to identify macrophages and smooth muscle cells, respectively.

IVOCT and Histology Co-Registration.

Each histologic ring was matched to a respective IVOCT frame. Co-registration was performed between IVOCT images and histological sections based on the following: (1) 2 fiducial landmarks—a stent deployed at the distal end of the pullback and the sewn-in guide catheter at the proximal edge—that were visible in IVOCT images, fluoroscopy, and radiography before histopathological processing, and (2) the physical position of IVOCT images in the pullbacks measured against the estimated distance in microns from the fiducial landmarks in the tissue sections. Additionally, anatomical landmarks (e.g., arterial branches or calcification patterns when present) and luminal geometric features further aided co-registration. Two researchers independently co-registered the IVOCT images and histology, discrepancies were discussed to find agreement between both co-registrations.

In IVOCT images, bright bands <65 µm thick that covered diffusely shadowed regions were identified as TCFAs. Histologic TCFAs were identified by fibrous caps <65 µm thick that covered lipid or necrotic cores.

Histologic Composition of Bright Spot-Containing Areas.

Regions within the arterial wall that elicit bright spots after application of the algorithm were first categorized by whether macrophages were present or not. Next each of these macrophage-positive or macrophage-negative bright spot sources were classified into the following 4 broad categories: (1) hypocellular or acellular collagen-rich fibrous tissue (mesh-like collagen-rich areas mixed with lipid, or the fibrous cap of fibrocalcific plaques); (2) cellular fibrous tissue (as found in intimal thickening or early lesions with high smooth muscle and proteoglycan content); (3) cholesterol clefts within necrotic cores; and (4) areas of layering or interface (as observed in remodeled plaque ruptures; at the interfaces between calcium and surrounding tissue; between lipid and calcium in fibrocalcific plaques; at the interface of necrotic or lipid cores and the overlying fibrous cap; at neovascularization sites and the media; or at the elastic lamina intimal/medial or medial/adventitial interface).

Bright Spot Quantitative Detection.

The detection method is outlined in FIG. 16. First, the distance was measured between the lumen edge and the catheter for each A-scan per frame. Next, the mean of those distances was calculated for each frame. To account for variations in signal intensity that occur as the catheter moves closer or further away from the lumen, 2 reference A-scans were calculated by averaging all A-scans that were less than or greater than the mean distance to the catheter. Then, to account for varying SNR, the reference A-scans were normalized (divided by the difference between the maximum and minimum values of each frame). Each A-scan was compared to the averaged and normalized reference A-scan that corresponded to whether its catheter to lumen edge distance was less than or greater than the mean; this provided a threshold to identify bright spots based on tissue depth, distance from catheter, and SNR of the IVOCT system and catheter.

Statistics.

Four statistical analyses were performed: 1) inter and intra-observer variability between two expert IVOCT readers who evaluated the unprocessed IVOCT frames for identification of bright spots, 2) joint probability of agreement between one expert IVOCT reader and the bright spot algorithm, 3) sensitivity and specificity of one expert IVOCT reader for identifying macrophages compared to the gold standard of histology, and 4) sensitivity and specificity of the bright spot algorithm for identifying macrophages compared to the gold standard of histology. Sensitivity and specificity calculations were performed at two depths, superficial (<100 µm) and deep (>100 µm).

Results 14 coronary arteries were imaged (n=10, LAD; n=4, RCA) from 10 human hearts, generating 300 IVOCT images per vessel. After application of the algorithm, a total of 2206 IVOCT frames with bright spots were observed. 1111 of the IVOCT frames with bright spots were co-registered with histology, and 1700 regions within these 1111 frames caused distinct sources of bright spots. 488 IVOCT frames without bright spots were co-registered to histology for negative control. See Table 1B for the morphologic classification of the arteries. When looking at only the raw, unprocessed IVOCT frames for identification of bright spots between 2 expert IVOCT readers, intra-observer variability was 88% and inter-observer variability was 76%.

Macrophage Detection by the Bright Spot Algorithm (Table 1A and 1B).

Figure 17:
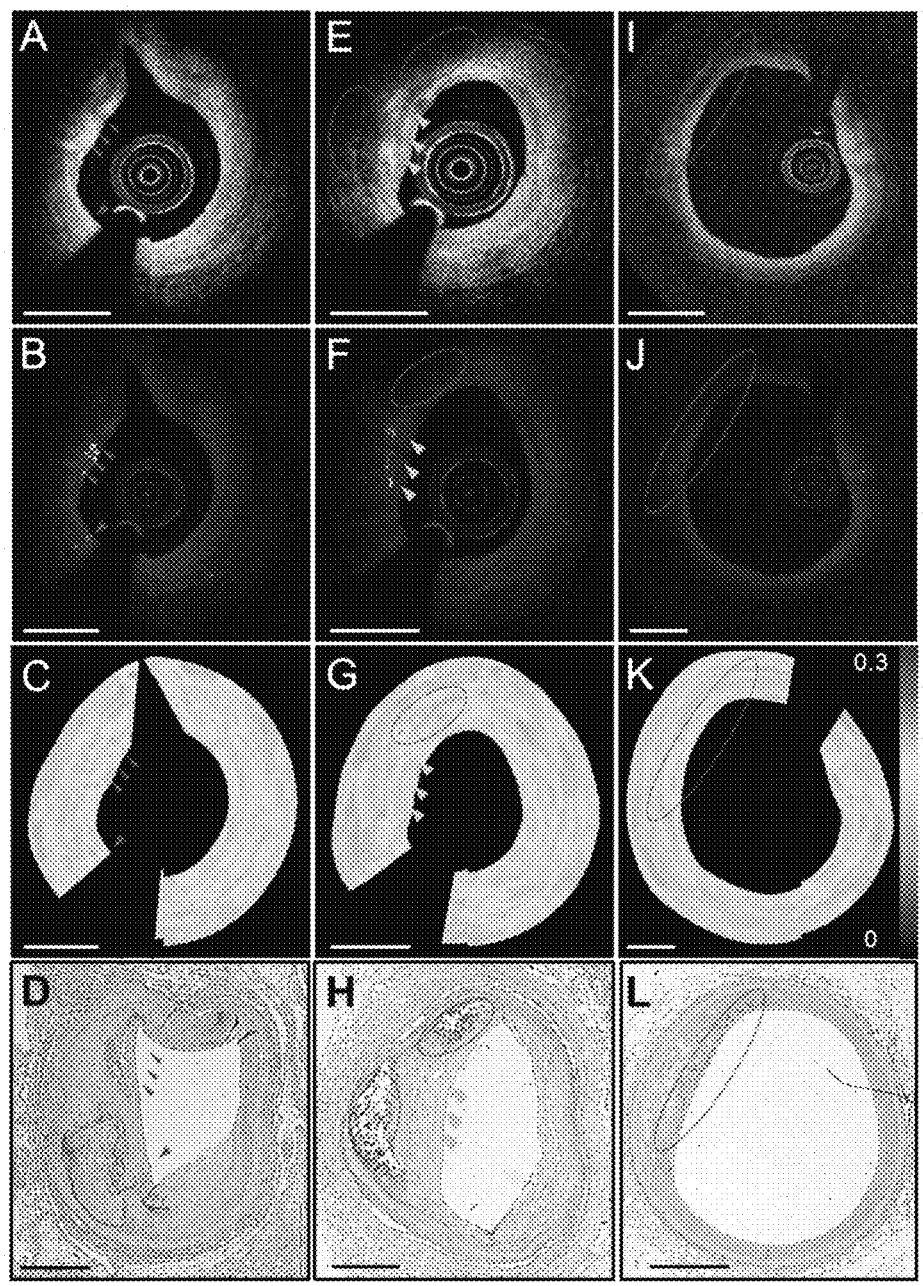
FIGS. 17-25 show images obtained from an apparatus according to an exemplary embodiment.

Using the quantitative algorithm and histologic examination, the role of macrophages in the origin of bright spots in IVOCT images were characterized (FIG. 17). As shown in Table 1A below, macrophages alone were responsible for bright spots in 391 regions (23%). A combination of macrophages and other etiologies were the source of bright spots in an additional 574 regions (34%). In total, macrophages were present in 57% of bright-spot positive regions.

TABLE 1A

Histologic composition of algorithm identified bright spots when macrophages are present.

| Bright Spot Source | N (%)* |
|---|---|
| Macrophage-rich areas with fibrous tissue | 391 (23.0) |
| Cholesterol clefts in necrotic cores | 16 (0.9) |
| Areas of layering or interface | |
| Interface of old and new fibrous tissue | 25 (1.5) |
| Intimal/medial or adventitial/medial interface | 39 (2.3) |
| Calcium/fibrous interface | 130 (7.6) |
| Calcium/lipid interface | 98 (5.8) |
| Fibrous cap/lipid pool interface | 219 (12.9) |
| Neovascularization/media interface | 48 (2.8) |

*Data are given as percentage of total bright spot regions in all IVOCT images (N = 1700).

The histologic sections from the arteries were independently evaluated by 2 pathologists and were categorized into 5 morphologic subtypes, as outlined by the modified AHA classification [110]: diffuse intimal thickening (DIT), pathological intimal thickening (PIT), fibroatheroma (FA), thin-capped fibroatheroma (TCFA), and fibrocalcific (FC) lesions. The morphologic distribution of the histologic sections is shown in Table 1B below, categorized by source of algorithm identified bright spots.

TABLE 1B

Histologic composition of algorithm identified bright spots

| | DIT | PIT | FA | TCFA | FC |
|---|---|---|---|---|---|
| Bright spots co-localized with macrophages | | | | | |
| Macrophage-rich areas with fibrous tissue | 14 | 109 | 170 | 61 | 37 |
| Cholesterol clefts in necrotic cores | 0 | 0 | 12 | 4 | 0 |
| Areas of layering or interface | | | | | |
| Interface of old and new fibrous tissue | 1 | 5 | 13 | 6 | 0 |
| Intimal/medial or adventitial/medial interface | 0 | 17 | 8 | 6 | 8 |
| Calcium/fibrous interface | 0 | 20 | 64 | 11 | 35 |
| Calcium/lipid interface | 0 | 10 | 52 | 19 | 17 |

TABLE 1B-continued

Histologic composition of algorithm identified bright spots

|  | DIT | PIT | FA | TCFA | FC |
|---|---|---|---|---|---|
| Fibrous cap/lipid pool interface | 0 | 20 | 140 | 51 | 8 |
| Neovascularization/media interface | 0 | 7 | 28 | 6 | 7 |
| Bright spots not co-localized with macrophages |  |  |  |  |  |
| Fibrous tissue |  |  |  |  |  |
| Hypocellular or acellular | 4 | 63 | 13 | 3 | 58 |
| Cellular | 65 | 42 | 15 | 0 | 16 |
| Cholesterol clefts in necrotic cores | 0 | 0 | 2 | 0 | 0 |
| Areas of layering or interface |  |  |  |  |  |
| Interface of old and new fibrous tissue | 0 | 32 | 11 | 0 | 18 |
| Intimal/medial or adventitial/medial interface | 6 | 49 | 17 | 0 | 18 |
| Calcium/fibrous interface | 2 | 31 | 31 | 3 | 95 |
| Calcium/lipid interface | 0 | 14 | 29 | 0 | 40 |
| Fibrous cap/lipid pool interface | 0 | 18 | 22 | 4 | 1 |
| Neovascularization/media interface | 0 | 3 | 8 | 0 | 1 |

The NSD values were computed for the CD68+ images by using the method described by Tearney for quantifying macrophage content [111]. Although the method has been histologically validated only in the fibrous cap, NSD was calculated in 500 μm×125 μm sized windows throughout the artery, as in the clinical implementation of the technique [112]. An NSD value of 0.3 estimated 10% macrophage content from the MacNeill et al. [112] study and that value was used to quantify the NSD results in the current study. Based on this assumption, values of NSD exceeding 10% identified areas of macrophages while values of NSD less than 10% indicated regions without macrophages.

The literature NSD method [111, 112] was compared to the bright spot algorithm to determine which more accurately identified regions of CD68 positivity. There were many examples where the NSD method was positive for macrophages, while the bright spot algorithm was negative and CD68 stains were also negative, indicating that the NSD method generates false positives (FIG. 17). This is because the method sets a threshold to assess bright spots, whereas the NSD method colorizes based on the relationship between NSD and the percentage of CD68+ staining [112]. Additionally, the method of the current study does not use percentage of CD68+ staining to categorize the images; instead, it uses optical features of the IVOCT images, which is a more unbiased approach.

Large, dense CD68+ areas on histology corresponded to dark regions (FIGS. 17 and 18) in the associated IVOCT image (125 of the CD68+ regions). Additionally, 61 regions were identified in which macrophages were located too deep in the tissue or too far from an eccentric catheter position to be visualized by IVOCT (FIG. 17I). There were also 89 regions of CD68 positivity in histologic sections that did not cause bright spots and thus were not identified by the bright spot algorithm. Lastly, in 186 regions, macrophages were depicted as bright spots that caused superficial shadowing. Of these 186, 115 (62%) were found in regions where calcium was co-localized with the macrophages (FIG. 19D) and 4 were in regions where cholesterol crystals were co-localized with the macrophages.

The sensitivity and specificity of the bright spot algorithm compared to an expert IVOCT reader for identification of macrophages with histology as a gold standard are summarized in Table 2 below.

TABLE 2

Sensitivity (SE) and specificity (SP) of the bright spot algorithm compared to an expert IVOCT reader for identification of macrophages defined by histology

|  | Algorithm | | Expert Reader | |
|---|---|---|---|---|
| Macrophage Locations | SE (%) | SP (%) | SE (%) | SP (%) |
| All | 80 | 49 | 46 | 76 |
| Superficial (<100 μm) | 74 | 49 | 42 | 76 |
| Deep (>100 μm) | 87 | 49 | 52 | 76 |

The IVOCT reader used unprocessed IVOCT images for the analysis. The algorithm was more sensitive to bright spots (80%), implying that the presence of macrophages was more often correctly identified by the algorithm than by an expert reader; but less specific (49%), as anticipated since the algorithm detects sources of bright spots due to etiologies other than macrophages. This is also supported by the joint probability of agreement that was calculated between the algorithm and the expert reader (53%), which reflects the fact that the algorithm identified regions of macrophages that the expert IVOCT reader would have missed.

The histologic composition of algorithm identified bright spots when macrophages are not present is shown below in Table 3.

TABLE 3

Histologic composition of algorithm identified bright spots when macrophages are not present.

| Bright Spot Source | N (%)* |
|---|---|
| Fibrous tissue | |
| Hypocellular or acellular | 141 (8.3) |
| Cellular | 138 (8.1) |
| Cholesterol clefts in necrotic cores | 2 (0.1) |
| Areas of layering or interface | |
| Interface of old and new fibrous tissue | 61 (3.6) |
| Intimal/medial or adventitial/medial interface | 90 (5.3) |
| Calcium/fibrous interface | 162 (9.5) |
| Calcium/lipid interface | 83 (4.9) |
| Fibrous cap/lipid pool interface | 45 (2.6) |
| Neovascularization/media interface | 12 (0.7) |

*Data are given as percentage of total bright spot regions in all IVOCT images (N = 1700).

Bright spots were also associated with fibrous tissue (cellular: 8%; FIG. 20G, acellular: 8%); areas of plaque layering between old and new fibrous tissue in remodeled plaques (4%; FIG. 20A); calcified lipid cores with non-calcified remaining lipid (5%; FIG. 19A); and the fibrous cap and lipid pool interface (3%; FIG. 20D).

The histologic composition of algorithm identified bright spots in TCFA when macrophages are present is shown in Table 4 below.

TABLE 4

Histologic composition of algorithm identified bright spots in TCFA when macrophages are present.

| Bright Spot Source | N (%)* |
|---|---|
| Macrophage-rich areas with fibrous tissue | 51 (31) |
| Cholesterol clefts in necrotic cores | 4 (2) |
| Areas of layering or interface | |
| Interface of old and new fibrous tissue | 6 (4) |
| Intimal/medial or adventitial/medial interface | 9 (5) |
| Calcium/fibrous interface | 13 (8) |
| Calcium/lipid interface | 19 (12) |
| Fibrous cap/lipid pool interface | 54 (33) |
| Neovascularization/media interface | 9 (5) |

*Data are given as percentage of total regions in IVOCT images with bright spots that are co-localized with CD68 positivity (N = 165).

Figure 21:
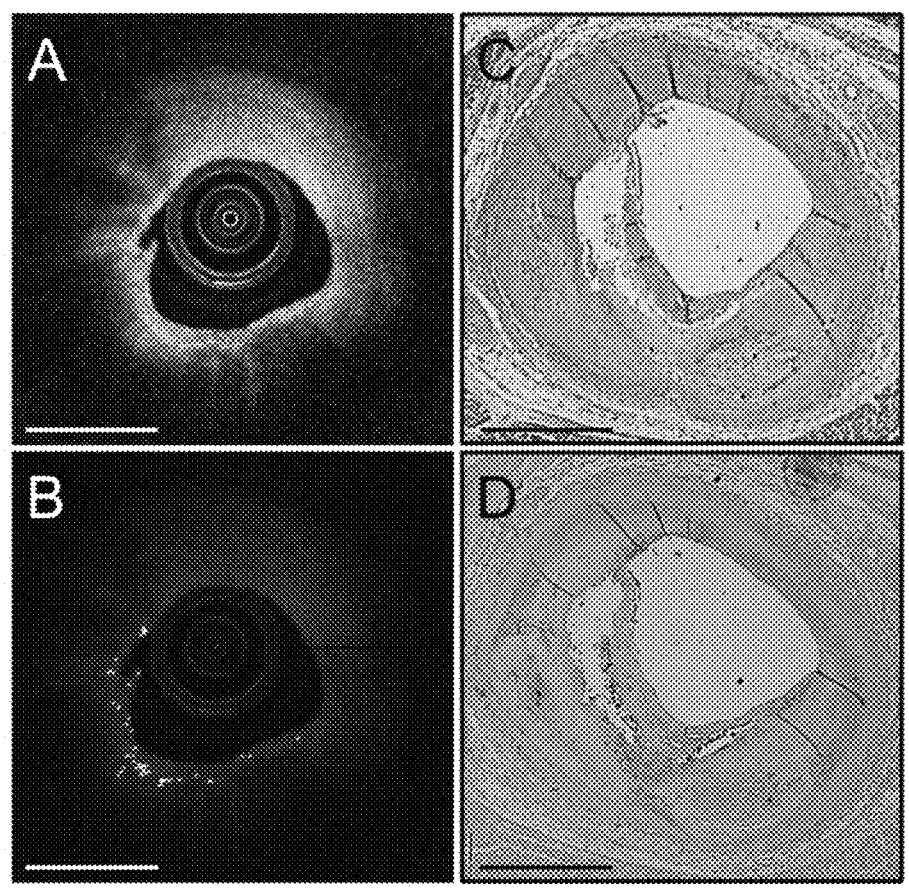

Bright spots occurred in N=175 regions of IVOCT frames morphologically classified as TCFA. Of these, 165 regions were also co-localized with CD68 positivity. FIG. 21 demonstrates bright spots originating in a TCFA; it can be observed that the bright spots in this case are caused by both macrophages in the fibrous cap and the fibrous cap interface with the lipid core. While not described in a table, there were only 10 regions of bright spots in TCFA IVOCT frames that were not co-localized with macrophages; of these regions, the source of bright spots was the fibrous cap and lipid or necrotic core interface (N=4), the fibrous cap and calcium border (N=3), and acellular fibrous tissue (N=3).

It has been confirmed that IVOCT bright spots can be caused by macrophages—however, new alternative etiologies have also been identified. These findings suggest that IVOCT bright spots can be generated in areas characterized by sharp changes in IR. The results of this study support the principle that spatial gradients in IR are responsible for enhanced light scattering that results in bright regions in IVOCT images. Thus, most bright spots in IVOCT images are not caused by macrophages, but originate from a mixture of atherosclerotic components that have maximal differences in optical IR. Of the sources of bright spots identified, all were found in regions with known sharp gradients of IR. In the case of layering between old and new fibrous tissue, the co-localization of different types of collagen fibers or the degree of maturation is responsible for the shift in IR [93]. In particular, after a rupture has healed, collagen type III is replaced by type I and results in a band of high backscattering signal between the layers of tissue—this is likely due to the greater optical density of collagen type I in comparison to type III (1).

Figure 18:
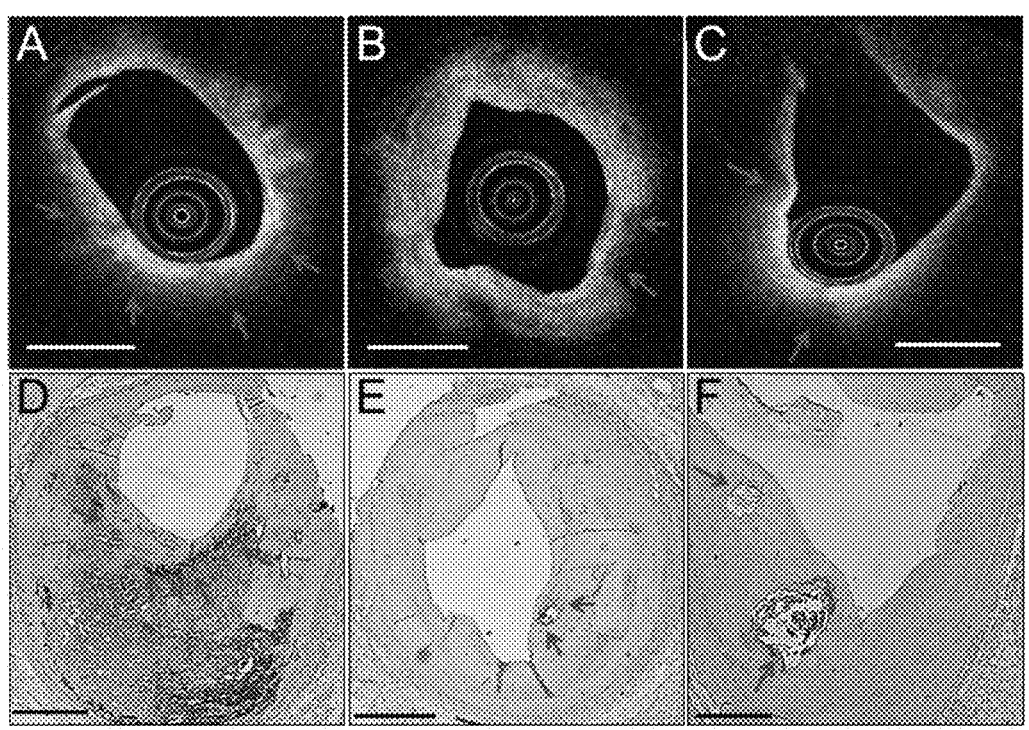

Findings that large pools of macrophages appear dark supports the observation that homogeneous material in plaque, even groups of macrophages as shown in this study, can have a homogeneous IR and, thus, would not be expected to cause bright spots. Moreover, this finding implies that a large pool of macrophages that have engulfed lipid (foam cells) will appear dark on IVOCT images, similar to lipid pools, and may not be easily identified by IVOCT (FIGS. 17 and 18). Thus, the juxtaposition of foam cells with a low IR next to the fibrous cap with a higher IR may have been the origin of bright spots identified in previous studies [83].

An alternative hypothesis for explaining why not all macrophages appear as bright spots in IVOCT images involves differences in macrophage subsets. M1 macrophages, considered the "classic" phenotype, are thought to be pro-inflammatory and engulf lipid to form foam cells, whereas M2 macrophages, considered anti-inflammatory, contain smaller vesicles of engulfed lipid [94] and a higher density of mitochondria [95]. Thus, M1 macrophage foam cells may appear as shadows or dark regions because of the large amount of intracellular lipid, but M2 macrophages may appear bright because of a higher density of light-scattering mitochondria [96, 97]. Further study of how M1 and M2 macrophages appear in IVOCT images is needed. Additionally, combining IVOCT with other imaging techniques that have a higher specificity for lipid, fibrous tissue and macrophages, such as two-photon luminescence [98] or fluorescence lifetime imaging [99], may provide enhanced contrast for distinguishing between the subtypes of macrophages.

While 57% of all regions with algorithm-defined bright spots were CD68[+], 34% of all regions were CD68[+] that were also co-localized with other tissue components which caused bright spots in the absence of any macrophages (see Table 3). It is uncertain whether bright spots in the presence of both macrophages and those other components were caused by the macrophages or by another etiology. Thus, only 23% of the bright spots were definitely caused by macrophages.

In addition to appearing as bright spots in IVOCT images, macrophages can cause shadowing that may appear as a lipid pool [82, 100]. Although the algorithm for identifying bright spots does not directly search for shadowing behind the bright spots, 186 regions of bright spots were identified that caused shadows; 119 were located in regions characterized by the co-localization of microcalcification or cholesterol crystals and macrophages (FIGS. 19D-F). It is believed that shadowing was actually caused by microcalcification and/or cholesterol crystals. Considering Mie scattering, which describes the way light scatters from symmetric objects, smaller features with higher IRs will cause increased shadowing. Thus, small cholesterol crystals and microcalcifications, both of which have high IRs compared with the other plaque components, can cause shadows. In addition to ingesting lipid, macrophages can engulf microcalcifications [101] and cholesterol crystals [102]. Macrophages alone do not have optical properties that would cause a shadow, unless they have engulfed a micro-calcification or plaque component that has an IR substantially higher than that of lipid. The high IR of cholesterol clefts is also consistent with the bright spots observed within necrotic cores. Thus, it is proposed that the type and distribution of engulfed material affects the shadowing by macrophages.

Most of the bright spot regions found in TCFA IVOCT frames (165 of 175 regions) were co-localized with macrophages. Interestingly, the majority were caused by either macrophage-rich areas with fibrous tissue or the fibrous cap/lipid pool interface, which is also where macrophages are often found. Thus it can be difficult to distinguish when bright spots found in TCFAs are caused by macrophages or the fibrous cap/lipid pool interface.

The algorithm was more sensitive at detecting the true presence of macrophages than an expert reader, demonstrating its value. This result is supported by the joint probability of agreement between the expert IVOCT reader and the algorithm—only 53%, which quantifies the finding that the algorithm identified regions of macrophages that the expert IVOCT reader missed. The reduced specificity of the algorithm was anticipated because it also detects other causes of bright spots than macrophages, due to differences in IR of co-mingled plaque components, the hypothesis of the paper. The increased specificity (76%) of the IVOCT reader shows that an expert reader can distinguish between bright spots caused by macrophages and bright spots caused by other sources. One way to increase the accuracy for identification of macrophages is to allow an expert reader to sort through the bright spot processed images, and disregard images that have bright spots obviously not caused by vulnerable plaque morphologies. Future advances in multi-modal or more advanced image processing methods could discard regions of brightness from non-vulnerable plaque types automatically. For example, the accuracy of identifying vulnerable plaque could be improved by combining IVOCT with a novel technique that provides biochemical specificity such as time-resolved fluorescence [103] or Raman spectroscopy [104].

It was found that regions with lipid intermingled in fibrocalcific plaque can also generate bright spots. It is believed the underlying reason for this finding is that fibrocalcific plaques show rich signal heterogeneity within the calcified cores. Lipid cores initially develop microcalcifications, which have been associated with vulnerable plaques [105]. These microcalcifications coalesce into larger calcifications; the intermingling of lipid with a low IR and microcalcifications with a high IR is responsible for the complexity and heterogeneity of some calcification sites. Once these cores become homogeneous calcified plates [106], the bright reflections may resolve. However, homogeneous calcified plates in the absence of residual pools of lipid are not frequently found in human atherosclerosis and are not commonly seen during OCT imaging.

Because current methods for interpreting IVOCT images are qualitative, interpretation varies widely. This is especially true when identifying thin-capped fibroatheroma (TCFA) because distinguishing lipid from calcium can be difficult [107-109], and macrophages can cause shadowing that falsely appears as a lipid core [100]. Developing algorithms to quantify plaque composition is critical if IVOCT is to be used for accurately identifying plaque composition. Furthermore, several optical properties must be considered when identifying IVOCT bright spots. Light attenuates through tissue at an exponential rate dependent upon both depth and tissue composition, and the intensity of light reflections varies with distance from the catheter. Finally, the signal-to-noise ratio (SNR) will vary between IVOCT images and pullbacks due to differences in the power of laser sources, manufacturing variability between catheters, and other clinical variables such as residual blood in the field. Thus, tissue depth, distance from the catheter, and the SNR are factors that should be considered when identifying IVOCT bright spots and all are taken into account with the bright spot algorithm presented here.

Conclusions

A novel quantitative technique has been developed to identify bright spots in IVOCT images. Our findings indicate that not all bright spots are caused by macrophages; rather they can be generated by a combination of plaque components that create sharp changes in the IR. Moreover, it was found that macrophage foam cells can be seen as dark regions on IVOCT images. Our study underscores the importance of developing more discerning algorithms. Software that incorporates our quantitative technique may improve the identification of some types of vulnerable plaque and may enable the standardization of IVOCT image interpretation.

Figure Legends

FIG. 16 illustrates the following: an original B-scan (A). Algorithm-processed B-scan showing the identified bright spots (B). B-scan from (A) converted to a rectangular view (C). The blue and green line marks the tissue lumen identified by the algorithm. The blue tissue edge identifies A-scans that are closer than the mean distance to the catheter; the green tissue edge identifies A-scans further than the mean distance to the catheter. Original B-scan with A-scans aligned at the blue and green line from (C) (D). Averaged A-scans from the blue and green regions in (C) (E). The intensity required to be considered a bright spot decreases with tissue depth and increases with closeness to the catheter. An example A-scan shown in magenta (A) compared to the reference value (F). Pixels with intensity greater than the reference value are marked in red and labeled as bright spots in (B). dB=decibels.

FIG. 17 illustrates the following: unprocessed IVOCT image with visible bright spots (red arrows) (A). Algorithm-processed IVOCT image with bright spots identified (B). Normalized standard deviation (NSD) image (C). CD68 stain showing that bright spots were caused by macrophages (D). Unprocessed IVOCT image with bright spots (yellow arrows) and shadows (red circles) caused by macrophages (E). Algorithm-processed IVOCT image with bright spots identified (F). NSD image (G). CD68 stain showing that bright spots came from a region of macrophage positivity and that the red circled macrophage pool was depicted as a shadow in (E) and (F) (H). Unprocessed IVOCT image from a region with macrophages far from the catheter (I). Algorithm-processed IVOCT image showing that bright spots were not found in the $CD68^+$ region (J). NSD image (K). CD68 stains showing macrophage positivity in the red circle (L); this region was too far from the catheter for the signal to identify bright spots. All scale bars are 1 mm.

FIG. 18 illustrates the following: Macrophages and macrophage shadows in IVOCT images. Unprocessed IVOCT images (A-C). CD68 stain verifying the presence of macrophages (D-F). Red arrows mark macrophage-rich regions that appear as dark IVOCT regions, not bright spots. All scale bars are 1 mm.

Figure 19:
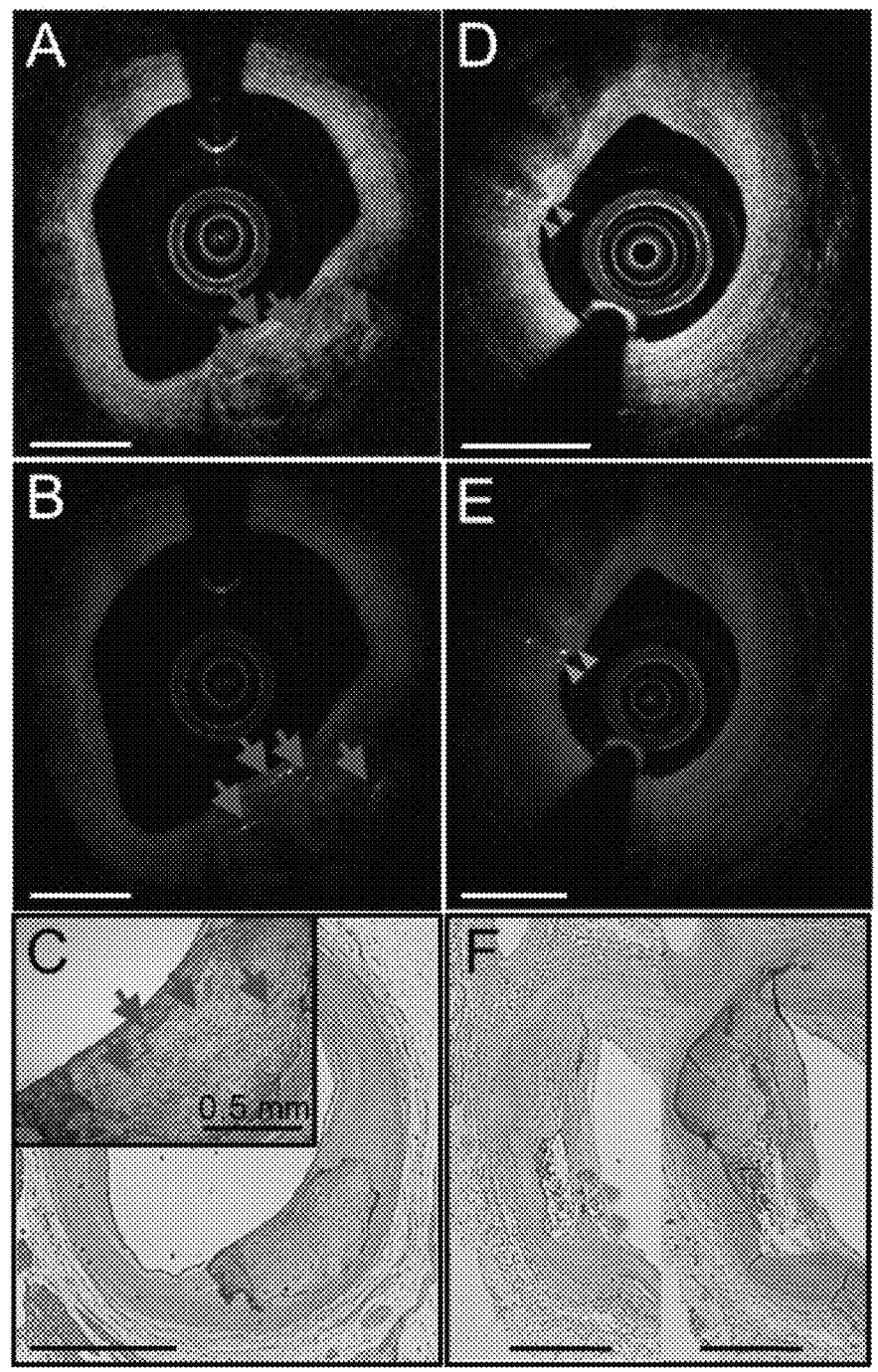

FIG. 19 illustrates the following: Unprocessed IVOCT image with bright spots caused by calcium mixed with islands of lipid (red arrows) (A). Algorithm-processed IVOCT image with bright spots identified (B). H&E stain (C). Unprocessed IVOCT image with bright spots that cause shadows like macrophages (orange arrows) (D). Algorithm-processed IVOCT image with bright spots identified (E). CD68 (left) and H&E (right) stains showing that macrophages co-mingled with calcium are the cause of the bright spots with shadowing (F). All scale bars are 1 mm unless otherwise noted.

Figure 20:
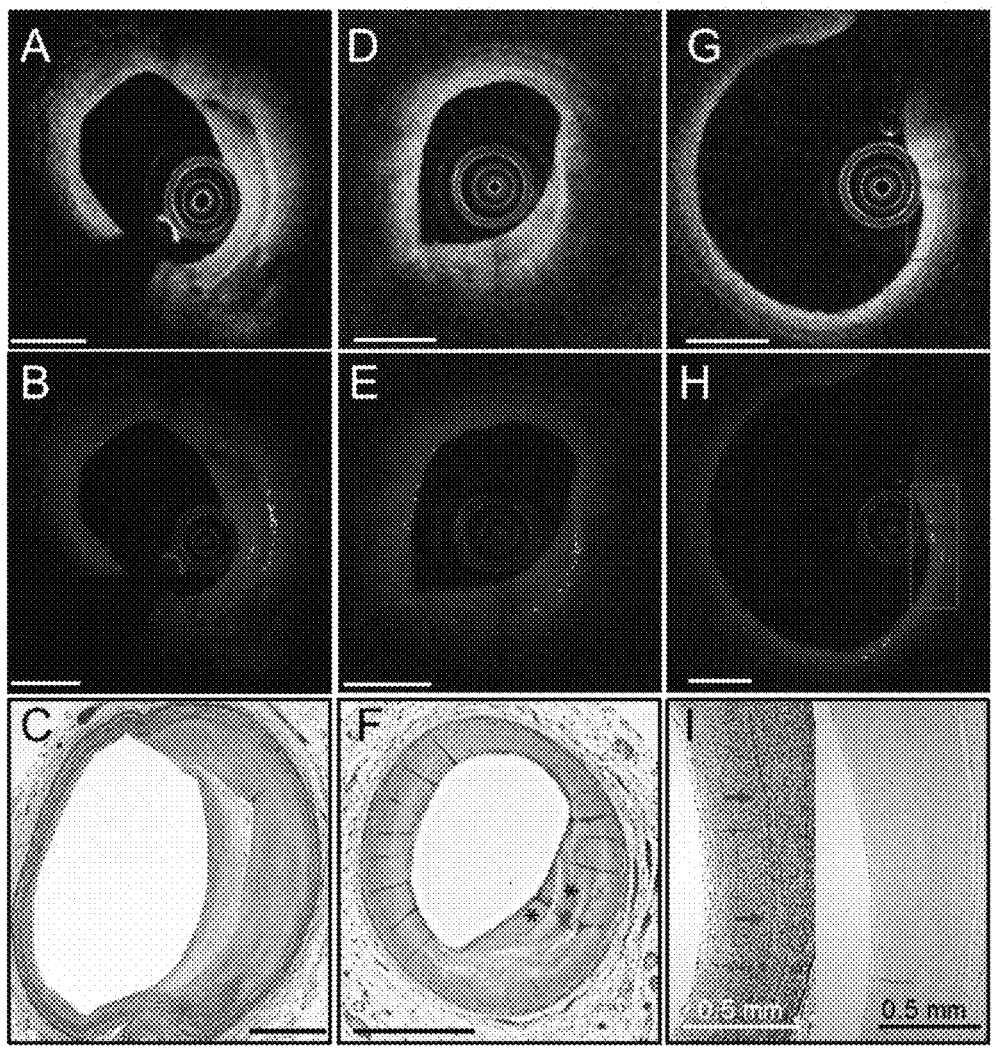

FIG. 20 illustrates the following: unprocessed IVOCT image from a region with fibrous tissue layering that generated bright spots (A). Algorithm-processed IVOCT image with bright spots identified (B). Movat's stain showing layering suggestive of a healed rupture (C). Unprocessed IVOCT image from a region with an interface between fibrous tissue and a long, narrow lipid core (D). Algorithm-processed IVOCT image with bright spots identified (E). H&E stain showing the fibrous components (asterisks) (F). The lipid core appears as a clear band. Unprocessed IVOCT image from a region of cellular fibrous intimal thickening that is rich in smooth muscle cells and proteoglycans (G).

Algorithm-processed IVOCT image with bright spots identified (H). Movat's stain (left) of the region within the inset showing elastin layers (arrows) (I); CD68 stain (right) showing that this region is CD68 negative. All scale bars are 1 mm unless otherwise noted.

FIG. 21 illustrates the following: unprocessed IVOCT image that was classified as TCFA by histology (A). Algorithm-processed IVOCT image with bright spots identified (B). H&E stain showing a TCFA (C). CD68 stain showing macrophages at the fibrous cap and lipid pool interface (D).

Example 2

A Quantitative Assessment Using Bright Spot Algorithm

Figure 26:
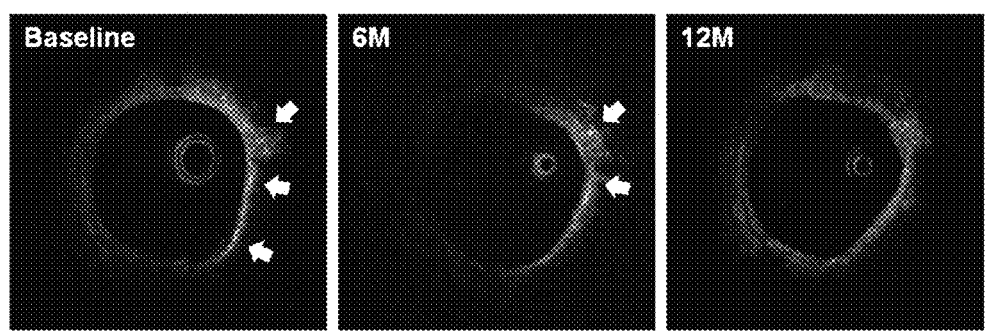
FIGS. 26-28 show images and data obtained from an apparatus according to an exemplary embodiment.
Figure 27:
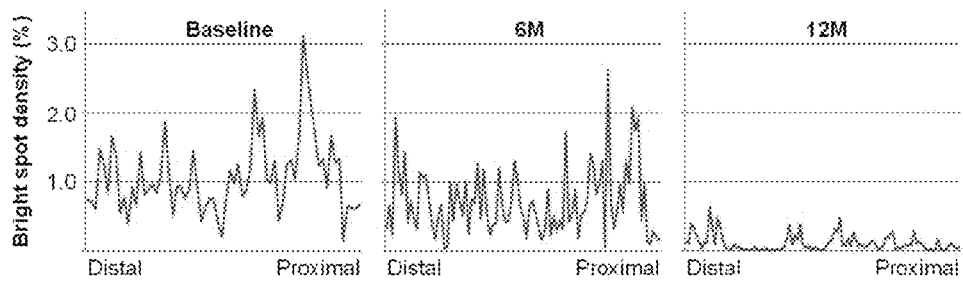

Referring now to FIGS. 26 and 27, a study was performed to evaluate the statin efficacy on the change of plaque complexity using an OCT bright spot algorithm according to the present disclosure. Recent studies using OCT have reported that statin therapy increases the thickness of fibrous caps in human coronary plaques, but the efficacy on the stabilization of plaque complexity is unknown.

Fifty-nine lipid-rich coronary plaques in non-culprit lesions from forty patients were randomized to receive statins (specifically, 60 mg atorvastatin (AT60), 10 mg rosuvastatin (RT10), or 20 mg atorvastatin (AT20)). The images and data shown in FIGS. 26 and 27 were obtained at an initial baseline, six month and twelve month time periods. An OCT algorithm was applied that is able to identify bright spots representing a variety of plaque components, including for example, macrophages. The bright spot density was measured within superficial 250 µm of the vessel wall as the number of bright pixels divided by the number of pixels in each frame through the entire plaque length.

As shown in FIGS. 26 and 27, a significant reduction in the bright spot density was observed during the twelve month time frame, and in particular between the six month and twelfth month time frames. Each of the three types of statins demonstrated noticeable reduction in bright spot density from baseline to twelfth month (−0.61% [−0.93, −0.34, P<0.001, −0.45% [−0.99, −0.34], P=0.001 and −0.41% [−0.98, −0.19], P<0.001, in AT60 [n=22], RT10 [n=15] and AT20 [n=22], respectively) without significant difference among the groups (P=0.76). There was not a significant difference in the reduction of bright spot density from baseline to twelve-month patients with acute coronary syndrome (n=47) and patients with stable angina (n=12) (−0.49% [−0.97, −0.28] vs. −0.41% [−0.89, −0.21], P=0.62).

Table 5 below shows the chronological change of bright spot density.

TABLE 5

Chronological change of bright spot density (P < 0.001 vs. index and 6M).

|  | Baseline | 6M | 12M |
|---|---|---|---|
| Bright spot density (%) | 0.57 [030-1.01] | 0.50 [0.15-1.13] | 0.02 [0.00-0.11]* |

In conclusion, coronary plaque complexity evaluated by a quantitative OCT algorithm was improved significantly by twelve-month statin therapy, irrespective of the statin type or baseline clinical presentation.

Example 3

Bright Spot Representative Images and Spatial Distribution

Figure 28:
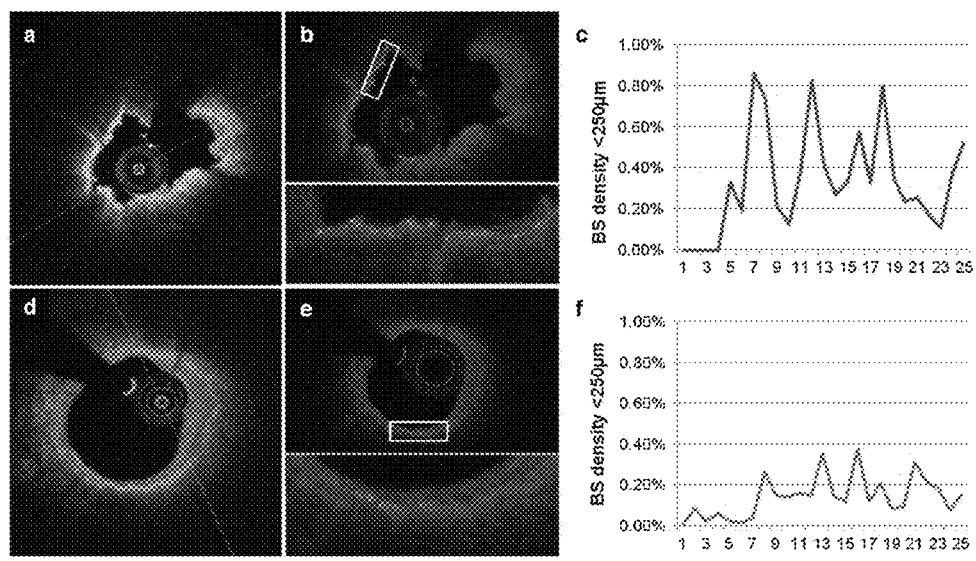

Referring now to FIG. 28, representative images and spatial distribution of bright spots are shown. Sections (a) and (b) of FIG. 28 provide representative images of specimens with acute coronary syndrome. Section (a) is a raw cross sectional OCT image, while section (b) provides a processed image using a bright spot algorithm as disclosed herein to a depth of 250 µm. The lower panel of section (b) represents the magnified image of the inset box shown in the upper panel of section (b). As shown in the figures, bright spot accumulation can be seen around the disrupted fibrous cap. A representative distribution of bright spot density within the longitudinal region of interest in a case of acute coronary syndrome is shown in section (c) of FIG. 28, with the X-axis representing the distal to proximal frame numbers.

Sections (d) and (e) of FIG. 28 provide representative images of specimens with stable angina pectoris. Again, section (d) is a raw cross sectional OCT image, while section (e) provides a processed image using a bright spot algorithm as disclosed herein to a depth of 250 µm. The lower panel of section (e) represents the magnified image of the inset box shown in the upper panel of section (e). As shown in the figures, several small bright spots can be seen. A representative distribution of bright spot density within the longitudinal region of interest in a case of stable angina is shown in section (f) of FIG. 28, with the X-axis representing the distal to proximal frame numbers.

Example 4

Catheter-Based Intensity OCT-TPL System

Examples of the catheter-based intensity OCT-TPL system (shown in FIGS. 5A and 5B) can incorporate a spectral-domain OCT system operating at 1310 nm combined with TPL using a tunable femtosecond laser excitation (e.g., 760-1040 nm, 6 nJ-5 µJ, 100 fs-1 ps, 500 kHz-80 MHz). A pulse compressor can be utilized to pre-compensate the group dispersion delay of femtosecond laser light to provide transform-limited pulses on the luminal surface. The imaging catheter is connected to a photonic crystal fiber (PCF) (e.g., LMA-20, NKT Photonics) of the OCT-TPL imaging system, which can enable single-mode propagation of both OCT light and TPL excitation light and transmission of TPL emission light (e.g. the OCT light and TPL excitation light are transmitted simultaneously). In certain embodiments, the PCF may comprise a 15 µm core (e.g., LMA-15).

Figure 5A:
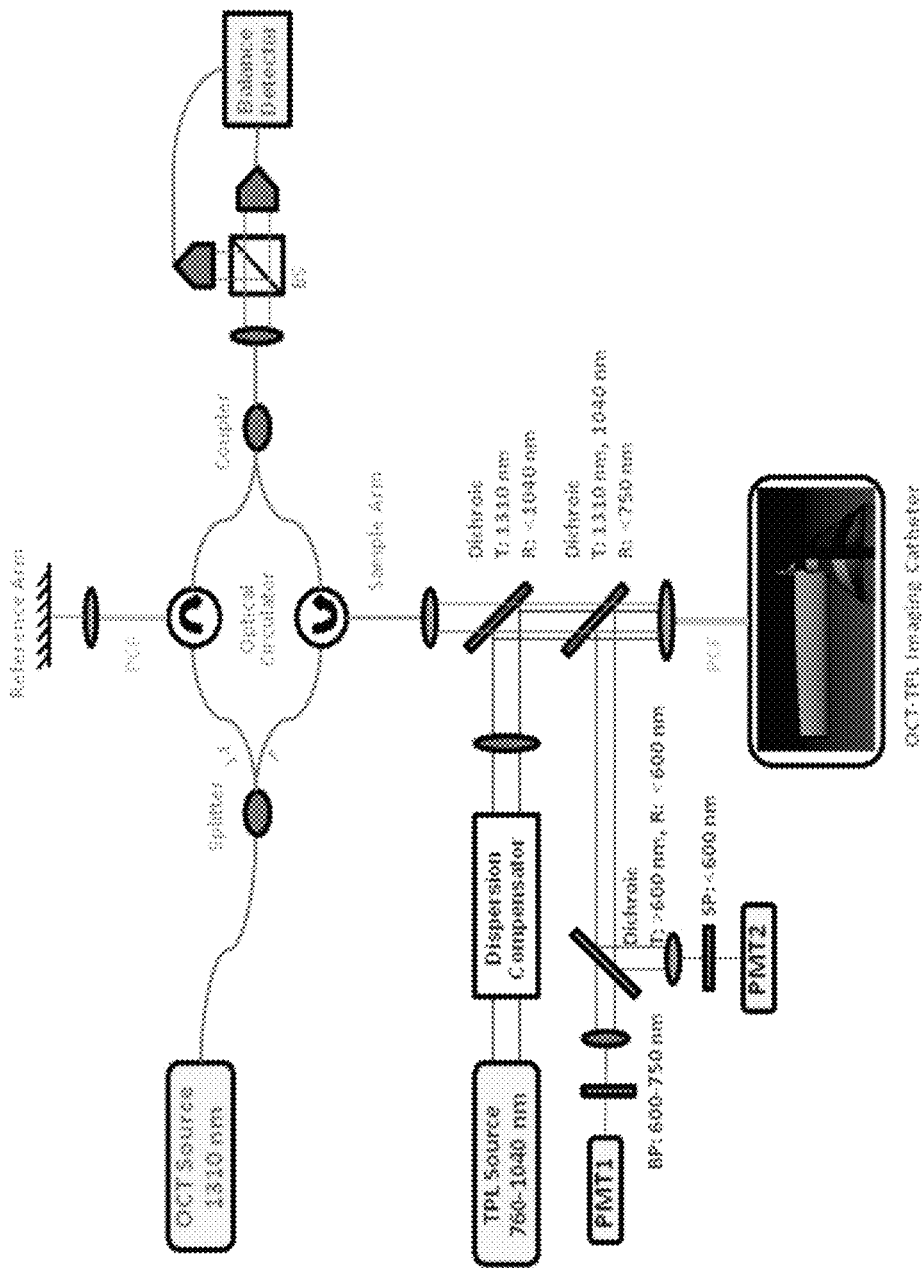
FIGS. 5A and 5B shows a schematic of an apparatus according to an exemplary embodiment.

FIG. 5A depicts a catheter-based intensity OCT-TPL imaging system comprising a beam splitter (BS); band-pass filter (BP); short-pass filter (SP); photon multiplier tube (PMT); and a photonic crystal fiber (PCF). FIG. 5A illustrates an example in which the TPL excitation light is not transmitted through the dichroic mirrors to the PCF fiber.

Figure 5B:
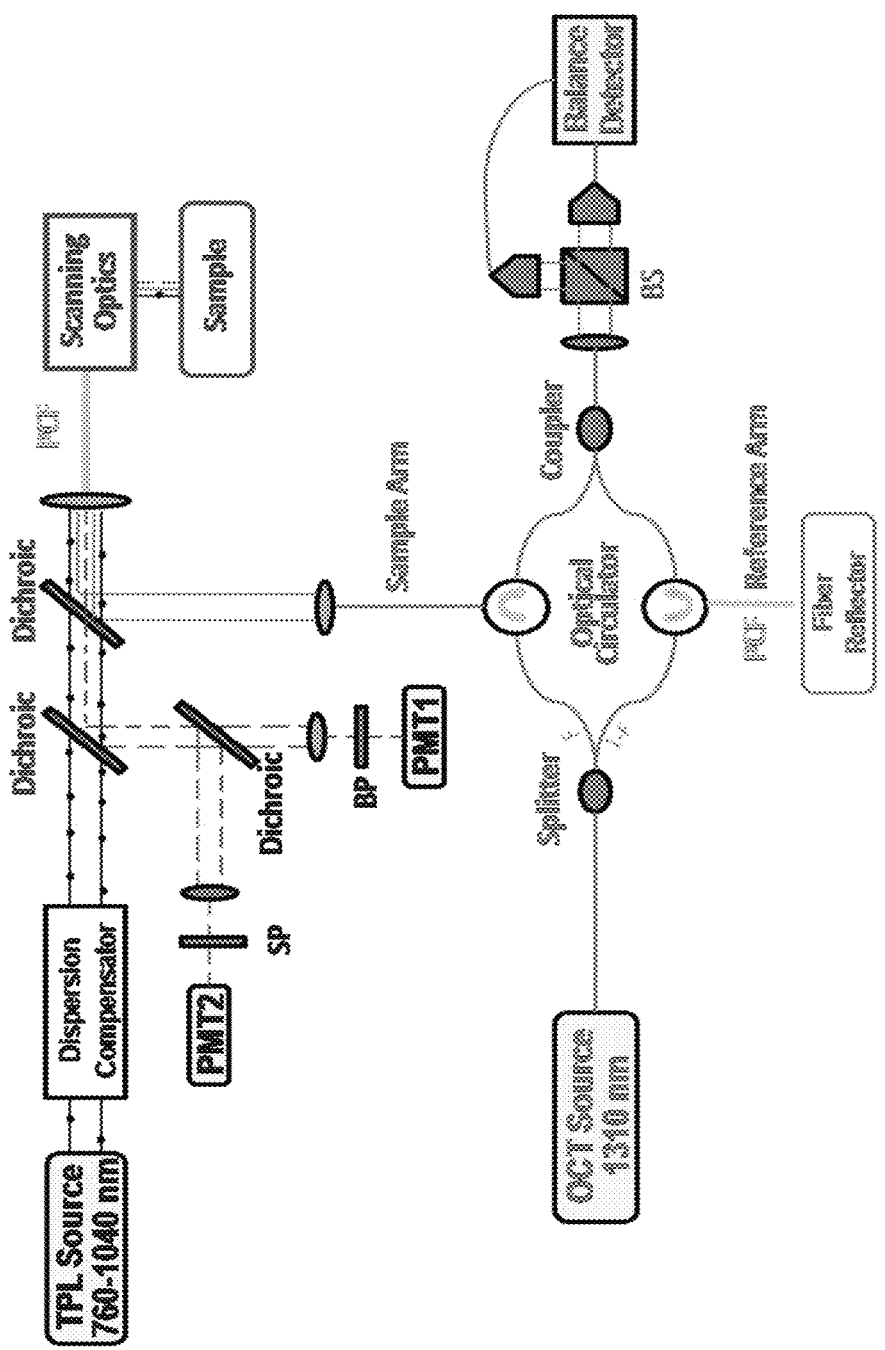
Figure 6:
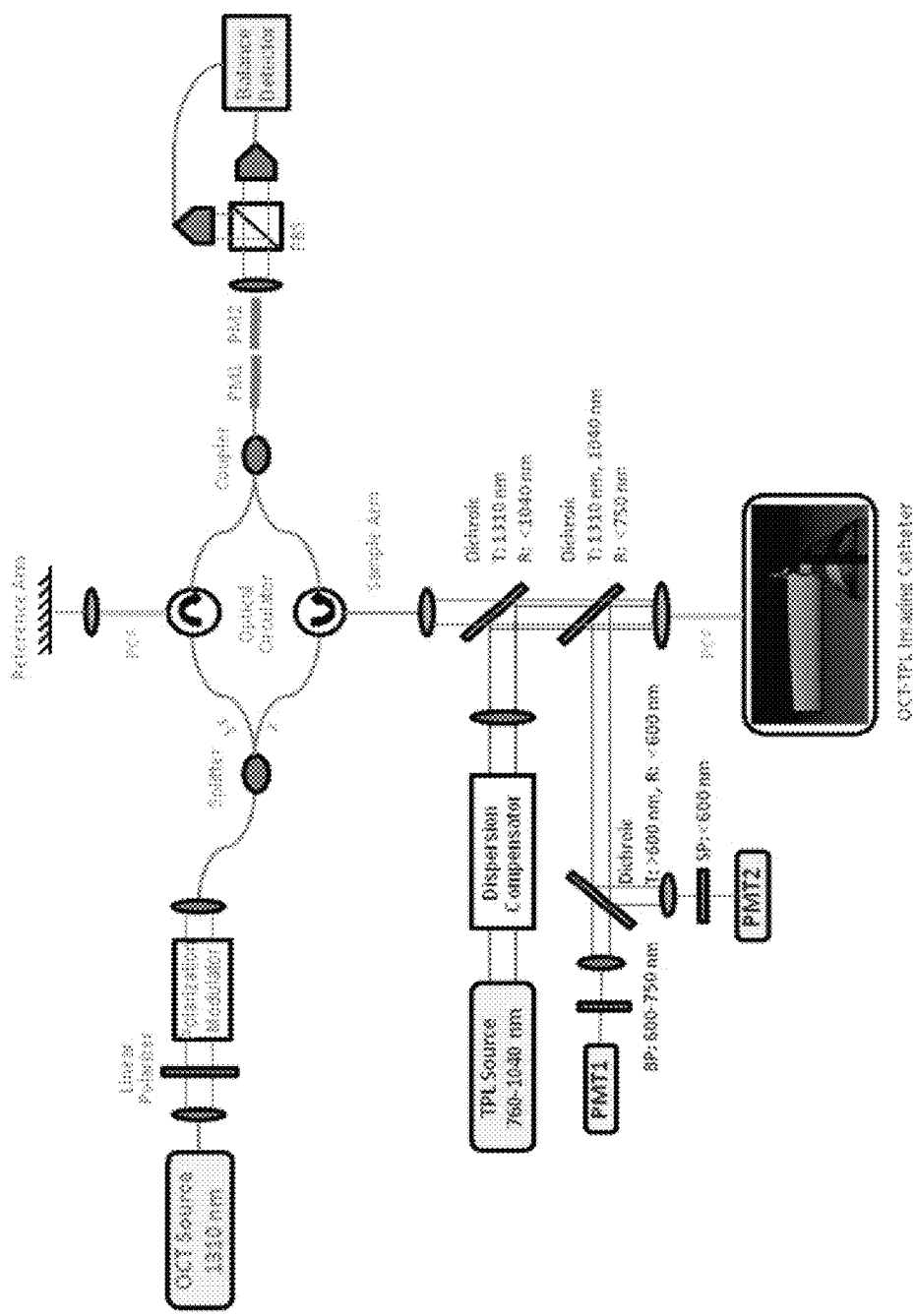
FIG. 6 shows a schematic of an apparatus according to an exemplary embodiment.
Figure 7:
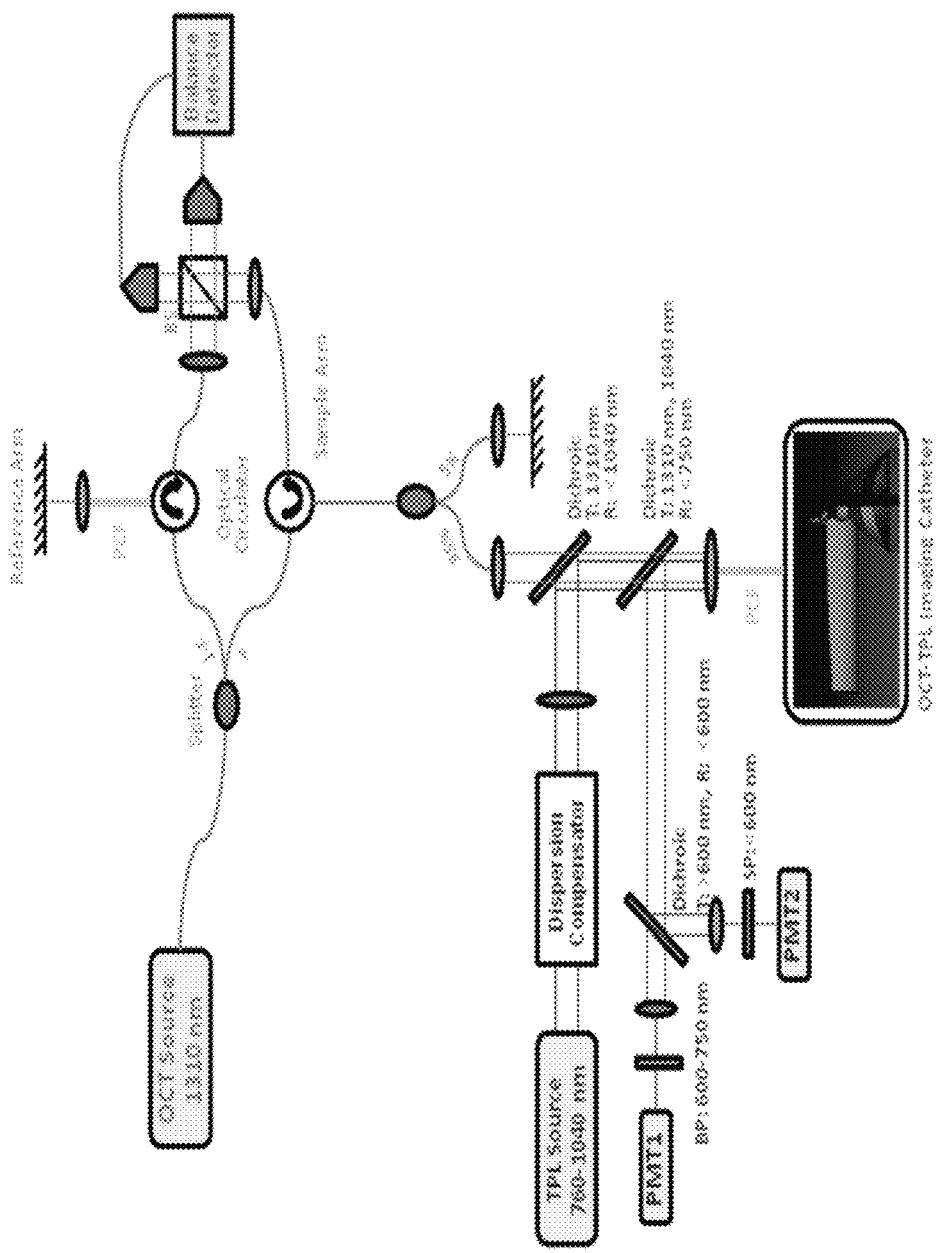
FIG. 7 shows a schematic of an apparatus according to an exemplary embodiment.

FIG. 5B also depicts a catheter-based intensity OCT-TPL imaging system comprising a beam splitter (BS); band-pass filter (BP); short-pass filter (SP); photon multiplier tube (PMT); and a photonic crystal fiber (PCF). In contrast, however, FIG. 5B illustrates an example in which a portion of the TPL excitation light is transmitted through the dichroic mirrors to the PCF fiber (and subsequently to a scanning optics module and the sample). As a result, the arrangement of the TPL and OCT light sources, as well as the associated instrumentation, is also different as shown in FIGS. 5A and 5B. In either configuration, a dispersion compensator could also be placed in OCT reference arm branch as known in the art.

Figure 22:
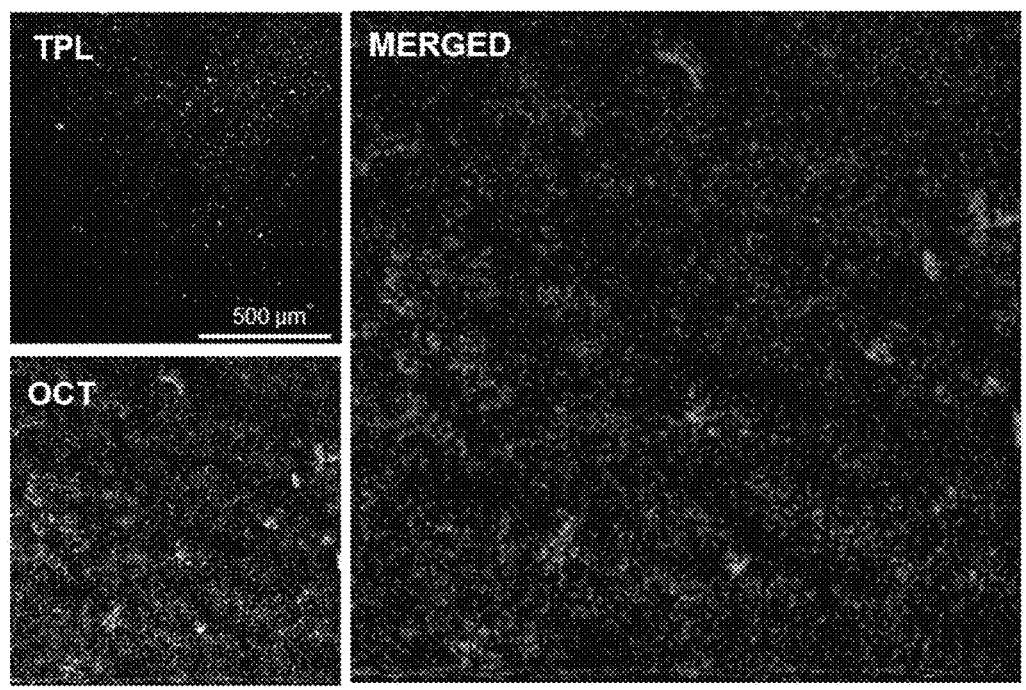
Figure 23:
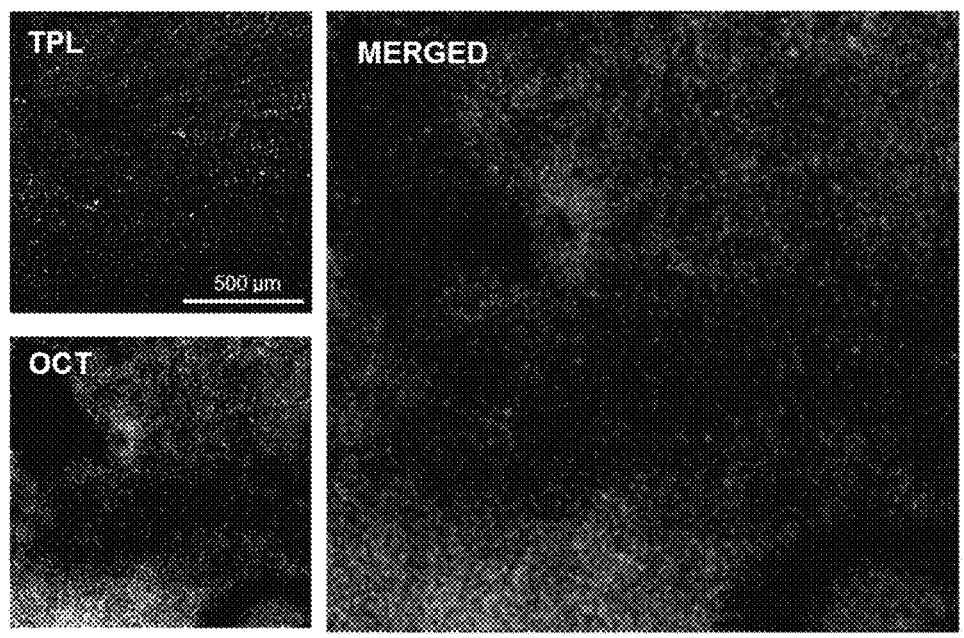

In certain embodiments, the systems shown in FIGS. 5A and 5B can be used to produce a merged image of TPL and OCT images. Examples of TPL, OCT and merged tissue images of a human coronary artery are shown in FIGS. 22 and 23. As shown in the figures, the merged image may use different colors to indicate the portion of the image obtained with OCT (in this example, green) and TPL (in this example, red).

During operation of the system used to produce the images in FIGS. 22 and 23, the OCT parameters were as follows—swept laser: 1310 nm/110 nm; beam size: 20 µm; laser power: 1.2 mW; field of view: 2 mm×2 mm; and A-scan rate: 20 kHz. In addition, the TPL parameters of the system used to produce the images of FIGS. 22 and 23 are as follows—2-P excitation laser: 760-1040 nm, 120 fs, 80 MHz; pixel dwell time: 4 µs; laser power: 500 mW; beam size: 20 µm; emission filter: <700 nm; field of view: 2 mm×2 mm.

Figure 24:
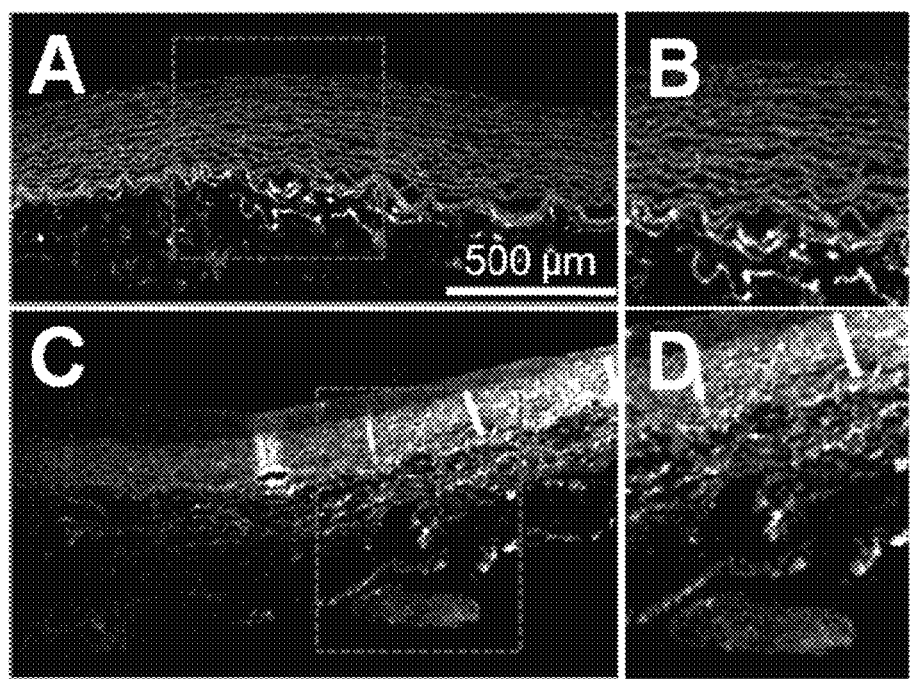

Referring now to FIG. 24, images are displayed that were obtained with TPL imaging techniques according to exemplary embodiments. The images display rabbit aorta tissue slices with atherosclerotic plaques. The bright TPL signals are native auto-fluorescence from lipid droplets, collagen and elastin fibers.

Figure 25:
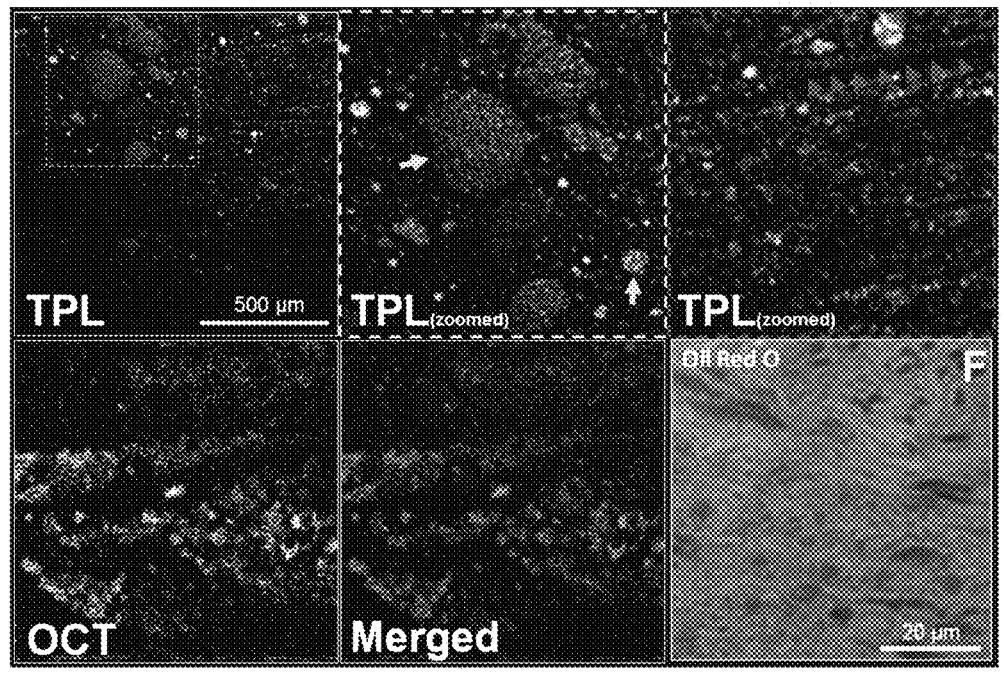

FIG. 24 displays TPL, OCT and merged TCL-OCT images of human coronary artery tissue obtained with a fiber-based system according to exemplary embodiments. In addition, the lower right portion of FIG. 25 comprises a stained tissue slice that indicates the distribution of lipids.

Example 5

Catheter-Based Polarization-Sensitive OCT-TPL System

One example of the catheter-based polarization-sensitive OCT-TPL system (shown in FIG. 6) can incorporate a spectral-domain polarization-sensitive OCT (PSOCT) system operating at 1310 nm combined with TPL using a tunable femtosecond laser excitation (e.g., 760-1040 nm, 6 nJ-5 µJ, 100 fs-1 ps, 500 kHz-80 MHz). The system in FIG. 6 comprises polarization maintaining fiber segments (PM1 and PM2) that act as an in-line fiber polarimeter; a polarization beam splitter (PBS); a band-pass filter (BP); a short-pass filter (SP); a photon multiplier tube (PMT); and a photonic crystal fiber (PCF).

The PSOCT system utilizes balanced detection and an in-line fiber polarimeter [29] to measure the polarization state of both reference light and interference fringes. An open optical switch in the sample path of the interferometer allows measurement of a signal containing only the polarization state of reference light (without interference fringes between reference and sample light). A pulse compressor can be utilized to pre-compensate the group delay dispersion of femtosecond laser light to provide transform-limited pulses on the luminal surface. The imaging catheter can be connected to a photonic crystal fiber (PCF) (e.g., LMA-20, NKT Photonics) of the OCT-TPL imaging system, which can enable propagation of both OCT light and TPL excitation/emission light.

Example 6

Catheter-Based Spectral Domain Phase-Sensitive OCT-TPL System

One example of a catheter-based phase-sensitive OCT-TPL system (shown in FIG. 7) can incorporate a spectral-domain phase-sensitive OCT (PhSOCT) system operating at 1310 nm combined with TPL using a tunable femtosecond laser excitation (e.g., 760-1040 nm, 6 nJ-5 µJ, 100 fs-1 ps, 500 kHz-80 MHz). The system of FIG. 7 comprises a polarization beam splitter (BS); a band-pass filter (BP); a short-pass filter (SP); a photon multiplier tube (PMT); and a photonic crystal fiber (PCF).

A pulse compressor can be utilized to pre-compensate the group delay dispersion of femtosecond laser light to provide transform-limited pulses incident on the luminal surface of the vessel being imaged. The imaging catheter can be connected to a photonic crystal fiber (PCF) (e.g., LMA-20, NKT Photonics) of the OCT-TPL imaging system, which can enable single-mode propagation of both OCT light and TPL excitation light and transmission of TPL emission light.

Example 7

OCT-TPL Catheter Design and Optical Simulation Using ZEMAX

In this example, the OCT-TPL catheter will modify the current OCT catheter to incorporate the TPL excitation and emission. Previously, detection of macrophages loaded with nanoparticles was performed using a custom-built multiphoton microscope [30]. Therefore, it is desirable to compare the TPL excitation efficacy of the proposed catheter-based OCT-TPL imaging system with the multiphoton microscope. Table 6 shows the characterization of laser excitation from both imaging systems.

TABLE 6

Comparison of the TPL excitation efficacy of a multiphoton microscope with the proposed catheter-based OCT-TPL system.

| Laser Parameter | Multiphoton Microscope | Catheter-based OCT-TPL System |
|---|---|---|
| Wavelength (nm) | 800 | 800 |
| Repetition Rate (MHz) | 76 | 0.5-80 |
| Pulse Width (fs) | 150 | 10-1000 |
| Spot Size (µm) | 0.96 | 10-30 |
| Spot Area (µm$^2$) | 0.72 | 78.5-706.9 |
| Pixel Dwell Time (µs) | 2.5 | 4-20 |
| Number of Pulses per Pixel | 190 | 10-1600 |
| Average Power on Sample (mW) | 20 | 500-2500 |
| Pulse Energy (nJ) | 0.26 | 6-5000 |
| Instantaneous Power (MW) | 1.75E-3 | 0.0625-5 |
| Instantaneous Power Density (MW/µm$^2$) | 1.16E-3 | 2E-4-16E-3 (based on a 20 µm spot size) |

As a PCF will be used to deliver TPL excitation light, the instantaneous power that can be delivered is limited by onset of non-linear effects in the PCF, which can be described using the Nonlinear Schrödinger equation:

$$\frac{\partial A}{\partial z} + \frac{i\beta_2}{2}\frac{\partial^2 A}{\partial t^2} = i\gamma|A|^2 A$$

Where $|A|^2$, $\beta_2$, $\gamma$, z and t are, respectively, pulse instantaneous power [W], group velocity dispersion parameter [$fs^2$ $cm^{-1}$], nonlinear parameter [$W^{-1}km^{-1}$], position [cm] and time [s]. For the PCF used in this example, given that $\gamma=21$ $W^{-1}km^{-1}$ [17], $\beta_2=-172$ $fs^2$ $cm^{-1}$, $\lambda=800$ nm, $c=3\times10^8$ m/s, the maximum instantaneous power below the threshold of nonlinear effects in the PCF is solved from the Nonlinear Schrödinger equation: $|A|^2=-2\pi^2c^2\beta_2/(\lambda^2\gamma)=4.49$ MW. Although the femtosecond laser in OCT-TPL system can provide an instantaneous power of 5 MW (see Table 6), the actual instantaneous power that propagates in the PCF can be limited to approximately 4.49 MW to be less than the threshold of nonlinear effect. Allowance of some nonlinearity in the PCF may provide for spectral broadening and additional pulse compression.

Figure 8:
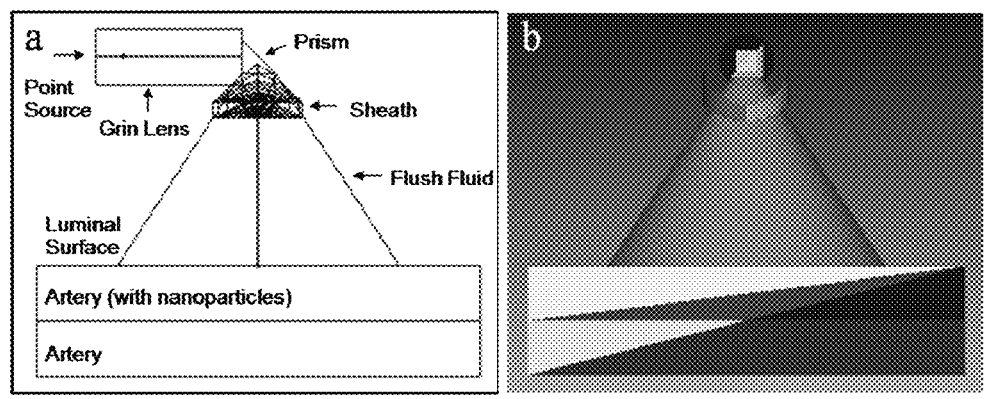
FIG. 8 shows a schematic of an apparatus according to an exemplary embodiment.

ZEMAX is a software program which can model, analyze, and assist in the design of optical systems. Exemplary embodiments of OCT-TPL catheters can be simulated and validated using ZEMAX. A ZEMAX model of the OCT-TPL catheter has been built to simulate OCT and TPL light interaction with arterial tissue containing gold nanoparticles (see e.g. FIG. 8, which provides: (a) a 2-D side-view of OCT-TPL catheter; and (b) 3-D front-view of OCT-TPL catheter).

The catheter is modeled using a grin lens (material: GTAG), a prism (BK7), a sheath (THV_GENERIC) and flush fluid (seawater). Arterial tissue is modeled using a two-layer geometry. Top-layer contains gold nanoparticles ($\mu_a=181$ $cm^{-1}$) and intima ($\mu_s=239$ $cm^{-1}$), while bottom-layer is composed of only intima. The absorption coefficient of intima tissue and scattering coefficient of nanoparticles are ignored since they are negligible compared to those of gold nanoparticles and intima tissue, respectively.

ZEMAX simulation of OCT and TPL light interaction with arterial tissue is performed in three steps: (1) incident OCT (1310 nm) and TPL (800 nm, 1.35 MW, NA=0.04) excitation rays onto arterial tissue from a point source located at the center of the front surface of the grin lens. (2) a single macrophage cell (containing gold nanoparticles) at the beam-tissue interface is excited and emits TPL. (3) TPL emission rays from the macrophage cell is traced back to the catheter and detected by a detector located at the front surface of the grin lens (not shown in FIG. 6).

Three important parameters are calculated from the ZEMAX simulation, including TPL optical path length (OPL), OCT and TPL emission spot size at the front surface of the grin lens, and TPL emission power at the front surface of the grin lens which can be coupled into the PCF. Specifically, Table 7 shows the OPLs of five different wavelengths of TPL excitation ranging from 798-802 nm both at chief ray and edge ray directions. Results indicate that the dispersion of TPL excitation pulse within the range of 5 nm from the front surface of the grin lens to arterial tissue surface is less than 1 fs.

TABLE 7

Dispersion of TPL excitation light ranging from 798-802 nm both at chief ray and edge ray directions.

| Wavelength (nm) | OPL (mm) Chief Ray ($\theta = 0°$) | OPL (mm) Edge Ray ($\theta = 2.29°$) |
|---|---|---|
| 798 | 4.91664060 | 4.91662242 |
| 799 | 4.91656997 | 4.91655178 |
| 800 | 4.91649954 | 4.91648133 |
| 801 | 4.91642930 | 4.91641106 |
| 802 | 4.91635924 | 4.91634099 |

TABLE 7-continued

Dispersion of TPL excitation light ranging from 798-802 nm both at chief ray and edge ray directions.

| Wavelength (nm) | OPL (mm) Chief Ray ($\theta = 0°$) | OPL (mm) Edge Ray ($\theta = 2.29°$) |
|---|---|---|
| Numerical Aperture (NA) | 0.04 | 0.04 |
| ΔOPL (μm) | 0.281353472 | 0.281426256 |
| Dispersion (fs) | 0.93784 | 0.93809 |

Figure 9:
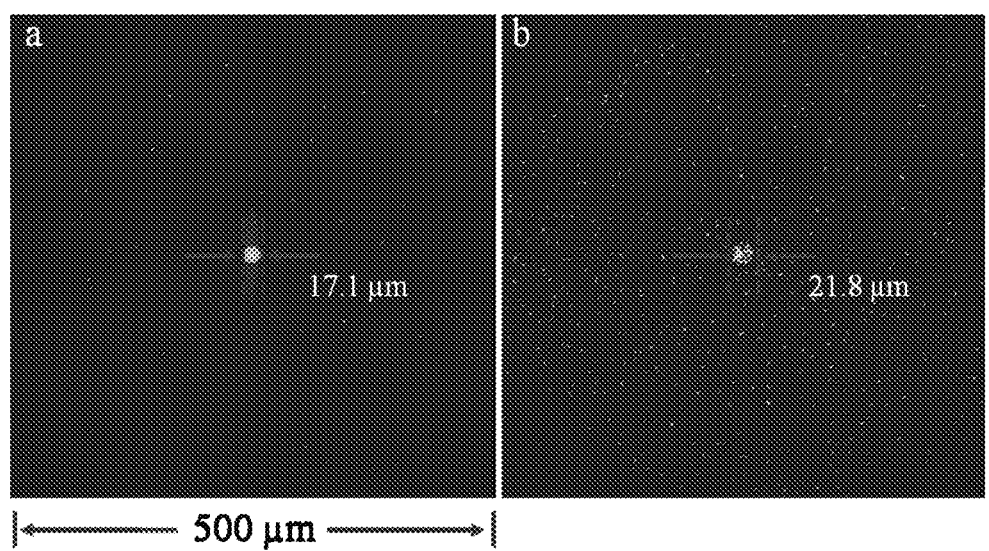
FIG. 9 shows an image obtained from an apparatus according to an exemplary embodiment.

The OCT and TPL spot size at the front surface of the grin lens is measured by a detector located at the same position in ZEMAX (FIG. 9, which shows the OCT and TPL spot size at the front surface of the grin lens measured by a detector located at the same position. The size of the detector is the same as the diameter of the grin lens.) As NA of OCT light (0.05) is higher than TPL excitation (0.04), OCT spot size (17.1 μm) is slightly smaller than TPL emission spot size (21.8 μm). The PCF to be used has a core diameter of, for example, 25 μm, which indicates that both OCT and TPL spot size can be fit into the core.

The TPL emission power that can be coupled into the PCF core is then calculated from the detector shown in FIG. 5, only the rays within the 25 μm diameter from the center of spot size are included. Based on TPL excitation instantaneous power (1.35 MW), the detected TPL emission instantaneous power at the detector within the 25 μm diameter is calculated to be $1.51\times10^{-4}$ W, which suggests that a single TPL excitation pulse (800 fs) is able to generate 425 photons/pulse. As TPL excitation and OCT repetition rates are, respectively, 500 kHz and 50 kHz, 10 TPL excitation pulsed can be recorded within a single OCT A-scan, which results in 4250 photons/OCT A-scan. In comparison, the multiphoton microscope used to collect data records 0.7 photons/pulse (calculated from the Hamamatsu PMT specifications [31], data not shown) and the accumulated photons/pixel in a typical TPL image of nanoroses from the multiphoton microscope are limited to 133 photons/pixel. Therefore, the detection efficacy of catheter-based OCT-TPL system is more than an order of magnitude higher than the currently used multiphoton microscope.

Example 8

Nanorod Selection

Gold nanorods can be internalized by macrophages (an important early cellular marker involved in atherosclerosis and cancer) and used as a contrast agent for a variety of imaging techniques for macrophage targeting. An objective of this study is to compare two-photon luminescence (TPL) properties of four sizes of gold nanorods with surface plasmon resonance at 700, 756, 844 and 1060 nm respectively. TPL from single nanorods and rhodamin 6G particles was measured using a laser-scanning TPL microscope. TPL emission spectrum from nanorods was recorded by a spectrometer with a photon multiplying CCD. All four sizes of nanorods produced strong TPL intensities with a dependence on the excitation wavelength, indicating the two-photon action cross section (TPACS) is plasmon-enhanced. Quadratic dependence of luminescence intensity on excitation power (confirming a TPL process) was observed at low power levels, followed by an intensity saturation or decrease at high power levels due to a photobleaching effect. Largest TPACS of a single nanorod was measured to be 12271 GM compared to 25 GM of a single rhodamin 6G particle at 760 nm excitation. Characteristics of nanorods TPL emission spectrum can be explained by the recombination of electrons near the Fermi level with holes near the X and L symmetry points in the Brillouin zone. Comparison results of TPL brightness, TPACS and emission spectra of nanorods can be used to guide selection of brightest contrast agent for selected imaging applications.

Atherosclerosis, one of the most common cardiovascular diseases, accounts for one-third of all deaths in the United States. [32]. Macrophages in the blood stream infiltrate into the intimal layer of blood vessels containing atherosclerotic plaques and become plaque-based macrophages (PBMs). PBMs accelerate inflammation by releasing matrix metalloproteinases (MMPs) which erode the thin fibrous cap (less than 65 μm in thickness) and make the plaques more prone to rupture [33, 34]. Tumor-associated macrophages (TAMs) are known to play a fundamental role in the progression of many cancers (e.g., breast, prostate, ovarian, cervical, lung carcinoma and cutaneous melanoma) [35]. In tumors, infiltrated TAMs provide an immunosuppressive microenvironment (through direct and indirect suppression of cytotoxic T cell activity) for tumor growth, promote angiogenesis, and produce soluble mediators that support proliferation and survival of malignant cells [36]. For these reasons, TAM density in solid tumors is generally described as correlating inversely with patient prognosis [35]. Additionally, an association between TAM presence and local invasion into ectopic tissue and/or metastasis has been established in many cancers [35, 36]. Thus, macrophage is an important early cellular marker that provides information relevant to the risk of future plaque rupture and staging and metastasis of cancers. In vivo macrophage detection is of great clinical significance and has motivated development of macrophage-targeting contrast agents such as gold nanoparticles.

A variety of gold nanoparticles with different coatings have been developed to target macrophages due to their unique optical properties (i.e., absorption, scattering and fluorescence), negligible cytotoxicity and good biocompatibility, including nanospheres [37, 38], nanoshells [39, 40], nanocages [41, 42], nanoroses [43, 44], nanorods [45, 46], etc. While the quantum yield of bulk gold fluorescence was observed to be extremely weak ($\sim 10^{-10}$) [47], gold nanoparticles can strongly enhance the local light-field amplitude [48, 49] and significantly increase the quantum yield to the $10^{-4}$ level [49] by the surface plasmon resonance (SPR) effect [51-53], which is known as coherent oscillation of electrons in the conduction band of the gold nanoparticle in resonance with the incident electromagnetic light-field of light. Due to drastic suppression of interband damping, nanorods exhibit higher local field enhancement factors than small nanospheres [54]. Mohamed et at observed a more than $10^6$ times enhancement of quantum yield of gold nanorods by single photon plasmonic excitation over bulk gold [55]. Nanorods, unlike their counterparts with symmetrical shapes (e.g., nanospheres, nanoshells and nanocages), can easily tune the SPR to near-infrared wavelengths (where tissue absorption is at minimum) by varying the aspect ratios [56-59]. Moreover, the synthesis procedure of nanorods is well established, providing better monodispersity and stability compared to the synthesis of other complex nanostructures (e.g., nanoroses and nanocages). Two-photon or multi-photon excitation processes, better than single-photon excitation, provide additional local field enhancement and, thus, a greater enhancement of quantum yield with stronger emission signals. Although the single-photon quantum yield of a nanorod is in the order of $10^{-4}$, it has been reported that the two-photon action cross section (TPACS) of nanorod can reach 2320 GM, which is within the range of that of quantum dots (2000-47000 GM) [60] and much higher than that of organic fluorophores (e.g., rhodamin 6G), providing a promising approach to detect these nanorods in biological tissues using two-photon excitation.

Two-photon luminescence microscopy (TPLM) is of particular interest because of its near-infrared excitation where tissues scatter more weakly and have less absorption. TPLM can provide best contrast of nanorods and highest 3-D spatial resolution compared to other imaging modalities (e.g., MRI, CT, PET, OCT and ultrasound) [61-63]. Several TPLM studies of single nanorods have been reported with detailed description of quadratic power dependence [64, 65], local field enhancement at specific positions of nanorod [65], luminescence polarization and spectrum [60, 67]. However, further characterization and comparison of two-photon luminescence (TPL) from nanorods of different sizes at multiple excitation wavelengths is needed, these include: (1) comparison of TPL brightness of nanorods, (2) range excitation power of TPL process and photobleaching effect of nanorods, (3) TPACS of nanorods, and (4) TPL spectra of nanorods. These studies can provide a deeper understanding of TPL from nanorods and guide contrast agent selection and optimization.

In this study, a laser-scanning TPL microscope was used to investigate the TPL characterization of nanorods of different sizes at multiple excitation wavelengths. Nanorods with plasmon-resonance at 756 nm were found to be the brightest (at same excitation power) among all four sizes of nanorods at 760 nm excitation. All nanorods exhibit a quadratic dependence of TPL intensity on excitation power at low power levels, followed by an intensity saturation or decrease at high power levels due to a photobleaching effect. TPACS of four nanorods at three excitation wavelengths was calculated and compared. TPL emission spectra of nanorods was interpreted by electron-hole recombination and is consistent with TPL brightness measurement. Results of these experiments and analysis suggest that nanorod size determines not only SPR position but also TPL brightness, TPACS and TPL emission spectrum.

Materials and Methods

Sample Preparation

Figure 10:
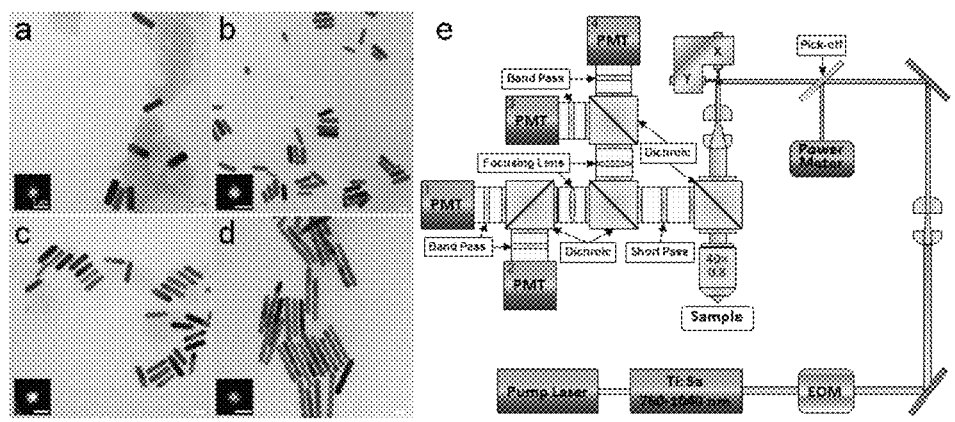
FIG. 10 shows a schematic of an apparatus according to an exemplary embodiment.

Gold nanorods were synthesized in solution using a seeded growth method as described previously [68]. Four sizes of nanorods with surface plasmon resonance at 700, 756, 844 and 1060 nm respectively were purchased from Nanopartz, briefly sonicated and diluted 10 times from stock concentration before use. Nanorod samples were prepared by dispersing 5 μl dilution onto a glass slide and covered by a coverslip, forming a 5 μm thick nanorod solution. Final concentration of four sizes of nanorods on the glass slide are, respectively, $5.7 \times 10^{10}$, $4 \times 10^{10}$, $7.2 \times 10^{10}$ and $2.8 \times 10^{10}$ nanoparticles/ml. Transmission electron microscopy (TEM) revealed morphologies of nanorods and TPL images showed the shapes of a single nanorod at the diffraction limit (FIG. 10a-d). FIG. 10 provides TEM images of gold nanorods used in the study: (a) Au700, (b) Au756, (c) Au844, (d) Au1060. Insets in (a, b, c, d) are TPL images of a single nanorod at 840 nm excitation within the spectral range of 400-700 nm. Scale bars in TEM and TPL images represent 20 nm and 1 μm, respectively. (e) Schematic diagram of the laser scanning TPL microscope. EOM: electro-optic modulator; PMT: photomultiplier tube.

The long axis of the gold nanorods are in the range of 35-67 nm, with corresponding aspect ratios of 2.9, 3.5, 4.4 and 6.7, respectively. Rhodamin 6 G (Sigma-Aldrich, St. Louis, Mo.) was diluted into two concentrations in DI water:

110 μM and 1 pM. Sample with 110 μM was sealed into a cuvette, while sample with 1 pM was dispersed and then dried on a glass slide (forming a distribution of single rhodamin 6G particles). TPACS spectrum was measured for both cuvette and dried rhodamin 6G samples.

TPL Microscopy

TPL from nanorods was measured using a laser scanning TPL microscope (FIG. 10b, Prairie Technologies, Middleton, Wis.). A femtosecond Ti:Sapphire laser (Mai Tai H P, Newport, Irvine, Calif.) emitting at 760-1040 nm (80 MHz, 100 fs) was used as an excitation light source. Intensity of the laser beam entering the microscope was modulated by an electro-optic modulator (350-80, ConOptics, Danbury, Conn.) and monitored by a pick-off mirror (reflectance 1%) with a power meter for measuring the power delivered to the sample. The focal volume of the objective lens (40×, NA=0.8, water emersion, Olympus, Center Valley, Pa.) was scanned over the sample in the x-y plane using a pair of galvanometric scanning mirrors to produce 2-D images. TPL emission from sample was collected through the same objective, separated from the excitation laser line by a 720 nm long-pass dichroic mirror, directed into four channels and detected by four photomultiplier tubes (PMT1,2: H7422P-40, PMT3,4: R3896, Hamamatsu, Bridgewater, N.J.) in spectral ranges of 640-680, 570-620, 490-560 and 435-485 nm, respectively. To minimize the photon count from excitation laser line, a short-pass filter (et720sp, Chroma Technology, Bellows Falls, Vt.) was placed after the dichroic mirror. In this study, only PMT1 was used to collect TPL emission signals (less than 720 nm) with absence of dichroic mirrors and a band-pass filter in detection light path. The TPL was also measured by replacing PMT1 with a fiber-coupled spectrometer with a photon multiplying CCD (Shamrock 303i, And or Technology, Belfast, Ireland).

TPACS Calculation

TPACS of nanorods were determined by a comparison method of the TPL emission from the reference rhodamin 6G sample. TPL emission from a sample can be expressed in Eq. (1) with related parameters [69]:

$$F \Box \frac{1}{2} \phi C \eta_2 \sigma_2 \frac{g_p}{f\tau} \frac{8nP^2}{\pi\lambda} \quad (1)$$

Where F (in photons/second) is the TPL photons collected per unit time, $\phi$ (dimensionless) is the TPL collection efficiency of the measurement system, C (in mol/ml) is the fluorophore concentration (i.e., nanorod and rhodamin 6G), $g_p$ (dimensionless) is the degree of second-order temporal coherence of the excitation source, f is the laser modulation frequency, $\tau$ is the FWHM pulse width, n is the refractive index of the sample, P (in photons/second) is the excitation laser power, $\lambda$ is the excitation wavelength, $\eta_2\sigma_2$ (in GM; 1 GM=$10^{-50}$ cm$^4$s/photon) is the TPACS where $\eta_2$ and $\sigma_2$ are quantum yield and two-photon absorption cross section respectively. By measuring the TPL emission intensity from single particles in TPL images, $F_n$ (nanorod) and $F_r$ (rhodamin 6G) were obtained. Here, all TPL signals were measured under identical excitation wavelength with the same experimental conditions in the same system, therefore, $\phi$, $g_p$, f, $\tau$ and $\lambda$ are the same for nanorod and rhodamin 6G samples. Using Eq. (1) for two samples and change P to average power $\overline{P}$ (in Watts), TPACS of nanorod $((\eta_2\sigma_2)_n)$ can be determined by comparing with the known TPACS of rhodamin 6G $((\eta_2\sigma_2)_r)$ as shown in Eq. (2):

$$(\eta_2\sigma_2)_n = \frac{n_r}{n_n} \cdot \frac{\overline{P}_r^2}{\overline{P}_n^2} \cdot \frac{F_n}{F_r} \cdot (\eta_2\sigma_2)_r \quad (2)$$

Results

Power Dependence of Nanorod Brightness

Figure 11:
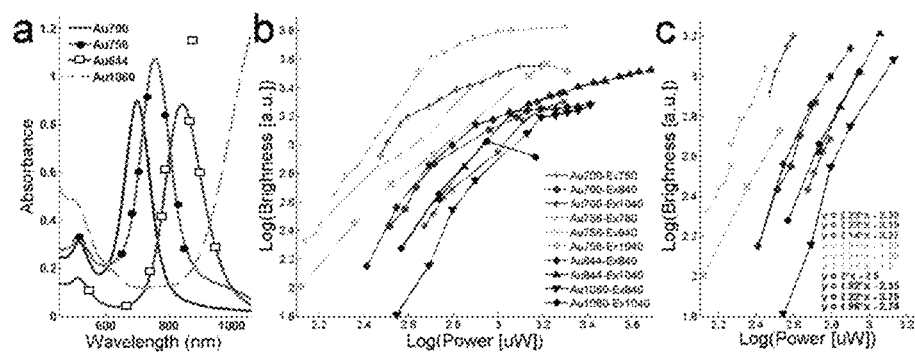
FIG. 11 shows data obtained from an apparatus according to an exemplary embodiment.

FIG. 11a shows single-photon absorbance spectra of four sizes of nanorods measured at a concentration of 4×1011 nanoparticles/ml. FIG. 11b shows MPL intensity dependence on the excitation laser power (132 μW-4.8 mW) of nanorods at wavelengths of 760, 840 and 1040 nm. FIG. 11c shows quadratic dependence of luminescence intensity of nanorods on excitation laser power at lower power levels in (b). Slopes of 1.7-2.2 (for each size of nanorod at different excitation wavelength) confirm the TPL process.

For each nanorod, two surface plasmon resonance (SPR) absorption peaks are visible, one at around 520 nm is due to transverse oscillation of electrons and insensitive to the size of nanorods. The other absorption peak is red-shifted to longer wavelengths and is due to longitudinal oscillation of electrons with a peak wavelength that increases with nanorod aspect ratio [55,69]. Amplitude of longitudinal SPR also increases with aspect ratio (except for Au844), consistent with theoretical calculations [56]. Multi-photon luminescence (MPL) of four sizes of nanorods at three excitation wavelengths (i.e., 760, 840, 1060 nm) was measured by the TPL microscope. FIG. 11b shows nanorod brightness dependence on the excitation laser power (132 μW-4.8 mW) in logarithmic scale. MPL signal intensity is observed to first linearly increase (i.e., slope≈2) at lower excitation powers for each nanorod, then the curve starts to bend and form an exponential-like increase followed by signal saturation (e.g., Au700-Ex760, 840, 1040; Au756-Ex760; Au844-Ex840, 1060; Au1060-Ex840) or signal decrease (Au760-Ex1040, Au1060-Ex1040). At the same excitation power, MPL signal intensity is higher when excitation wavelength is closer to the longitudinal SPR of the nanorod. When the excitation is at (or close to) the longitudinal SPR wavelength, MPL signal intensity (i.e., nanorod brightness) is observed to follow: Au756>Au700>Au844>Au1060, where Au756 appears 11 times brighter than Au1060 at the excitation power of 372 μW. FIG. 11c shows nanorod MPL at lower excitation power levels of FIG. 11b. Slopes of all curves ranging from 1.7-2.2 show a quadratic dependence of luminescence signal intensity on the laser excitation power, indicating a TPL process. Of note is that the TPL process power range varies with nanorod size, where bigger nanorods (e.g., Au844, Au1060) appear to have wider power ranges than smaller nanorods (e.g., Au700, Au756).

MPL response as a function of time was measured to test MPL photobleaching properties of nanorods. Nanorods in a smaller field of view (20×20 μm$^2$) were irradiated at 2 mW for 30 s and a TPL image was recorded by immediately zooming out to a larger field of view (80×80 μm$^2$) as shown in FIG. 12a where the red box indicates the smaller field of view. For each excitation wavelength, the averaged intensity of nanorods in the red box was normalized to that of the nanorods outside the red box in the larger field of view and results were shown in FIG. 11b. While all sizes of nanorods in the red box showed a MPL signal drop after 30 s laser irradiation compared to those in the larger field of view where nanorods experienced a much shorter irradiation time, it was observed that larger sizes of nanorods (i.e., Au844, Au1060) showed a more drastic signal drop (e.g., 35% drop for Au1060 at 1040 nm excitation) at longitudinal SPR excitation wavelength compared to smaller nanorods (e.g., 2% drop for Au756 at 760 nm excitation). MPL temporal response of nanorods suggest that a photobleaching effect is evident, especially in larger sizes of nanorods.

FIG. 12a shows a typical TPL image (80×80 μm2) of Au1060 at 844 nm excitation acquired after 30 s laser irradiation at 2 mW in the red box (20×20 μm2) in (a) where a MPL signal drop of nanorods is observed. FIG. 12b shows averaged MPL signal of nanorods in the red box (second bar of the same color) was normalized to that of the nanorods outside the red box in the larger field of view (first bar of the same color) for four sizes of nanorods at three excitation wavelengths. Error bar represents standard deviation.

TPACS Measurement of Nanorods

TPACS of rhodamin 6G needs to be measured before that of nanorods can be determined. TPACS of rhodamin 6G solution with an excitation wavelength range of 690-960 nm has been reported by Albota et at [71], however, this data does not include wavelength range of 960-1040 nm. In this study, the normalized TPACS were measured and calculated of both rhodamin 6G solution and single particle using Eq. (1) at excitation wavelength range of 760-1040 nm extending Albota et at data by 80 nm. A TPL process of rhodamin 6G was observed at all excitation wavelengths and applied power range (data not shown). Measurement of rhodamin 6G solution reasonably matches reported values in 760-960 nm range with the major absorption peak overlapped at 820 nm. The absorption peak of a single rhodamin particle has a blue shift to 800 nm and the second peak at 1000 nm is drastically attenuated compared to rhodamin 6G solution. TPACS of a single rhodamin 6G particle was then used as a brightness reference for comparison with nanorods in accordance with Eq. (2).

TPL signals of nanorods were measured at less than 1 mW excitation power where a TPL process can be warranted. The TPL brightness of a single nanorod was then compared with that of a single rhodamin 6G particle using Eq. (2) and results are shown in Table 8. We observe that (1) All nanorods have largest TPACS at or close to the longitudinal SPR wavelength, consistent with previous measurement on gold nanorods with longitudinal SPR at 820 nm [60]. TPACS decreases monotonically with excitation wavelength departing from the longitudinal SPR; (2) Smaller nanorods have larger TPACS than bigger nanorods with excitation wavelength at or close to the longitudinal SPR (e.g., Ex760 for Au 756 and Au700 compared to Ex840 for Au844 and Ex1040 for Au1060). The TPACS of Au756 at 760 nm excitation is largest (12271 GM compared to 25 GM of a single rhodamin 6G particle) among all nanorods and excitation wavelengths investigated and about 15 times larger than that of Au1060 at 1040 nm excitation. The TPACS of Au844 at 840 nm excitation is 2039 GM, which is very close to 2320 GM reported previously for a slightly bigger size of nanorods excited at 830 nm [60].

Figure 13:
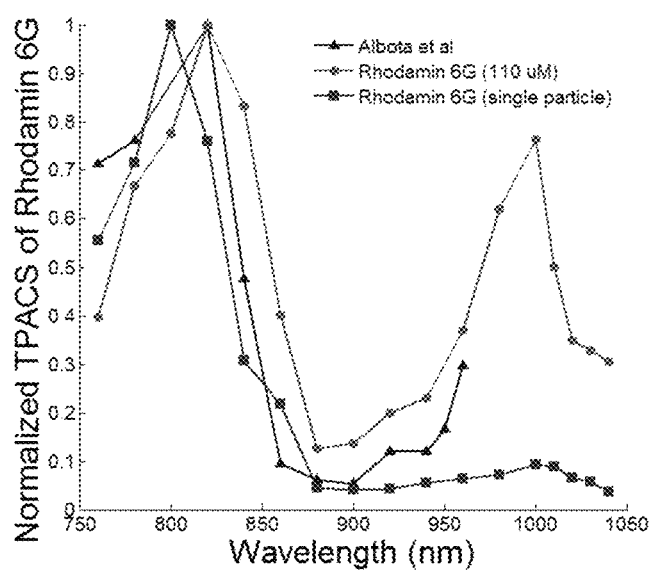
FIG. 13 shows data obtained from an apparatus according to an exemplary embodiment.

FIG. 13 shows normalized TPACS of rhodamin 6G single particle, rhodamin 6G solution and reported values from Albota et al [41] at wavelength range of 760-1040 nm. Single rhodamin 6G particles were formed from dried water solution; Rhodamin 6G solution has a concentration of 110 μM dissolved in DI water; Reported data used a rhodamin 6G concentration of 110 μM dissolved in MeOH.

TABLE 8

TPACS (in GM units) of single nanorod at excitation wavelengths of 760, 840 and 1040 nm respectively.

| | Au700 | Au756 | Au844 | Au1060 |
| --- | --- | --- | --- | --- |
| Ex760 | 9802 | 12271 | | |
| Ex840 | 2194 | 8412 | 2039 | 474 |
| Ex1040 | 632 | 2391 | 671 | 682 |

3.3 TPL Emission Spectra of Nanorods

To better characterize the TPL emission of nanorods, TPL emission spectra were collected from a nanorod solution (80×80 μm² field of view) in the spectral range of 350-700 nm at multiple excitation wavelengths (i.e., 760, 800, 840 and 1040 nm). The average excitation power on all nanorods was kept less than 1 mW so that a TPL process can be satisfied. TPL emission was then normalized by the number of incident photons and nanorod concentration and shown in FIG. 14.

Figure 14:
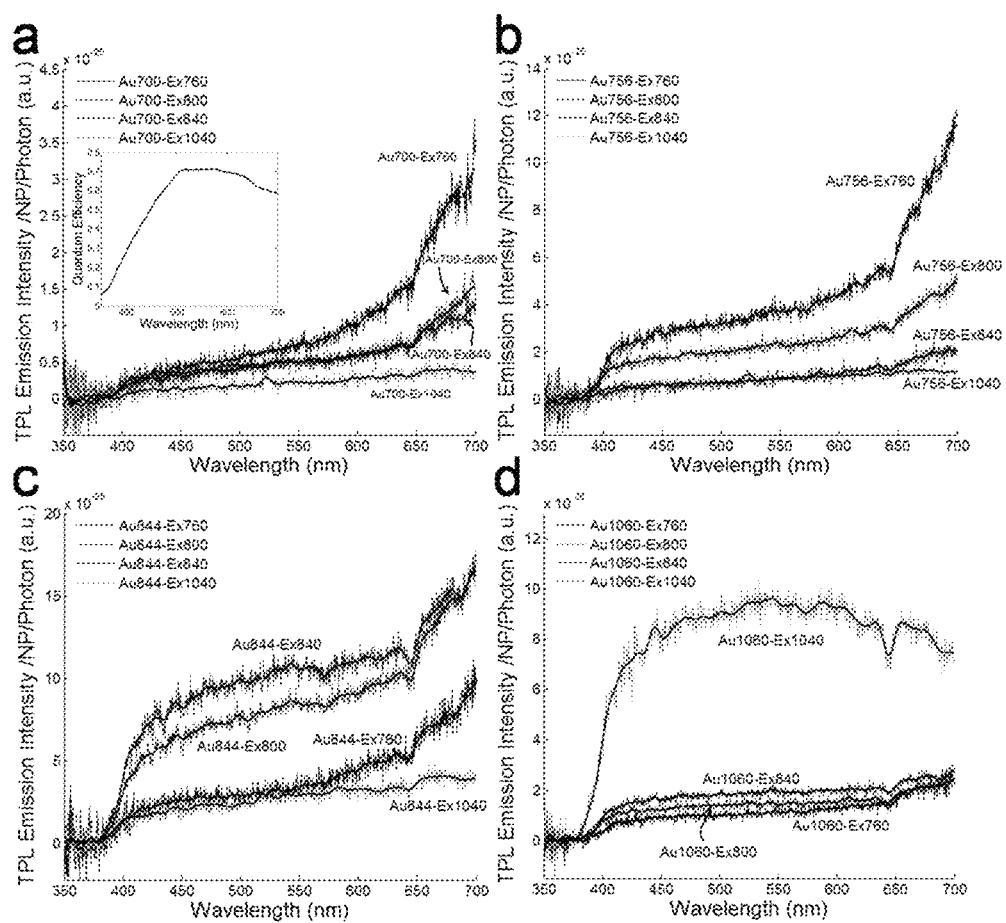
FIG. 14 shows data obtained from an apparatus according to an exemplary embodiment.

FIG. 14 shows TPL emission spectra of (a) Au700, (b) Au756, (c) Au844 and (d) Au1060 at the excitation wavelengths of 760, 800, 840 and 1040 nm. Inset in (a) represents total quantum efficiency of the detection system including the electron multiplying CCD and gratings of the spectrometer. Spectra was corrected for the quantum efficiency and normalized on the number of incident photons and nanorod concentration All TPL spectra were corrected for the total quantum efficiency of the photon multiplying CCD and gratings of the spectrometer (inset in FIG. 14a). For each nanorod size, TPL emission intensity appears highest at nanorod's longitudinal SPR wavelength and decreases monotonically with excitation wavelengths departing from the longitudinal SPR peak, suggesting the electric-field enhancement due to SPR absorption. The further the excitation wavelength shifts away from the SPR, the more drastically TPL emission signal drops, which is consistent with the results of PMT measurement of nanorod brightness as shown in FIG. 11b. All emission spectral intensities increase for lower photon energies where the excitation wavelength is located (except for Au1060 at 1040 nm excitation), which can be attributed to the dispersion of the localized SPR [72]. The emission spectral range can be separated into three wavelength bands: 400-575, 575-640 and 640-700 nm. Two dips at around 575 and 640 nm are visible in the spectra of all sizes of nanorods, and more evident for Au756, Au844 and Au1060. For smaller nanorods (i.e., Au700, Au756), TPL emission intensity in the 640-700 nm band increases more rapidly than the other two bands compared bigger nanorods (i.e., Au844). Interestingly, TPL emission of Au1060 exhibits a plateau in the 400-575 nm band followed by a signal decrease in 575-640 and 640-700 nm bands. Because the TPL mechanism for gold nanorods is the same as that for bulk gold metal [72], the emission peak regions should be attributed to the energy gap between the excited electrons at the Fermi level and the holes in the d-band. We note that the second harmonic signals are also observed for nanorods at 1040 nm excitation, and not seen at all other excitation wavelengths. Details of the spectral features are discussed below.

Discussion

As nanorod brightness is very important parameter in macrophage targeting and detection, and also determines the sensitivity of an imaging system, selecting the size of nanorod that yields strongest TPL signals is of great clinical interest and significance. In this study, four sizes of nanorods were compared and Au756 was found to emit strongest at the same excitation power and at the excitation wavelength of corresponding longitudinal SPR. In fact, fluorescence emission by single photon excitation from gold nanorods is determined by three factors as demonstrated by Eustis and El-Sayed in their experimental and simulation studies [73]: (1) The strength of single-photon absorbance at longitudinal SPR wavelength, which should increase with increasing nanorod aspect ratio (FIG. 11a). (2) The overlap between the SPR absorption band and the interband transition which is attributed to the electron transition between the d-band and conduction band, and started at the threshold energy around 1.8 eV (689 nm) [74, 75]. (3) The overlap between the SPR absorption band and the fluorescence band of bulk gold which peaks around 525 nm, decreases thereafter and diminishes beyond 750 nm [47]. The first factor is a competing component to the other two factors, the net effect of which determines the enhancement of TPL emission. In this study, as the aspect ratio of nanorods increases from 2.9 to 6.7, enhancement of longitudinal SPR increases while the overlap between the SPR absorption band and interband transition or bulk fluorescence of gold both decreases. Therefore, the observed strongest enhancement results in Au756 with an aspect ratio of 3.5, which is about 12 times higher than Au1060. This observation is very similar to that reported for nanorods with single-photon excitation, where quantum yield of nanorods increases quadratically for aspect ratios below 3.4 and decreases afterwards [76], and fluorescence emission starts to decline as aspect ratios increase beyond 3.25 to about an order of magnitude weaker with aspect ratio at 6 [73].

Figure 12:
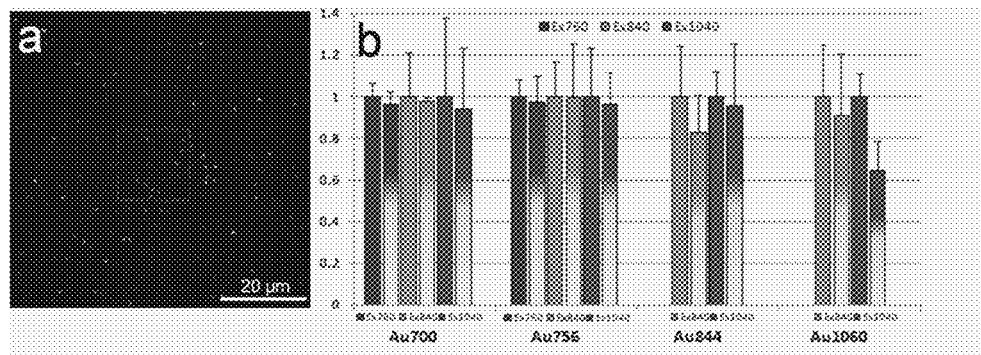
FIG. 12 shows data obtained from an apparatus according to an exemplary embodiment.

Unlike single-photon excitation where nanorods are essentially inert to photobleaching and light scattering on nanorods can stay constant for several hours of measurement time in contrast to fluorescence from quantum dots or dyes [77], TPL emission signal from nanorods exhibits various levels of photobleaching depending on the size of nanorods (FIG. 12). In fact, TPL emission is determined by instantaneous incident power. TPL emission signal first increases when increasing excitation power due to the enhancement of emission by incident field, then decreases and eventually diminishes due to vanishing of the enhancement by nanorod shape transformation or damage. Link and El-Sayed et at [78] demonstrated that the threshold for complete melting of the nanorods is about 0.01 J/cm$^2$ (100 GW/cm$^2$) with a pulse duration of 100 fs at 800 nm excitation, while an apparent shape transformation of nanorods and a decrease of longitudinal SPR band is observed at 10 GW/cm$^2$. Bouhelier et at [79] has shown that nanorods can be transformed to spherical shape at high excitation powers and the corresponding luminescence peak is blue-shifted, where emission enhancement can be greatly reduced. In this study, instantaneous power density at the beam focus was 13 GW/cm$^2$ (average power of 2 mW) at 1040 nm excitation, which is more than 10 GW/cm$^2$ and very likely to reshape part of the nanorods in the field of view. Therefore, it is expected that luminescence emission will be reduced and, moreover, this photobleaching effect is attributed to reshaping or partial nanorod damage, especially for those with a bigger size (i.e., Au844, Au1060) and aligned with polarization of incident laser light.

Gold crystal structure is known to have several symmetry points in the first Brillouin zone with electron transitions preferentially occurring near the X and L symmetry points [67, 80]. In gold nanorods, X and L symmetry points can be along the directions of the long axis and diagonal of nanorod, respectively [67]. The TPL emission process in nanorods can be interpreted in three steps [46,54,74]: (1) Electrons in occupied d-band (or possibly sp-conduction-band below the Fermi level [67]) are excited by two-photon absorption to unoccupied sp-conduction-band above the Fermi level and electron-hole pairs are created. (2) Excited electrons then lose energy (e.g., through intraband scattering) to move energetically closer to the Fermi level. (3) Recombination of the electron-hole pairs result in luminescent emission. According to band structure calculation of gold [72, 81], emission peak regions should be in the spectral ranges of 1.8-1.9 eV (652-689 nm), 2.3-2.4 eV (517-539 nm) and 3.1-3.3 eV (376-400 nm), which are attributed to the symmetry points of 6-5X, 6-5L and 6-4L, respectively. In this study, the TPL emission peaks of nanorods at corresponding longitudinal SPR excitation wavelengths are all observed to locate at around 680 nm and 530 nm, and a sharp rising edge presents at around 400 nm, which is very consistent with the band calculations of emissions from 6-5X, 6-5L and 6-4L symmetry points respectively. Worth noting is that second harmonic signals are evident only at 1040 nm excitation (consistent with the reported observation [71]) but not observed at other excitation wavelengths, which may result from the immersion of the weak second harmonic signals in the dispersion of the TPL emissions.

Conclusion

By utilizing TPLM, TPL properties of gold nanorods were investigated and characterized. Four sizes of nanorods with longitudinal SPR wavelengths of 700, 756, 844 and 1060 nm were excited at multiple excitation wavelengths (i.e., 760, 840, 1040 nm). Au756 was observed to emit strongest TPL signal at 760 nm excitation with the same excitation power among all nanorods. Quadratic dependence of TPL intensity on excitation power was satisfied at low power levels (e.g., <1.6 mW), while a photobleaching effect was evident especially for larger-sized nanorods at a high power level (e.g., >1.6 mW). TPACS of nanorods at three excitation wavelengths was calculated based on the measurement of normalized TPACS spectrum of a single rhodamin 6G particle. TPL emission spectra of nanorods match the electron band calculations of gold and is consistent with TPL brightness measurement. Results suggest that gold nanorods are a promising imaging contrast agent for TPLM, and brightest nanorods can be determined by comparison of TPL brightness, TPACS and emission spectra of nanorods.

All of the devices, systems and/or methods disclosed and claimed herein can be made and executed without undue experimentation in light of the present disclosure. While the devices, systems and methods of this invention have been described in terms of particular embodiments, it will be apparent to those of skill in the art that variations may be applied to the devices, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The contents of the following references are incorporated by reference herein:
[1] Yusuf S, Reddy S, Ounpuu S, Anand S, "Global burden of cardiovascular diseases: part I: general considerations, the epidemiologic transition, risk factors, and impact of urbanization," Circulation 104, 2746-2753 (2001)

[2] Libby P, Ridker P M, Maseri A, "Inflammation and Atherosclerosis," Circulation 105, 1135-1143 (2002)

[3] Libby P, Theroux P, "Pathophysiology of coronary artery disease," Circulation 111, 3481-8 (2005)

[4] Lucas A R, Korol R, Pepine C J, "Inflammation in atherosclerosis: some thoughts about acute coronary syndromes," Circulation 113, e728-732 (2006)

[5] Virmani R, Burke A P, Kolodgie F D, Farb A, "Pathology of the Thin-Cap Fibroatheroma: A Type of Vulnerable Plaque," J Intery Cardiol 16(3), 267-272 (2003)

[6] Davies M J, Richardson P D, Woolf N, Katz D R, Mann J, "Risk of thrombosis in human atherosclerotic plaques: role of extracellular lipid, macrophage, and smooth muscle cell content," Br Heart J 69, 377-381 (1993)

[7] Stary H C, Chandler A B, Dinsmore R E, "A definition of advanced types of atherosclerotic lesions and a histological classification of atherosclerosis: a report from the Committee on Vascular Lesions of the Council on Arteriosclerosis," Circulation 92, 1355-1374 (1995)

[8] Jonasson L, Holm J, Skalli O, Bondjers G, Hansson G K, "Regional accumulations of T cells, macrophages, and smooth muscle cells in the human atherosclerotic plaque," Arteriosclerosis 6, 131-138 (1986)

[9] Johnson J L, George S J, Newby A C, Jackson C L, "Divergent effects of matrix metalloproteinases 3, 7, 9, and 12 on atherosclerotic plaque stability in mouse brachiocephalic arteries," Proc Natl Acad Sci 102, 15575-15580 (2005)

[10] Henney A M, Wakeley P R, Davies M J, Foster K, Hembry R, Murphy G, Humphries S, "Localization of stromelysin gene expression in atherosclerotic plaques by in situ hybridization," Proc Natl Acad Sci 88, 8154-8158 (1991)

[11] Galis Z S, Sukhova G K, Lark M W, Libby P, "Increased expression of matrix metalloproteinases and matrix degrading activity in vulnerable regions of human atherosclerotic plaques," J Clin Invest 94, 2493-2503 (1994)

[12] Nikkari S T, O'Brien K D, Ferguson M, Hatsukami T, Welgus H G, Alpers C E, Clowes A W, "Interstitial collagenase (MMP-1) expression in human carotid atherosclerosis," Circulation 92, 1393-1398 (1995)

[13] Libby P, Geng Y J, Aikawa M, Schoenbeck U, Mach F, Clinton S K, Sukhova G K, Lee, R T, "Macrophages and atherosclerotic plaque stability," Curr Opin Lipidol 7, 330-335 (1996)

[14] Taubman M B, Fallon J T, Schecter A D, Giesen P, Mendlowitz M, Fyfe B S, Marmur J D, Nemerson Y, "Tissue factor in the pathogenesis of atherosclerosis," Thromb Haemost 78, 200-204 (1997)

[15] Kolodgie F D, Virmani R, Burke A P, Farb A, Weber D K, Kutys R, Finn A V, Gold H K, "Pathologic assessment of the vulnerable human coronary plaque," Heart 90, 1385-1391 (2004)

[16] van Zandvoort M, Engels W, Douma K, Beckers L, Oude Egbrink M, Daemen M, Slaaf D W, "Two-photon microscopy for imaging of the (atherosclerotic) vascular wall: a proof of concept study," J Vasc Res 41, 54-63 (2004)

[17] Zoumi A, Lu X A, Kassab G S, Tromberg B J, "Imaging coronary artery microstructure using second harmonic and two-photon fluorescence microscopy," Biophys J 87, 2778-2786 (2004)

[18] Boulesteix T, Pena A M, Pages N, Godeau G, Sauviat M P, Beaurepaire E, Schanne-Klein M C, "Micrometer scale ex vivo multiphoton imaging of unstained arterial wall structure," Cytometry Part A 69A, 20-26 (2006)

[19] Le T T, Langohr I M, Locker M J, Sturek M, Cheng J X, "Label-free molecular imaging of atherosclerotic lesions using multimodal nonlinear optical microscopy," J Biomed Opt 12(5), 0540071-05400710 (2007)

[20] Lilledahl M B, Haugen O A, de Lange Davies C, Svaasand L O, "Characterization of vulnerable plaques by multiphoton microscopy," J Biomed Opt 12(4), 0440051-04400512 (2007)

[21] Wang T, Mancuso J J, Sapozhnikova V, Dwelle J, Ma L L, Willsey B, Kazmi S M, Qiu J, Li X, Asmis R, Johnston K P, Feldman M D, Milner T E, "Dual-wavelength multi-frequency photothermal wave imaging combined with OCT for macrophage and lipid detection in atherosclerotic plaques", J Biomed Opt 17(3), 0360091-03600910 (2012)

[22] Wang T, Mancuso J J, Kazmi S M, Dwelle J, Sapozhnikova V, Willsey B, Ma L L, Qiu J, Li X, Dunn A K, Johnston K P, Feldman M D, Milner T E, "Combined two-photon luminescence microscopy and OCT for macrophage detection in the hypercholesterolemic rabbit aorta using plasmonic gold nanorose", Lasers Surg Med 44(1), 49-59 (2012)

[23] Xue P, Fujimoto J G, "Ultrahigh resolution optical coherence tomography with femtosecond Ti:sapphire laser and photonic crystal fiber," Chinese Science Bulletin 53(13), 1963-1966 (2008)

[24] Ryu S Y, Choi H Y, Na J H, Choi E S, Yang G H, Lee B H, "Optical coherence comography implemented by photonic crystal fiber," Opt Quant Electron 37(13-15), 1191-1198 (2005)

[25] Fu L, Gu M, "Double-clad photonic crystal fiber coupler for compact nonlinear optical microscopy imaging," Opt Lett 31, 1471-1473 (2006)

[26] Liu G, Kieu K, Wise F W, Chen Z, "Multiphoton microscopy system with a compact fiber-based femtosecond-pulse laser and handheld probe," J Biophoton 4, 34-39 (2011).

[27] Fu L, Jain A, Xie H, Cranfield C, Gu M, "Nonlinear optical endoscopy based on a double-clad photonic crystal fiber and a MEMS mirror," Opt Exp 14, 1027-1032 (2006)

[28] Wu Y, Xi J, Cobb M J, Li X, "Scanning fiber-optic nonlinear endomicroscopy with miniature aspherical compound lens and multimode fiber collector," Opt Lett 34, 953-955 (2009)

[29] Kim, E H, Dave, D P, Milner, T E. "Fiber-optic spectral polarimeter using a broadband swept laser source," Optics Communications, 249 351-356 (2005)

[30] Park J, Estrada A, Sharp K, Sang K, Schwartz J A, Smith D K, Coleman C, Payne J D, Korgel B A, Dunn A K, Tunnell J W, "Two-photon-induced photoluminescence imaging of tumors using near-infrared excited gold nanoshells," Opt Exp 16(3), 1590-1599 (2008)

[31] Available at http://sales.hamamatsu.com/assets/pdf/parts_H/m-h7422e.pdf

[32] V. L. Roger, A. S. Go, D. M. Lloyd-Jone, R. J. Adams, J. D. Berry, T. M. Brown, M. R. Carnethon, S. Dai, G. de Simone, E. S. Ford, C. S Fox, H. J. Fullerton, C. Gillespie, K. J. Greenlund, S. M. Hailpern, J. A. Heit, P. M. Ho, V. J. Howard, B. M. Kissela, S. J. Kittner, D. T. Lackland, J. H. Lichtman, L. D. Lisabeth, D. M. Makuc, G. M. Marcus, A. Marelli, D. B. Matchar, M. M. McDermott, J. B. Meigs, C. S. Moy, D. Mozaffarian, M. E. Mussolino, G. Nichol, N. P. Paynter, W. D. Rosamond, P. D. Sorlie, R. S. Stafford, T. N. Turan, M. B. Turner, N. D. Wong and J. Wylie-Rosett, "Heart disease and stroke statistics—

2011 update: a report from the American Heart Association," Circulation 123(4), e18-e209 (2011).

[33] E. Falk, P. K. Shah and V. Fuster, "Coronary plaque disruption," Circulation 92(3), 657-671 (1995).

[34] F. D. Kolodgie, R. Virmani, A. P. Burke, A. Farb, D. K. Weber, R. Kutys, A. V. Finn and H. K. Gold, "Pathologic assessment of the vulnerable human coronary plaque," Heart 90(12), 1385-1391 (2004).

[35] N. B. Hao, M. H. Lu, Y. H. Fan, Y. L Cao, Z. R. Zhang, and S. M. Yang, "Macrophages in tumor microenvironments and the progression of tumors," Clin. Dev. Immunol. 2012, 948098-948108 (2012).

[36] B. Ruffell, N. I. Affara, and L. M. Coussens. "Differential macrophage programming in the tumor microenvironment," Trends Immunol. 33(3), 119-126 (2012).

[37] R. Shukla, V. Bansal, M. Chaudhary, A. Basu, R. R. Bhonde, and M. Sastry, "Biocompatibility of gold nanoparticles and their endocytotic fate inside the cellular compartment: a microscopic overview," Langmuir 21(23), 10644-10654 (2005).

[38] M. M. Janát-Amsbury, A. Ray, C. M. Peterson, and H. Ghandehari, "Geometry and surface characteristics of gold nanoparticles influence their biodistribution and uptake by macrophages," Eur. J. Pharm. Biopharm. 77(3), 417-423 (2011).

[39] S. Lal, S. E. Clare, and N. J. Halas, "Nanoshell-enabled photothermal cancer therapy: impending clinical impact," Acc. Chem. Res. 41(12), 1842-1851 (2008).

[40] X. Ji, R. Shao, A. M. Elliott, R. J. Stafford, E. Esparza-Coss, G. Liang, X. P. Luo, K. Park, J. T. Markert, and C. Li, "Bifunctional Gold Nanoshells with a Superparamagnetic Iron Oxide-Silica Core Suitable for Both M R Imaging and Photothermal Therapy," J. Phys. Chem. C 111(17), 6245-6251 (2007).

[41] S. E. Skrabalak, L. Au, X. Lu, X. Li, and Y. Xia, "Gold nanocages for cancer detection and treatment," Nanomedicine (Lond) 2(5), 657-668 (2007).

[42] M. Longmire, P. L. Choyke, and H. Kobayashi, "Clearance properties of nano-sized particles and molecules as imaging agents: considerations and caveats," Nanomedicine (Lond) 3(5), 703-717 (2008).

[43] L. L. Ma, M. D. Feldman, J. M. Tam, A. S. Paranjape, K. K. Cheruku, T. A. Larson, J. O. Tam, D. R. Ingram, V. Paramita, J. W. Villard, J. T. Jenkins, T. Wang, G. D. Clarke, R. Asmis, K. Sokolov, B. Chandrasekar, T. E. Milner, and K. P. Johnston, "Small multifunctional nanoclusters (nanoroses) for targeted cellular imaging and therapy," ACS Nano 3(9), 2686-2696 (2009).

[44] T. Wang, J. J. Mancuso, S. M. Kazmi, J. Dwelle, V. Sapozhnikova, B. Willsey, L. L. Ma, J. Qiu, X. Li, A. K. Dunn, K. P. Johnston, M. D. Feldman, and T. E. Milner, "Combined two-photon luminescence microscopy and OCT for macrophage detection in the hypercholesterolemic rabbit aorta using plasmonic gold nanorose," Lasers Surg. Med. 44(1), 49-59 (2012).

[45] T. S. Hauck, A. A. Ghazani, and W. C. W. Chan, "Assessing the effect of surface chemistry on gold nanorod uptake, toxicity, and gene expression in mammalian cells," Small 4(1), 153-159 (2008).

[46] T. Niidome, M. Yamagata, Y. Okamoto, Y. Akiyama, H. Takahashi, T. Kawano, Y. Katayama, and Y. Niidome, "PEG-modified gold nanorods with a stealth character for in vivo applications," J. Control Release 114(3), 343-347 (2006).

[47] A. Mooradian, "Photoluminescence of metals," Phys. Rev. Lett. 22(5), 185-187 (1969).

[48] J. Zheng, C. Zhang, and R. M. Dickson, "Highly fluorescent, water-soluble, size-tunable gold quantum dots," Phys. Rev. Lett. 93(7), 077402-077405 (2004).

[49] G. Wang, T. Huang, R. W. Murray, L. Menard, and R. G. Nuzzo, "Near-IR luminescence of monolayer-protected metal clusters," J. Am. Chem. Soc. 127(3), 812-813 (2005).

[50] J. P. Wilcoxon, J. E. Martin, F. Parsapour, B. Wiedenman, and D. F. Kelley, "Photoluminescence from nanosize gold clusters," J. Chem. Phys. 108(21), 9137-9143 (1998).

[51] Y. Fang, W. Chang, B. Willingham, P. Swanglap, S. Dominguez-Medina, and S. Link, "Plasmon emission quantum yield of single gold nanorods as a function of aspect ratio," ACS Nano 6(8), 7177-7184 (2012).

[52] P. K. Jain, X. Huang, I. H. El-Sayed, and M. A. El-Sayed, "Review of some interesting surface plasmon resonance-enhanced properties of noble metal nanoparticles and their applications to biosystems," Plasmonics 2(3), 107-118 (2007).

[53] M. A. El-Sayed, "Some interesting properties of metals confined in time and nanometer space of different shapes," Acc. Chem. Res. 34(4), 257-264 (2001).

[54] C. Sönnichsen, T. Franzl, T. Wilk, G. von Plessen, J. Feldmann, O. Wilson, and P. Mulvaney, "Drastic reduction of plasmon damping in gold nanorods," Phys. Rev. Lett. 88, 077402-077405 (2002).

[55] M. B. Mohamed, V. Volkov, S. Link, and M. A. El-Sayed, "The 'lightning' gold nanorods: fluorescence enhancement of over a million compared to the gold metal," Chem. Phys. Lett. 317(6), 517-523 (2000).

[56] S. Link, M. B. Mohamed, and M. A. El-Sayed, "Simulation of the optical absorption spectra of gold nanorods as a function of their aspect ratio and the effect of the medium dielectric constant," J. Phys. Chem. B 106(16), 3073-3077 (1999).

[57] S. S. Verma and J. S. Sekhon, "Influence of aspect ratio and surrounding medium on localized surface plasmon resonance (LSPR) of gold nanorod," J. Optics 41(2), 89-93 (2012).

[58] P. K. Jain, X. Huang, I. H. El-Sayed and M. A. El-Sayed, "Noble metals on the nanoscale: optical and photothermal properties and some applications in imaging, sensing, biology, and medicine," Acc. Chem. Res. 41(12), 1578-1586 (2008).

[59] E. T. Castellana, R. C. Gamez, M. E. Gomez, and D. H. Russell, "Longitudinal surface plasmon resonance based gold nanorod biosensors for mass spectrometry," Langmuir 26(8), 6066-6070 (2010).

[60] H. Wang, T. B. Huff, D. A. Zweifel, W. He, P. S. Low, A. Wei, and J. X. Cheng, "In vitro and in vivo two-photon luminescence imaging of single gold nanorods," Proc. Natl. Acad. Sci. USA 102(44), 15752-15756 (2005).

[61] L. Tong, Q. Wei, A. Wei, and J. X. Cheng, "Gold nanorods as contrast agents for biological imaging: optical properties, surface conjugation and photothermal effects," Photochem. Photobiol. 85(1), 21-32 (2009).

[62] T. Y. Ohulchanskyy, I. Roy, K. T. Yong, H. E. Pudavar, and R. N. Prasad, "High-resolution light microscopy using luminescent nanoparticles," WIREs Nanomed. Nanobiotechnol. 2(2), 162-175 (2010).

[63] D. Nagesha, G. S. Laevsky, P. Lampton, R. Banyal, C. Warner, C. DiMarzio, and S. Sridhar, "In vitro imaging of embryonic stem cells using multiphoton luminescence of gold nanoparticles," Int. J. Nanomedicine 2(4), 813-819 (2007).

[64] Y. Zhang, J. Yu, D. J. S. Birch, and Y. Chen, "Gold nanorods for fluorescence lifetime imaging in biology," J. Biomed. Opt. 15(2), 0205041-0205043 (2010).

[65] C. L. Chen, L. R. Kuo, C. L. Chang, Y. K. Hwu, C. K. Huang, S. Y. Lee, K. Chen, S. J. Lin, J. D. Huang, and Y. Y. Chen, "In situ real-time investigation of cancer cell photothermolysis mediated by excited gold nanorod surface plasmons," Biomaterials 31(14), 4104-4112 (2010).

[66] H. Okamoto and K. Imura, "Near-field imaging of optical field and plasmon wavefunctions in metal nanoparticles," J. Mater. Chem. 16(40), 3920-3928 (2006).

[67] K. Imura, T. Nagahara, and H. Okamoto, "Near-field two-photon-induced photoluminescence from single gold nanorods and imaging of plasmon modes," J. Phys. Chem. B 109(27), 13214-13220 (2005).

[68] W. H. Ni, X. S. Kou, Z. Yang, and J. F. Wang, "Tailoring longitudinal surface plasmon wavelengths, scattering and absorption cross sections of gold nanorods," ACS Nano 2(4), 677-686 (2008).

[69] C. Xu and W. W. Webb, "Measurement of two-photon excitation cross sections of molecular fluorophores with data from 690 to 1050 nm," JOSA B 13(3), 481-491 (1996).

[70] R. Gans, "Form of ultramicroscopic particles of silver," Ann. Phys. 47(10), 270-284 (1915).

[71] M. A. Albota, C. Xu, and W. W. Webb, "Two-photon fluorescence excitation cross sections of biomolecular probes from 690 to 960 nm," Appl. Opt. 37(31), 7352-7356 (1998).

[72] G. T. Boyd, Z. H. Yu, and Y. R. Shen, "Photoinduced luminescence from the noble metals and its enhancement on roughened surfaces," Phys. Rev. B 33(12), 7923-7936 (1986).

[73] S. Eustis and M. A. El-Sayed, "Aspect ratio dependence of the enhanced fluorescence intensity of gold nanorods: experimental and simulation study," J. Phys. Chem. B 109(34), 16350-16356 (2005).

[74] M. Guerrisi and R. Rosei, "Splitting of the interband absorption edge in Au", Phys. Rev. B 12(2), 557-563 (1975).

[75] X. Huang, S. Neretina, and M. A. El-Sayed, "Gold nanorods: from synthesis and properties to biological and biomedical applications," Adv. Mater. 21(48), 4880-4910 (2009).

[76] K. S. Lee and M. A. El-Sayed, "Dependence of the enhanced optical scattering efficiency relative to that of absorption for gold metal nanorods on aspect ratio, size, end-cap shape and medium refractive index," J. Phys. Chem. B 109(43), 20331-20338 (2005).

[77] C. Sönnichsen and A. P. Alivisatos, "Gold nanorods as novel nonbleaching plasmon-based orientation sensors for polarized single-particle microscopy," Nano Lett. 5(2), 301-304 (2005).

[78] S. Link, C. Burda, B. Nikoobakht, and M. A. El-Sayed, "Laser-induced shape changes of colloidal gold nanorods using femtosecond and nanosecond laser pulses" J. Phys. Chem. B 104(26), 6152-6163 (2000).

[79] A. Bouhelier, R. Bachelot, G. Lerondel, S. Kostcheev, P. Royer, G. P. Wiederrecht, "Surface plasmon characteristics of tunable photoluminescence in single gold nanorods," Phys. Rev. Lett. 95(26), 2674051-2674054 (2005).

[80] R. E. Hummel, Electronic Properties of Materials, 37-61, 4th ed. (Springer, New York, 2011).

[81] R. Rosei, and P. Winsemius, "Splitting of the interband absorption edge in Au," Phys. Rev. B 12(2), 557-563 (1975).

[82] Tearney G J, Regar E, Akasaka T et al. Consensus standards for acquisition, measurement, and reporting of intravascular optical coherence tomography studies: a report from the International Working Group for Intravascular Optical Coherence Tomography Standardization and Validation. J Am Coll Cardiol 2012; 59:1058-72.

[83] Tearney G J, Yabushita H, Houser S L et al. Quantification of macrophage content in atherosclerotic plaques by optical coherence tomography. Circulation 2003; 107: 113-9.

[84] MacNeill B D, Jang I K, Bouma B E et al. Focal and multi-focal plaque macrophage distributions in patients with acute and stable presentations of coronary artery disease. J Am Coll Cardiol 2004; 44:972-9.

[85] Tahara S, Morooka T, Wang Z et al. Intravascular optical coherence tomography detection of atherosclerosis and inflammation in murine aorta. Arterioscler Thromb Vasc Biol 2012; 32:1150-7.

[86] Raffel O C, Tearney G J, Gauthier D D, Halpern E F, Bouma B E, Jang I K. Relationship between a systemic inflammatory marker, plaque inflammation, and plaque characteristics determined by intravascular optical coherence tomography. Arterioscler Thromb Vasc Biol 2007; 27:1820-7.

[87] Raffel O C, Merchant F M, Tearney G J et al. In vivo association between positive coronary artery remodelling and coronary plaque characteristics assessed by intravascular optical coherence tomography. Eur Heart J 2008; 29:1721-8.

[88] Chia S, Raffel O C, Takano M, Tearney G J, Bouma B E, Jang I K. Comparison of coronary plaque characteristics between diabetic and non-diabetic subjects: An in vivo optical coherence tomography study. Diabetes Res Clin Pract 2008; 81:155-60.

[89] Tanaka A, Tearney G J, Bouma B E. Challenges on the frontier of intracoronary imaging: atherosclerotic plaque macrophage measurement by optical coherence tomography. J Biomed Opt 2010; 15:011104.

[90] Ali Z A, Roleder T, Narula J et al. Increased thin-cap neoatheroma and periprocedural myocardial infarction in drug-eluting stent restenosis: multimodality intravascular imaging of drug-eluting and bare-metal stents. Circ Cardiovascular Intery 2013; 6:507-17.

[91] Cilingiroglu M, Oh J H, Sugunan B et al. Detection of vulnerable plaque in a murine model of atherosclerosis with optical coherence tomography. Catheter Cardiovasc Intery 2006; 67:915-23.

[92] Virmani R, Kolodgie F D, Burke A P, Farb A, Schwartz S M. Lessons from sudden coronary death—A comprehensive morphological classification scheme for atherosclerotic lesions. Arterioscler Thromb Vasc Biol 2000; 20:1262-1275.

[93] Bornstein P, Sage H. Structurally distinct collagen types. Annu Rev Biochem 1980; 49:957-1003.

[94] Falk E, Nakano M, Bentzon J F, Finn A V, Virmani R. Update on acute coronary syndromes: the pathologists' view. Eur Heart J 2013; 34:719-28.

[95] Tavakoli S, Zamora D, Ullevig S, Asmis R. Bioenergetic profiles diverge during macrophage polarization: implications for the interpretation of $^{18}$F-FDG PET imaging of atherosclerosis. J Nucl Med 2013; 54:1661-7.

[96] Mourant J R, Freyer J P, Hielscher A H, Eick A A, Shen D, Johnson T M. Mechanisms of light scattering from biological cells relevant to noninvasive optical-tissue diagnostics. Appl Opt 1998; 37:3586-3593.

[97] van der Meer F J, Faber D J, Baraznji Sassoon D M, Aalders M C, Pasterkamp G, van Leeuwen T G. Localized measurement of optical attenuation coefficients of atherosclerotic plaque constituents by quantitative optical coherence tomography. IEEE Trans Med Imaging 2005; 24:1369-76.

[98] Wang T, Mancuso J J, Kazmi S M et al. Combined two-photon luminescence microscopy and OCT for macrophage detection in the hypercholesterolemic rabbit aorta using plasmonic gold nanorose. Lasers Surg Med 2012; 44:49-59.

[99] Phipps J E, Sun Y, Saroufeem R, Hatami N, Fishbein M C, Marcu L. Fluorescence lifetime imaging for the characterization of the biochemical composition of atherosclerotic plaques. J Biomed Opt 2011; 16:096018.

[100] van Soest G, Regar E, Goderie T P et al. Pitfalls in plaque characterization by OCT: image artifacts in native coronary arteries. J Am Coll Cardiol Img 2011; 4:810-3.

[101] Nadra I, Mason J C, Philippidis P et al. Proinflammatory activation of macrophages by basic calcium phosphate crystals via protein kinase C and MAP kinase pathways: a vicious cycle of inflammation and arterial calcification? Circ Res 2005; 96:1248-56.

[102] Rajamaki K, Lappalainen J, Oorni K et al. Cholesterol crystals activate the NLRP3 inflammasome in human macrophages: a novel link between cholesterol metabolism and inflammation. PLoS One 2010; 5:e11765.

[103] Marcu L, Jo J A, Fang Q et al. Detection of rupture-prone atherosclerotic plaques by time-resolved laser-induced fluorescence spectroscopy. Atherosclerosis 2009; 204:156-64.

[104] Motz J T, Fitzmaurice M, Miller A et al. In vivo Raman spectral pathology of human atherosclerosis and vulnerable plaque. J Biomed Opt 2006; 11:021003.

[105] Maldonado N, Kelly-Arnold A, Vengrenyuk Y et al. A mechanistic analysis of the role of microcalcifications in atherosclerotic plaque stability: potential implications for plaque rupture. Am J Physiol Heart Circ Physiol 2012; 303:H619-28.

[106] Bostrom K, Watson K E, Horn S, Wortham C, Herman I M, Demer L L. Bone morphogenetic protein expression in human atherosclerotic lesions. J Clin Invest 1993; 91:1800-9.

[107] Manfrini O, Mont E, Leone O et al. Sources of error and interpretation of plaque morphology by optical coherence tomography. Am J Cardiol 2006; 98:156-9.

[108] Rieber J, Meissner O, Babaryka G et al. Diagnostic accuracy of optical coherence tomography and intravascular ultrasound for the detection and characterization of atherosclerotic plaque composition in ex-vivo coronary specimens: a comparison with histology. Coron Artery Dis 2006; 17:425-30.

[109] Kume T, Akasaka T, Kawamoto T et al. Assessment of coronary arterial plaque by optical coherence tomography. Am J Cardiol 2006; 97:1172-5.

[110] Virmani R, Kolodgie F D, Burke A P, Farb A, Schwartz S M. Lessons from sudden coronary death—A comprehensive morphological classification scheme for atherosclerotic lesions. Arterioscler Thromb Vasc Biol 2000; 20:1262-1275.

[111] Tearney G J, Yabushita H, Houser S L, et al. Quantification of macrophage content in atherosclerotic plaques by optical coherence tomography. Circulation 2003; 107: 113-9.

[112] MacNeill B D, Jang I K, Bouma B E, et al. Focal and multi-focal plaque macrophage distributions in patients with acute and stable presentations of coronary artery disease. J Am Coll Cardiol 2004; 44:972-9.

The invention claimed is:

1. An apparatus comprising:
   an imaging device comprising an optical coherence tomography light source, wherein the imaging device is configured to obtain an image of a lumen via a catheter inserted into the lumen; and
   a non-transitory computer readable medium configured to perform the following steps used in the evaluation of the image of the lumen:
   (1) identify the catheter;
   (2) identify the lumen;
   (3) obtain a plurality of A-scans and B-scans of the lumen;
   (4) calculate distances between the catheter and the lumen for each A-scan and the overall mean distance to the catheter (Mean$_{overall}$);
   (5) calculate the average of A-scans closer to the catheter than Mean$_{overall}$ ($A_{closer}$) and the average of A-scans further to the catheter than Mean$_{overall}$ ($A_{further}$);
   (6) normalize $A_{closer}$ and $A_{further}$ by the range of values in a B-scan (maximum value−minimum value), $A_{closerN}$ and $A_{furtherN}$; and
   (7) identify bright spots as those pixels in each A-scan that are greater than the corresponding pixels in $A_{closerN}$ or $A_{furtherN}$, depending on whether the A-scan lumen is closer or further to the catheter compared to Mean$_{overall}$.

2. The apparatus of claim 1 wherein the apparatus is configured to analyze a spatial pattern of the bright spots.

3. The apparatus of claim 2 wherein the apparatus is configured to document a clinically relevant outcome based on the spatial pattern of bright spots.

4. The apparatus of claim 1 wherein the apparatus is configured to analyze location depths of a plurality of bright spots, wherein the location depth of each bright spot is measured from a surface of the lumen to a location of the bright spot.

5. The apparatus of claim 4 wherein the apparatus is configured to document a clinically relevant outcome based on the location depths of the plurality of bright spots.

6. The apparatus of claim 4 wherein the lumen is a vascular wall of a blood vessel.

7. The apparatus of claim 1 wherein the apparatus is configured to perform texture analysis of the lumen.

8. The apparatus of claim 7 wherein the apparatus is configured to document a clinically relevant outcome based on the texture analysis and a presence of bright spots.

9. The apparatus of claim 1 wherein the optical coherence tomography light source is configured as a swept source optical coherence tomography light source.

10. The apparatus of claim 1 wherein the optical coherence tomography light source is configured as a broadband optical coherence tomography light source.

11. The apparatus of claim 1 wherein the imaging device further comprises:
   a splitter configured to direct a first wavelength emitted from the coherence tomography light source to a reference path and to a sample path, wherein the sample path is directed to the lumen through an optical fiber inserted into the catheter;
   a short-pulsed light source configured to emit a second wavelength;
   a first dichroic element and a second dichroic element; and
   a visual display configured to display an image of the lumen.

12. The apparatus of claim 11 wherein the optical fiber is a photonic crystal fiber.

13. The apparatus of claim 11 wherein the imaging device further comprises a balanced detector.

14. The apparatus of claim 13 wherein the balanced detector is configured to minimize a non-interfering OCT component.

15. The apparatus of claim 11 wherein the imaging device further comprises a photon counting detector.

16. The apparatus of claim 15 wherein the photon counting detector is a photomultiplier tube.

17. The apparatus of claim 16 wherein the photon counting detector is an avalanche photo diode.

18. The apparatus of claim 16 wherein the photon counting detector is configured to detect two-photon luminescence.

19. The apparatus of claim 11 wherein the second dichroic element is configured to direct two photon luminescence toward a photon counting detector.

20. The apparatus of claim 11 wherein the first dichroic element is configured to direct the first and second wavelengths to the sample path.

21. The apparatus of claim 11 wherein the sample path is directed to a sample site that comprises nanoparticles.

22. The apparatus of claim 11 further comprising a visual display configured to display an image of the sample site.

23. The apparatus of claim 21 wherein the nanoparticles are configured as nanorods.

24. The apparatus of claim 23 wherein the nanorods comprise gold and have a surface plasmon resonance of approximately 756 nm.

25. The apparatus of claim 11 further comprising a dispersion compensating element.

26. The apparatus of claim 25 wherein the dispersion compensating element is configured to compensate dispersion differences between the reference path and the sample path.

27. The apparatus of claim 25 wherein the dispersion compensating element is configured to pre-compensate two-photon luminescence excitation light.

28. An apparatus comprising:
an optical coherence tomography light source configured to emit a first wavelength;
a splitter configured to direct the first wavelength emitted from the coherence tomography light source to a reference path and to a sample path, wherein the sample path is directed to a sample site through an optical fiber;
a short-pulsed light source configured to emit a second wavelength;
a first dichroic element and a second dichroic element; and
a visual display configured to display an image of the sample site, wherein the apparatus is configured to enhance a portion of the image of the sample site based on the distance between the optical fiber and the sample site.

29. The apparatus of claim 28 where in order to enhance the portion of the image of the sample site, the apparatus is configured to:
obtain a plurality of A-scans and B-scans of the sample site;
calculate distances between the optical fiber and the sample site for each A-scan and the overall mean distance to the optical fiber ($Mean_{overall}$);
calculate the average of A-scans closer to the optical fiber than $Mean_{overall}$ ($A_{closer}$) and the average of A-scans further to the optical fiber than $Mean_{overall}$ ($A_{further}$);
normalize $A_{closer}$ and $A_{further}$ by the range of values in a B-scan (maximum value−minimum value), $A_{closerN}$ and $A_{furtherN}$; and
identify bright spots as those pixels in each A-scan that are greater than the corresponding pixels in $A_{closerN}$ or $A_{furtherN}$, depending on whether the A-scan sample site is closer or further to the optical fiber compared to $Mean_{overall}$.

30. The apparatus of claim 29 wherein the apparatus is configured to analyze a spatial pattern of the bright spots.

31. The apparatus of claim 30 wherein the apparatus is configured to document a clinically relevant outcome based on the spatial pattern of bright spots.

32. The apparatus of claim 29 wherein the apparatus is configured to analyze location depths of a plurality of bright spots, wherein the location depth of each bright spot is measured from a surface of the sample site to a location of the bright spot.

33. The apparatus of claim 32 wherein the apparatus is configured to document a clinically relevant outcome based on the location depths of the plurality of bright spots.

34. The apparatus of claim 32 wherein the sample site is a vascular wall of a blood vessel.

35. The apparatus of claim 29 wherein the apparatus is configured to perform texture analysis of the sample site.

36. The apparatus of claim 35 wherein the apparatus is configured to document a clinically relevant outcome based on the texture analysis and a presence of bright spots.

37. A method of diagnosing a medical condition, the method comprising:
obtaining an image of a sample site using an optical coherence tomography light source emitting light from an optical fiber;
obtaining a plurality of A-scans and B-scans of the sample site;
calculating distances between the optical fiber and the sample site for each A-scan and the overall mean distance to the optical fiber ($Mean_{overall}$);
calculating the average of A-scans closer to the optical fiber than $Mean_{overall}$ ($A_{closer}$) and the average of A-scans further to the optical fiber than $Mean_{overall}$ ($A_{further}$);
normalizing $A_{closer}$ and $A_{further}$ by the range of values in a B-scan (maximum value−minimum value), $A_{closerN}$ and $A_{furtherN}$; and
identifying bright spots as those pixels in each A-scan that are greater than the corresponding pixels in $A_{closerN}$ or $A_{furtherN}$, depending on whether the A-scan sample site is closer or further to the optical fiber compared to $Mean_{overall}$.

38. The method of claim 37 further comprising analyzing a spatial pattern of the bright spots.

39. The method of claim 38 further comprising diagnosing a medical condition based on the spatial pattern of the bright spots.

40. The method of claim 37 further comprising analyzing location depths of a plurality of bright spots, wherein the location depth of each bright spot is measured from a surface of the sample site to a location of the bright spot.

41. The method of claim 40 further comprising diagnosing a medical condition based on the location depths of the plurality of bright spots.

* * * * *